(12) United States Patent
Chen et al.

(10) Patent No.: US 8,236,527 B2
(45) Date of Patent: Aug. 7, 2012

(54) RECOMBINANT PRODUCTION OF AUTHENTIC HUMAN PROTEINS USING HUMAN CELL EXPRESSION SYSTEMS

(75) Inventors: Ridong Chen, Naperville, IL (US); Soon Seog Jeong, Naperville, IL (US); Hui Feng, Chicago, IL (US)

(73) Assignee: Humanzyme Limited, George Town, Grand Cayman (KY)

( * ) Notice: Subject to any disclaimer, the term of this patent is extended or adjusted under 35 U.S.C. 154(b) by 0 days.

(21) Appl. No.: 12/922,293

(22) PCT Filed: Mar. 12, 2009

(86) PCT No.: PCT/US2009/036975
§ 371 (c)(1),
(2), (4) Date: Nov. 16, 2010

(87) PCT Pub. No.: WO2009/114702
PCT Pub. Date: Sep. 17, 2009

(65) Prior Publication Data
US 2011/0053221 A1    Mar. 3, 2011

Related U.S. Application Data

(60) Provisional application No. 61/036,667, filed on Mar. 14, 2008, provisional application No. 61/147,627, filed on Jan. 27, 2009.

(51) Int. Cl.
*C12P 1/00* (2006.01)
*C12N 15/64* (2006.01)
*C12N 15/00* (2006.01)
*C12N 15/74* (2006.01)
*C12N 5/02* (2006.01)
*C12N 5/10* (2006.01)
*C12N 5/071* (2006.01)
*C12N 5/00* (2006.01)

(52) U.S. Cl. ........ 435/69.1; 435/41; 435/91.4; 435/440; 435/471; 435/476; 435/325; 435/363; 435/366; 435/320.1; 435/383

(58) Field of Classification Search .................. None
See application file for complete search history.

(56) References Cited

U.S. PATENT DOCUMENTS
2003/0092160 A1    5/2003 Bout et al.

FOREIGN PATENT DOCUMENTS
WO    WO 2004/085620 A2    10/2004
WO    WO 2007/103447 A2    9/2007

OTHER PUBLICATIONS

Crystal et al., Administration of a Replication-Deficient Adeno-Associated Virus Gene Transfer Vector Expressing the Human CLN2 cDNA to the Brain of Children with Late Infantile Neuronal Ceroid Lipofuscinosis; Human Gene Therapy, vol. 15, pp. 1131-1154, 2004.*
Ng et al., Regulation of the human beta-actin promoter by upstream and intron domains; NAR, vol. 17, No. 2, pp. 601-615, 1989.*
Hanawa et al., High-Level Erythroid Lineage-Directed Gene Expression Using Globin Gene Regulatory Elements After Lentiviral Vector-Mediated Gene Transfer into Primitive Human and Murine Hematopoietic Cells); Human Gene Therapy, vol. 13, pp. 2007-2016, 2002.*
Kessler et al., Gene delivery to skeletal muscle results in sustained expression and systemic delivery of a therapeutic protein; PNAS, vol. 93, pp. 14082-14087, 1996.*
Genbank record x03922, 2011.*
PCT International Search Report, International Application No. PCT/US2009/036975, dated Dec. 4, 2009.
Xu et al., "Optimization of Transcriptional Regulatory Elements for Constructing Plasmid Vectors", *Gene*, (2001), pp. 149-156, 11; 272, Elsevier Science B.V.
Skibeli et al., "Sugar Profiling Proves that Human Serum Erythropoietin Differs from Recombinant Human Erythropoietin", *Blood*, Dec. 2001, pp. 3626-3634, vol. 98, No. 13, The American Society of Hematology, www.blodjournal.org.
Leong et al., "Optimized Expression and Specific Activity of IL-12 by Directed Molecular Evolution", *PNAS*, Feb. 4, 2003, pp. 1163-1168, vol. 100, No. 3, www.pnas.org/cgi/doi/10.1073/pnas.0237327100.
Tsao et al., "Development and Improvement of a Serum-Free Suspension Process for the Production of Recombinant Adenoviral Vectors using HEK293 Cells", *Cytotechnology*, (2001), pp. 189-198, vol. 37, Kluwer Academic Publishers, The Netherlands.
Baldi et al., "Transient Gene Expression in Suspension HEK-293 Cells: Application to Large-Scale Protein Production", *Biotechnol. Prog.*, (2005), pp. 148-153, vol. 21, No. 1, American Chemical Society and American Institute of Chemical Engineers.
Schlaeger et al., "Transient Gene Expression in Mammalian Cells Grown in Serum-Free Suspension Culture", *Cytotechnology*, (1999), pp. 71-83, vol. 30, No. 1-3, Kluwer Academic Publishers, The Netherlands.
Newman et al., "Human Cell-Expressed IL-12 has Enhanced Pro-Inflammatory Activity", *Cytokine*, (2007), pp. 29-30, vol. 39.
Office Action; In re: Chinese Patent Application Serial No. 200980117839.0; Dated: Dec. 7, 2011; Applicant: Humanzyme Limited; (7 pgs.). English Translation of Chinese Office Action; In re: Chinese Patent Application Serial No. 200980117839.0; Dated: Dec. 7, 2011; Applicant: Humanzyme Limited; (13 pgs.).
Hage, T., et al.; "Chain A, Interleukin-4 Receptor Alpha Chain Complex"; PDB, 1IAR__A; Amino Acid Sequence; (5 pgs.).
Walter, M.R., "Chain A, Three-Dimensional Structure of Recombinant Human Granulocyte-Macrophage Colony-Stimulating Factor"; PDB, 1CSG__A; Amino Acid Sequence; (4 pgs.).
Sundstrom, et al.; "Chain A, 1:2 Complex of Human Growth Hormone With Its Soluble Binding Protein"; PDB, 1HWG__A; Amino Acid Sequence; (4 pgs.).
Orita, T., et al. Interleukin 6, hIL6 [human, Peptide Recombinant, 185 aa]; GenBank, AAB30962; Amino Acid Sequence; (3 pgs.).

* cited by examiner

*Primary Examiner* — Celine Qian
*Assistant Examiner* — Addison D Ault
(74) *Attorney, Agent, or Firm* — Foley & Lardner LLP

(57) ABSTRACT

The present invention relates to novel expression cassettes and vectors for efficiently producing authentic recombinant human proteins from stable cultures of novel human cell lines, the authentic recombinant proteins produced therefrom, and antibodies raised against those authentic recombinant proteins.

18 Claims, 47 Drawing Sheets

FIGURE 6A: GM-CSF
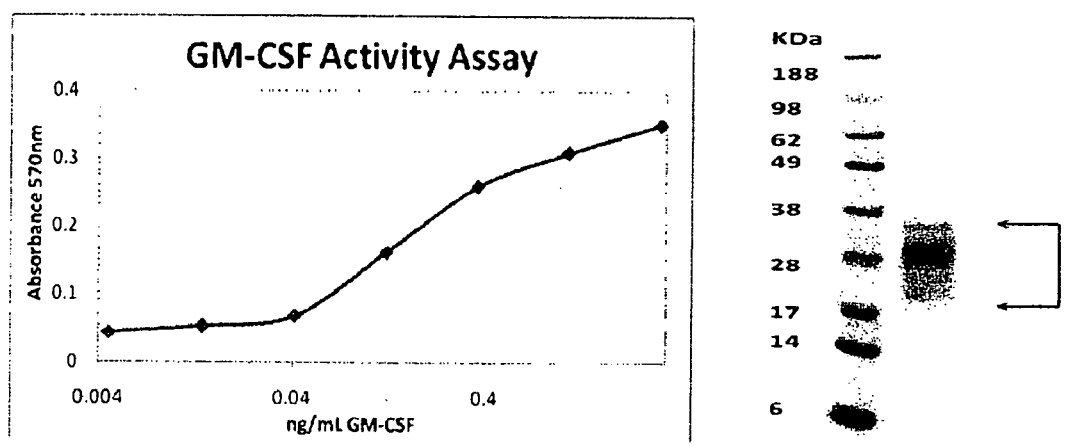

FIGURE 6B: IL-4
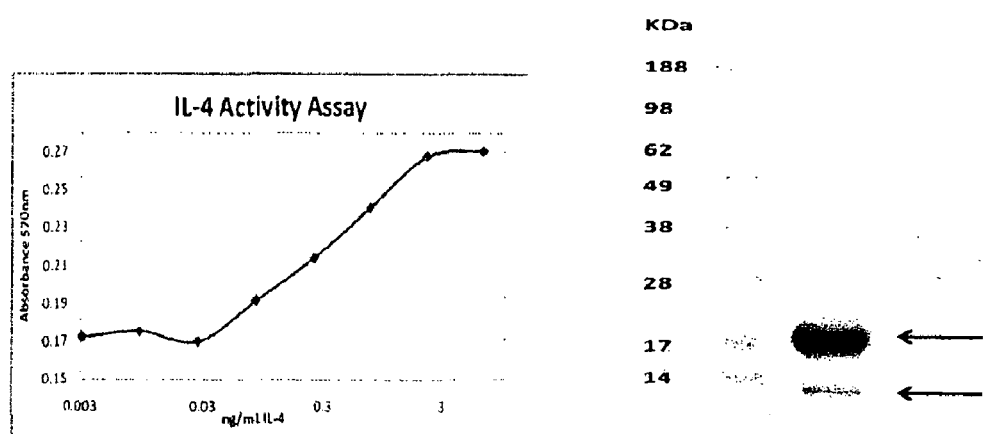

FIGURE 6C: SOMATOTROPIN
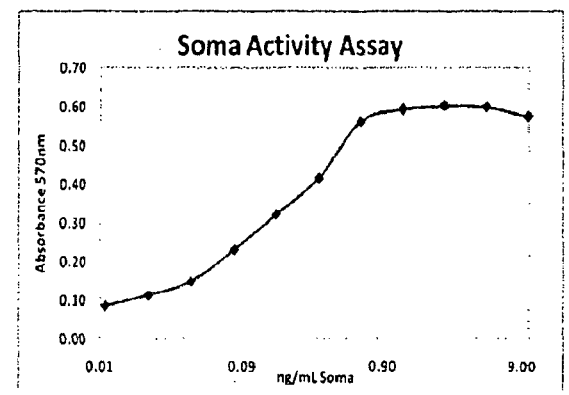
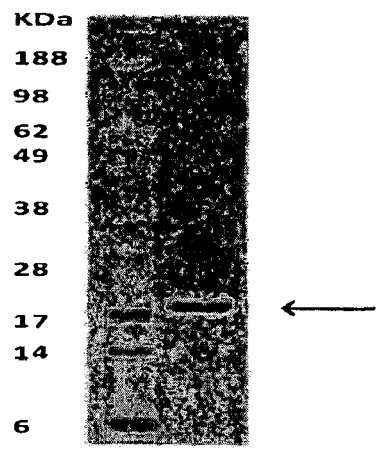

FIGURE 6E: VEGF-165
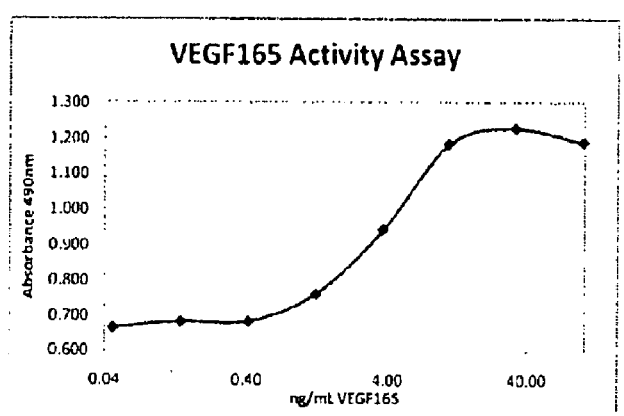
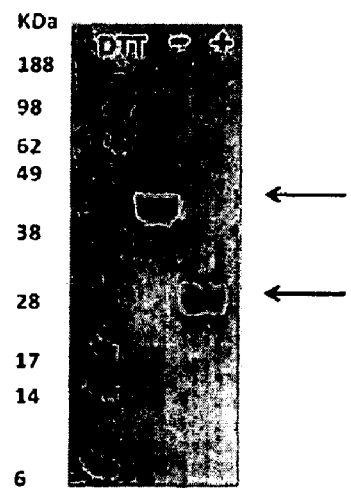

FIGURE 6H
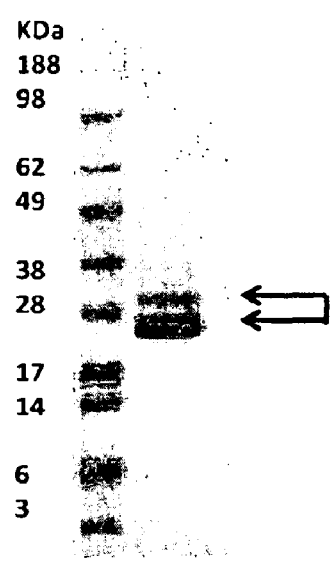
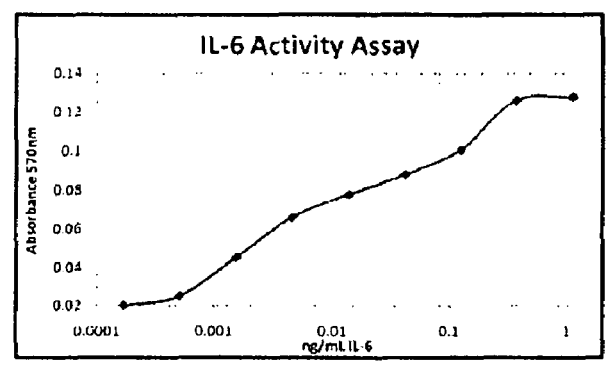

FIGURE 14 (CONSTRUCT SCHEMATICS)
(A)

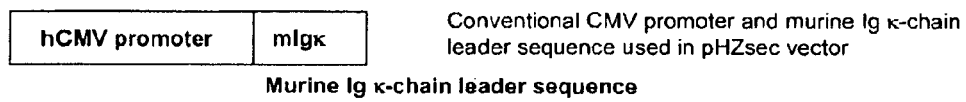

Conventional CMV promoter and murine Ig κ-chain leader sequence used in pHZsec vector Murine Ig κ-chain leader sequence (B)
pHZhag vector                          pCAG vector

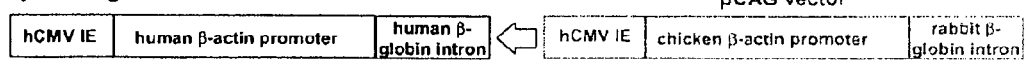

Conventional CMV promoter and murine Ig κ-chain leader sequence used in pHZsec vector Murine Ig κ-chain leader sequence

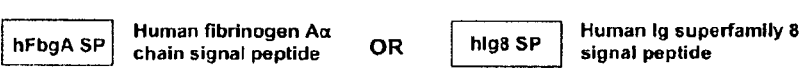

Human fibrinogen Aα chain signal peptide    OR    Human Ig superfamily 8 signal peptide pHZA vector                pHZI vector

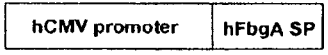    AND    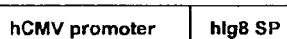

(C)
pHZhag vector                          pCAG vector

Human fibrinogen Aα chain signal peptide    OR    Human Ig superfamily 8 signal peptide pHZhagA vector

pHZhagI vector

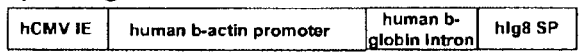

1. Control
2. pHZ-TGF-β1
3. pHZhag-TGF-β1
4. pHZA-TGF-β1
5. pHZI-TGF-β1

FIGURE 20 (A) and (B)
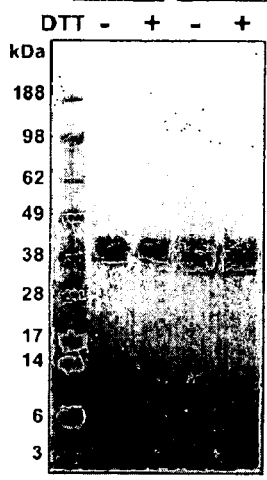
(B) Neutral and acidic glycan contents of human EPO vs CHO EPO
| Fraction | Glycan Type | Total Ion Intensity Human-EPO | Total Ion Intensity CHO-EPO |
|---|---|---|---|
| 10% AcCN | Neutral | 278 | n/a |
| 20% AcCN | Neutral | 366 | n/a |
| 40% AcCN | Neutral | 191 | 235 |
| 40% AcCN +0.05% TFA | Acidic | 94 | 74 |

(C) Acidic glycan structures of the recombinant EPO from human and CHO cells

| m/z [M-H]⁻ | Human EPO | CHO EPO |
|---|---|---|
| 2442 | 7 % | 12 % |
| 2807 | 28 % | 59 % |
| 3172 | 4 % | 24 % |
| 3537 | n/a | 3 % |

- ■ GlcNAc
- ☐ HexNAc
- ● Mannose
- ○ Hexose
- ▲ Fucose
- ◆ NeuAc

IL-23 Human cell
IL-23 Insect

FIGURE 22 (A) – (D)
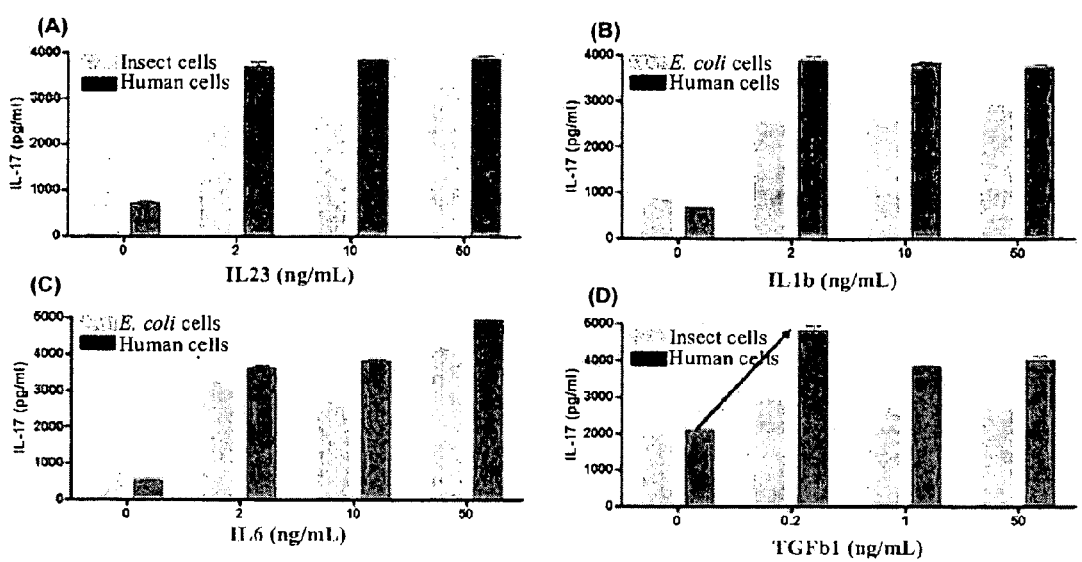

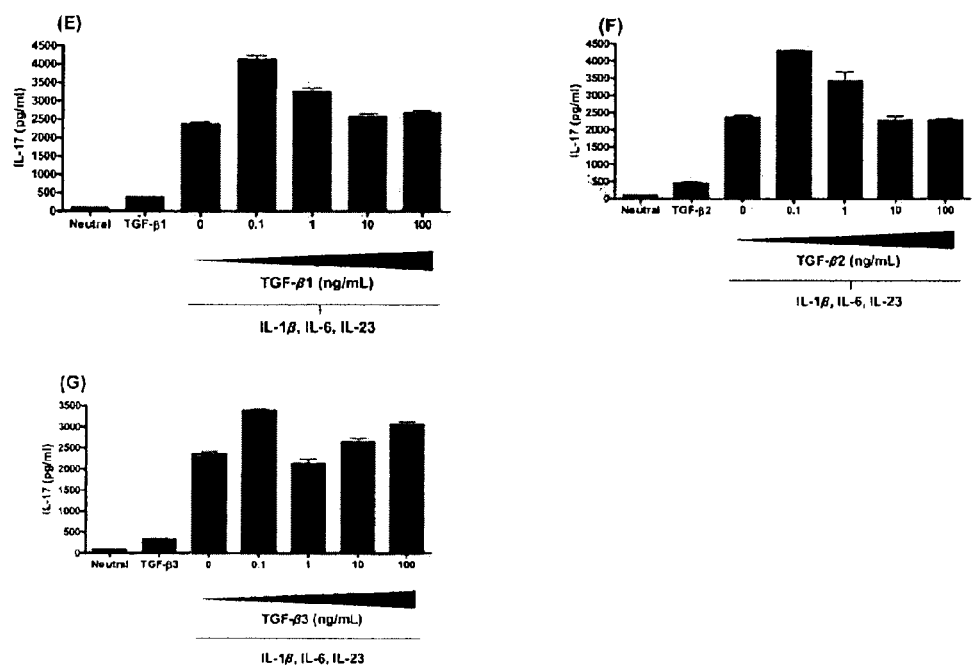
FIGURE 22 (E) – (G)

FIGURE 27

See the following schematic:

```
                                                                          Signal
                                                                          cleavage
                                            IgK leader sequence              ↓
ATG GAG ACA GAC ACA CTC CTG CTA TGG GTA CTG CTG CTC TGG GTT CCA GGT TCC ACT GGT / GAC
Met Glu Thr Asp Thr Leu Leu Leu Trp Val Leu Leu Leu Trp Val Pro Gly Ser Thr Gly / Asp Srf I
GCG CCC / GGG CCG ...
Ala Pro   Gly
```

RECOMBINANT PRODUCTION OF AUTHENTIC HUMAN PROTEINS USING HUMAN CELL EXPRESSION SYSTEMS

CROSS-REFERENCE

This International PCT application claims priority to U.S. Provisional Application Ser. Nos. 61/147,627, filed on Jan. 27, 2009, and 61/036,667, filed on Mar. 14, 2008, both of which are incorporated herein by reference.

FIELD OF THE INVENTION

The present invention relates to human expression systems for recombinantly producing authentic human proteins.

SUMMARY OF THE INVENTION

Aspects of the present invention include novel expression cassettes and vectors for efficiently producing authentic recombinant human proteins from stable cultures of novel human cell lines. Also contemplated by the present invention are authentic recombinant proteins produced by these novel methods and from these novel components, as well as antibodies raised against those authentic recombinant proteins. The recombinantly-produced, authentic human proteins of the present invention may also be used in gene therapy, and the vectors disclosed herein may also be employed in gene therapy to express human proteins in vivo or in vitro/ex vivo in order to treat a particular disease.

It is to be understood that the vectors and cell lines of the present invention can be used together and also independently from one another. That is, a novel vector of the present invention may be introduced into a novel cell line of the present invention, such as HZ-293TS (described below), and within that cell express a particular encoded human protein, such as a cytokine. It is equally true, however, that any vector may be expressed in a cell line of the present invention. Similarly, any of the vectors disclosed herein may be expressed in different human cell lines, not only in those described herein.

An aspect of the present invention is an expression cassette that facilitates the expression of an authentic human protein in human cells, which comprises in a 5'- to 3'-orientation the following sequences:

(1) a cytomegalovirus (CMV) enhancer element;
(2) a human promoter sequence, wherein the promoter is selected from the group consisting of (i) a human β-actin promoter, (ii) a human serum albumin promoter, and (iii) a human fibrinogen promoter;
(3) a human globin gene intron; and
(4) a signal peptide, such as immunoglobulin superfamily 8 signal peptide or alpha-fibrinogen signal peptide.

A desired polynucleotide, which encodes a human protein or fragment thereof of interest, is operably linked to and inserted downstream of the signal peptide sequence. The expression cassette may also further comprise a polyadenylation signal sequence and/or a termination site sequence, such that the desired polynucleotide is operably linked to and inserted between the signal peptide and the polyadenylation/termination signal sequence. Alternatively, the desired polynucleotide itself may comprise a termination signal sequence or a polyadenylation signal sequence to aid appropriate termination of transcription.

In whatever arrangement and permutation of these regulatory elements, it is clear to the skilled person that expression of this cassette will produce a fusion protein comprising the protein or polypeptide encoded by the desired polynucleotide linked to the signal peptide. Thus, a signal peptide/human protein may be produced according to the present invention and then the signal peptide cleaved away from the fusion protein to leave the authentic human protein intact. In this respect, the human cell machinery recognizes the cleavage site during the protein synthesis. For instance, the cell's Golgi apparatus and signal peptides interact during the protein synthesis at which point the signal peptide is separated from the fusion protein. Accordingly, when the protein is secreted to the extracellular space the signal peptide is already separated.

An expression cassette of the present invention therefore may comprise the following operably linked sequences: (1) a CMV immediate early enhancer sequence; (2) a human β-actin promoter; (3) a globin gene intron; (4) an alpha-fibrinogen signal peptide; (5) a desired polynucleotide; and (6) a polyadenylation/termination sequence. The skilled artisan is aware that other permutations of these elements can differ and exchanged with other sequences. For instance, as indicated above, an expression cassette may be constructed that employs a human serum albumin promoter or a human fibrinogen promoter in the cassette in place of the human β-actin promoter. Thus, an expression cassette of the present invention may comprise the following operably linked sequences: (1) a CMV immediate early enhancer sequence; (2) a human β-actin promoter; (3) a globin gene intron; (4) immunoglobulin superfamily 8 signal peptide; (5) a desired polynucleotide; and (6) a polyadenylation/termination sequence.

Accordingly, in one aspect of the present invention is an expression vector comprising a desired polynucleotide operably linked to a CMV immediate early enhancer, a beta-actin promoter sequence, a human globin gene intron sequence, and an immunoglobulin superfamily 8 signal peptide, wherein the desired polynucleotide is operably linked to, and positioned downstream of, the signal peptide.

Another aspect of the present invention is an expression vector comprising a desired polynucleotide operably linked to a CMV immediate early enhancer, a beta-actin promoter sequence, a human globin gene intron sequence, and an alpha-fibrinogen signal peptide, wherein the desired polynucleotide is operably linked to, and positioned downstream of, the signal peptide.

In this regard, the present invention is not limited to the use of only human genetic elements in the expression cassette. For instance, the promoter and gene intron sequence, as well as the signal peptide can be from the genome of other species. For instance, the sequences can be from any mammal, reptile, bird, fish, insect, bacterial, fungus, yeast, virus, or amphibian. Thus, in one embodiment of the present invention, the expression cassette comprises nucleotide sequences for a promoter, intron, and signal peptide from a species other than human, such as from mouse, monkey, ape, rat, cat, dog, rabbit, gerbil, hamster, guinea pig, pig, cattle, or sheep.

In another embodiment, the signal sequence encodes a sequence that helps transport the transcribed RNA molecule product to the cell's Golgi body or to the extracellular space.

Another aspect of the present invention is a method for producing a protein in a cell, comprising introducing an expression vector of the present invention into a cell, wherein the cell may be from the same species as the sequences of the vector cassette, wherein the gene sequence in the cassette is transcribed and translated in the cell to produce the protein that it encodes. In one embodiment, the expression vector is introduced into a cell that is from the same species as the species from which the promoter, intron, and signal peptide sequences are obtained from. In one embodiment, both the cell and the sequences of the cassette are from any mammal, reptile, bird, fish, insect, bacterial, fungus, yeast, virus, or amphibian. Thus, in one embodiment of the present invention, the cell and sequences of the expression cassette are both from a species selected from the group consisting of human, mouse, monkey, ape, rat, cat, dog, rabbit, gerbil, hamster, guinea pig, pig, cattle, and sheep. In one embodiment, the cell is a human cell. In another embodiment, the human cell is a human kidney cell. In one embodiment, the human kidney cell is an HEK 293 cell. A sequence of the expression cassette of the present invention includes a nucleic acid sequence of interest, or a desired polynucleotide, operably linked downstream of the signal peptide and operably linked thereby to the enhancer, promoter, and intron so that the nucleic sequence of interest or the desired polynucleotide is expressed. Examples of desired polynucleotides include, but are not limited to, those disclosed in (1)-(13) of the Sequences listing below, as well as those listed in Table 5. Thus, examples of human cytokines encoded by the desired polynucleotide of the present invention include but are not limited to Activin A, Activin B, Activin A/2xINHbA, Activin B/2xINHbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2B, IFN-γ, $\beta_1$IFN-$\beta_1$, IGF I, IGF II, IGF IIv1, IGF IIv2, IL10, IL11, IL12, IL15, IL17/IL17A, IL17F, β IL1 β IL2, IL23, IL27, IL28A/IFN-lambda-2, IL28B/IFN-lambda-3, IL29/IFN-lambda-1, IL1β, IL2 IL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFα, PDGFβ, Persephin, SCF, SDF1α, SHH, Somatotropin, TGF β1, TGF β2, TGF β3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14. A desired polynucleotide of the present invention may encode EPO, G-CSF, GM-CSF, IL-2, IL-4, IL-6, M-CSF, Noggin, SCF, Somatotropin, TGFβ1, TNFα, or VEGF-165.

One aspect of the present inventive method comprises isolating the produced protein from the cell. In one embodiment, the method further comprises raising an antibody against the isolated protein. Thus, another aspect of the present invention is an antibody raised against an epitope of the protein produced by any one of the inventive methods disclosed herein. In one embodiment, the antibody is a polyclonal or monoclonal antibody.

Another aspect of the present invention is a cell, which expresses the cassette of any of the expression vectors disclosed herein. In one embodiment, the cell is from the same species as sequences in the cassette. In one embodiment, the cell is a human cell.

Another aspect of the present invention is a method for inducing an immune response in an individual, comprising expressing the cassette of any of the expression vectors disclosed herein in cells of the individual, wherein expression of the gene sequence produces a protein or RNA product that induces an immune response in the individual, and wherein the species of the individual is the same as the species of the sequences in the cassette.

Another aspect of the present invention is an expression vector, comprising a cassette which comprises (A) a human promoter sequence, (B) a human signal sequence, (C) a human gene sequence, and (D) a human polyadenylation signal sequence, wherein all of the sequences are operably linked.

In one embodiment, the sequence of an exemplary CMV enhancer element is shown in SEQ ID NO: 27, which is the human CMV immediate early (IE) enhancer. The sequence of an exemplary human promoter sequence is shown in SEQ ID NO: 28 and is the human beta-actin promoter sequence. The sequence of an exemplary human globin gene intron is shown in SEQ ID NO: 29. Examples of signal peptides includes the human fibrinogen alpha chain signal peptide shown in SEQ ID NO: 30, and the human immunoglobulin superfamily member 8 precursor signal shown in SEQ ID NO: 31.

Examples of expression cassettes that include these elements operably linked to one another are shown in SEQ ID NOs: 32 and 33.

Any desired polynucleotide or nucleic acid of interest can be inserted downstream of the signal peptide so that it is operably linked to the signal peptide and the regulatory elements, such as the CMV IE enhancer, human promoter, and human globin intron sequences, of the expression cassette. A cassette of the present invention may further comprise a cleavage site sequence between the globin gene intron and the signal peptide so that post-transcriptional processing generates a protein that comprises the desired protein linked at its 5'-end to the signal peptide. The signal peptide may be a signal peptide that transports the protein to the extracellular space. A desired polynucleotide of the present invention includes polynucleotides that encode cytokines. Thus, one aspect of the present invention is an isolated, recombinant human cytokine that is authentically glycosylated and comparable in structure to the same cytokine that is native, endogenously-expressed in vivo from a human cell.

In one embodiment of the present invention, the recombinant human cytokine is comparable to the native cytokine because the recombinant human cytokine comprises sugar chains that are terminated with human-specific N-acetylneuraminic acids. In one embodiment, the sugar chains are covalently attached to the surface of the cytokine. In another embodiment of the present invention a sugar chain comprises at least one of N-acetylglucosamine, fucose, mannose, and galactose moities. In another embodiment, the authentically glycosylated cytokine only comprises sugar chains from a human cell and no sugar chain moieties derived from any non-human cell.

In one embodiment, the recombinant human cytokine that is encoded by a desired polynucleotide of the present invention is selected from the group consisting of Activin A, Activin B, Activin A/2xINHbA, Activin B/2xINHbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2B, IFN-γ, $\beta_1$IFN-$\beta_1$, IGF I, IGF II, IGF IIv1, IGF IIv2, IL10, IL11, IL12, IL15, IL17/IL17A, IL17F, β IL1 β IL2, IL23, IL27, IL28A/IFN-lambda-2, IL28B/IFN-lambda-3, IL29/IFN-lambda-1, IL1β, IL2 μL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFα, PDGFβ, Persephin, SCF, SDF1α, SHH, Somatotropin, TGF β1, TGF β2, TGF β3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14. See also the "List of Cloned Cytokine Genes" at Table 5. The recombinant human cytokine that is encoded by a desired polynucleotide of the present invention may also be selected from the group of cytokines listed in Table 5. In another embodiment, the human recombinant cytokine is selected from the group consisting of EPO, G-CSF, GM-CSF, IL-2, IL-4, IL-6, M-CSF, Noggin, SCF, Somatotropin, TGFβ1, TNFα, and VEGF-165.

Another aspect of the present invention is a recombinant method for producing an authentic human cytokine, comprising (1) transfecting a human cell that is able to survive on serum-free medium with any one of the expression vectors disclosed herein that comprises (i) a desired polynucleotide that encodes a human cytokine sequence and (ii) an antibiotic resistance gene; (2) (i) selecting those transfected cells that survive exposure to medium containing the antibiotic to which the antibiotic gene is resistant to, (ii) transferring those cells that survive antibiotic exposure to a liquid culture that has low-serum concentration, (3) reducing the serum concentration to 0% over a period of time; and (4) isolating the human cytokine expressed from cells that grow in the serum-free medium liquid culture, wherein the isolated human cytokine is biologically active. In another aspect of the present invention, the human cells can be co-transfected with one vector that comprises the desired polynucleotide that comprises the cytokine sequence, and another distinct vector that comprises the antibiotic resistance gene expression cassette. Thus, the present invention contemplates the use of one vector (that contains both the cytokine sequence and the antibiotic resistance gene sequence) or the use of two vectors (one containing the cytokine gene sequence, the other containing the antibiotic resistance gene sequence), for transfecting the human cells of the present invention.

In one embodiment, the desired polynucleotide comprises a sequence that encodes a signal peptide secretory sequence in frame with the sequence that encodes the human cytokine. In another embodiment, the desired polynucleotide is operably linked to a promoter and a terminator.

In one embodiment, the serum-free medium comprises one or more antibiotics. In one embodiment, an antibiotic is neomycine (G418), hygromycine, zeocin, or blasticidine. In another embodiment, the step of reducing the serum concentration to 0% occurs during a period of time that is one day to several weeks. In one embodiment, the volume of liquid culture is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 liters, or more than 50 liters of culture, or any integer in between.

In another embodiment, the step of isolating the human cytokine comprises centrifuging an aliquot of the serum-free liquid cell culture and capturing the human cytokine from the supernatant into which it is secreted. In one embodiment, the step of isolating the human cytokine further comprises returning the human cells that have been pelleted from the centrifugation step to the same or different serum-free liquid cell culture vessel.

In one embodiment, the supernatant from which the secreted human cytokines are isolated contains no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of contaminating material or protein that is not the secreted human cytokine.

In one embodiment, the purity of a sample of supernatant comprising the secreted human cytokines is at least about 99% pure, at least about 98% pure, at least about 97% pure, at least about 96% pure, at least about 95% pure, at least about 94% pure, at least about 93% pure, at least about 92% pure, at least about 91% pure, at least about 90% pure, at least about 89% pure, at least about 88% pure, at least about 87% pure, at least about 86% pure, at least about 85% pure, at least about 84% pure, at least about 83% pure, at least about 82% pure, at least about 81% pure, or at least about 80% pure.

In one embodiment, the supernatant of the cell culture consists essentially of the expressed and secreted human cytokine protein.

In another embodiment, the supernatant of the cell culture consists of no other biologically active protein other than the expressed and secreted human cytokine protein.

Another aspect is an isolated, recombinant human cytokine produced by the recombinant method. In one embodiment, that isolated, recombinant human cytokine is selected from the group consisting of Activin A, Activin B, Activin A/2xINHbA, Activin B/2xINHbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2B, IFN-γ, β₁IFN-β₁, IGF I, IGF II, IGF IIv1, IGF IIv2, IL10, IL11, IL12, IL15, IL17/IL17A, IL17F, β IL1 β IL2, IL23, IL27, IL28A/IFN-lambda-2, IL28B/IFN-lambda-3, IL29/IFN-lambda-1, IL1β, IL2 IL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFα, PDGFβ, Persephin, SCF, SDF1α, SHH, Somatotropin, TGF β1, TGF β2, TGF β3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14. See also the "List of Cloned Cytokine Genes" at Table 5.

In one embodiment, none of the human cytokine proteins produced by the methods disclosed herein comprises a non-human sugar chain. That is, the human cytokine proteins of the present invention only comprises glycosylated sugar chains that have been covalently bound to their protein surface by enzymes and substrates available only in human cells.

Another aspect of the present invention is an antibody that is raised against any one of the isolated recombinant human cytokines disclosed herein. In one embodiment, the antibody is a monoclonal antibody. In another embodiment, it is a polyclonal antibody.

Another aspect of the present invention is a kit, comprising at least one of any isolated recombinant human cytokine or antibody disclosed herein.

Accordingly, to elaborate on the above embodiments, an aspect of the present invention is an expression vector, comprising a cassette which comprises the following operably linked expression elements:

(A) a cytomegalovirus enhancer element sequence;

(B) a human promoter sequence selected from the group consisting of (i) a human actin promoter sequence, (ii) a human serum albumin promoter sequence, and (iii) a human fibrinogen promoter sequence;

(C) a human globin gene intron sequence; and (D) a human signal peptide sequence.

In one embodiment, the expression vector further comprises a desired polynucleotide positioned downstream of the signal peptide sequence and operably linked to elements (A), (B), (C), and (D) of claim 1. In another embodiment, either (i) the desired polynucleotide is operably linked to a termination signal sequence that is located in the expression vector downstream of the human signal peptide sequence, or (ii) the desired polynucleotide itself comprises a termination signal sequence.

In one embodiment, the human promoter sequence is a functional human beta-actin promoter sequence. In another embodiment, the CMV enhancer element is the CMV immediate early enhancer sequence. In another embodiment, the signal peptide sequence is (A) a sequence that comprises intron 1 of the human immunoglobulin A gene and a cleavage recognition sequence positioned toward the 3'-end of the intron sequence, (B) alpha-fibrinogen signal peptide, or (C) an immunoglobulin superfamily 8 signal peptide.

In one embodiment, the desired polynucleotide encodes a cytokine. In another embodiment the encoded cytokine is selected from the group consisting of Activin A, Activin B, Activin A/2xINHbA, Activin B/2xINHbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2B, IFN-γ, ß$_1$IFN-β$_1$, IGF I, IGF II, IGF IIv1, IGF IIv2, ID10, IL11, IL12, IL15, IL17/IL17A, IL17F, β IL1 β IL2, IL23, IL27, IL28A/IFN-lambda-2, IL28B/IFN-lambda-3, IL29/IFN-lambda-1, IL113, IL2 IL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFα, PDGFβ, Persephin, SCF, SDF1α, SHH, Somatotropin, TGF β1, TGF β2, TGF β3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14. See also the "List of Cloned Cytokine Genes" at Table 5. In another embodiment, the encoded cytokine is selected from the group consisting of EPO, G-CSF, GM-CSF, IL-2, IL-4, IL-6, M-CSF, Noggin, SCF, Somatotropin, TGFβ1, TNF α, and VEGF-165.

In one embodiment, an expression vector of the present invention ("pHZhag") comprises operably linked nucleotide sequences for (i) an hCMV IE, (ii) a human beta-actin promoter, and (iii) a human beta-globin intron.

In one embodiment, an expression vector of the present invention ("pHZA") comprises operably linked nucleotide sequences for (i) an hCMV promoter, and (ii) a human fibrinogen subunit A signal peptide.

In one embodiment, an expression vector of the present invention ("pHZI") comprises operably linked nucleotide sequences for (i) an hCMV promoter, and (ii) a human Ig superfamily 8 signal peptide.

In one embodiment, an expression vector of the present invention ("pHZhagA") comprises operably linked nucleotide sequences for (i) an hCMV IE, (ii) a human beta-actin promoter, (iii) a human beta-globin intron, and (iv) a human fibrinogen subunit A signal peptide;

In one embodiment, an expression vector of the present invention ("pHZhagI") comprises operably linked nucleotide sequences for (i) an hCMV IE, (ii) a human beta-actin promoter, (iii) a human beta-globin intron, and (iv) a human Ig superfamily 8 signal peptide.

In one embodiment, an expression vector of the present invention ("pHZhag-TGFβ1") comprises operably linked nucleotide sequences for (i) an hCMV IE, (ii) a human beta-actin promoter, (iii) a human beta-globin intron, and (iv) TGFβ1.

In one embodiment, an expression vector of the present invention ("phZhagI-TGFβ1") comprises operably linked nucleotide sequences for (i) an hCMV IE, (ii) a human beta-actin promoter, (iii) a human beta-globin intron, (iv) a human Ig superfamily 8 signal peptide, and (v) TGFβ1.

In any of these expression vectors a desired polynucleotide may be incorporated downstream, and operably linked to, the signal peptide of the particular expression vector, where the desired polynucleotide encodes a protein, such as a human protein.

Thus, another aspect of the present invention is a recombinant method for producing an authentic human protein, comprising introducing any one of the expression vectors of the present invention into a human cell, wherein the desired polynucleotide encodes a human protein and wherein expression of the desired polynucleotide in the human cell produces an authentic human protein.

In one embodiment, the authentic human protein has a similar size, structure, molecular weight, glycosylation pattern, and post-transcriptional modifications to that of a native version of the same human protein. The skilled person is aware of various assays and tests, such as chromatographic, gel, genetic, protein analyses, crystallography, and compositional analyses useful for characterizing proteins; a readily available one being protein gel electrophoresis of the recombinantly-produced protein of the present invention against a native, endogenous version of the same protein run alongside each other and a protein marker lane.

In one embodiment, the desired polynucleotide encodes a cytokine. In another embodiment the encoded cytokine is selected from the group consisting of Activin A, Activin B, Activin A/2xINHbA, Activin B/2xINHbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2B, IFN-γ, ß$_1$IFN-β$_1$, IGF I, IGF II, IGF IIv1, IGF IIv2, IL10, IL11, IL12, IL15, IL17/IL17A, IL17F, β IL1 β IL2, IL23, IL27, IL28A/IFN-lambda-2, IL28B/IFN-lambda-3, IL29/IFN-lambda-1, IL1B, IL2 IL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFα, PDGFβ, Persephin, SCF, SDF1α, SHH, Somatotropin, TGF β1, TGF β2, TGF β3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14. See also the "List of Cloned Cytokine Genes" at Table 5. In another embodiment, the encoded cytokine is selected from the group consisting of EPO, G-CSF, GM-CSF, IL-2, IL-4, IL-6, M-CSF, Noggin, SCF, Somatotropin, TGFβ1, TNF α, and VEGF-165.

In one embodiment, the human cell is HZ-293TS which is a human kidney embryonic cell line derived from HEK293T, and adapted according to the present invention and was deposited in accordance with the Budapest Treaty with the American Type Culture Collection (ATCC®) at the ATCC® IP, Licensing and Services 10801 University Boulevard, Manassas, Va. 20110-2209, USA, bearing the ATCC® biological deposit accession number of PTA-10165, on Jul. 1, 2009 (date of receipt by the ATCC®), by HumanZyme, Inc. 2201 W. Campbell Park Dr., Chicago, Ill. 60612. References elsewhere in this specification to this deposited cell line are cited in correspondence to the ATCC® "PTA-10165" patent deposit designation number.

In one embodiment, the recombinant method further comprises isolating the authentic human protein from the human cell.

Another aspect of the present invention is a recombinantly-produced, authentic human protein produced by a human cell that expresses the desired polynucleotide in any one of the expression vectors of the present invention, wherein the desired polynucleotide encodes a human protein, and wherein expression of the desired polynucleotide produces an authentic human protein. In one embodiment, the desired polynucleotide encodes a cytokine. In another embodiment the encoded cytokine is selected from the group consisting of Activin A, Activin B, Activin A/2xINHbA, Activin B/2xIN-HbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2B, IFN-γ, $\beta_1$IFN-$\beta_1$, IGF I, IGF II, IGF IIv1, IGF IIv2, IL10, IL11, IL12, IL15, IL17/IL17A, IL17F, β IL1 β IL2, IL23, IL2, IL28A/IFN-lambda-2, IL28B/IFN-lambda-3, IL 29/IFN-lambda-1, IL1B, IL2 IL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFa, PDGFO, Persephin, SCF, SDF1α, SHH, Somatotropin, TGF β1, TGF β2, TGF β3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14. See also the "List of Cloned Cytokine Genes" at Table 5. In another embodiment, the encoded cytokine is selected from the group consisting of EPO, G-CSF, GM-CSF, IL-2, IL-4, IL-6, M-CSF, Noggin, SCF, Somatotropin, TGFβ1, TNF α, and VEGF-165.

In one embodiment, the recombinantly-produced, authentic human protein is produced from the HZ-293TS human cell line deposited under and bearing the ATCC biological deposit accession number of PTA-10165, deposited on Jul. 1, 2009.

In one embodiment, the glycosylation pattern of the authentic human protein is similar to the native, endogenous version of that human protein. In a further embodiment, the size, structure, and molecular weight of the authentic human protein is similar to the size and molecular weight of the native, endogenous version of that human protein. In one embodiment, the authentic human protein is TGFβ. In another embodiment, the desired polynucleotide encodes the noggin protein and wherein expression of the desired polynucleotide produces in the cell a disulfide-bonded noggin dimer.

Another aspect of the present invention is an antibody raised against an epitope of any one of the authentic human proteins produced by the recombinant methods described herein. In one embodiment, the antibody is a polyclonal or monoclonal antibody. In another embodiment, the antibody is a monoclonal antibody raised against G-CSF.

Another aspect of the present invention is a stable human cell line called HZ-293TS (a human kidney embryonic cell line adapted to proliferate on serum-free medium), deposited under and bearing the ATCC biological deposit accession number of PTA-10165, deposited on Jul. 1, 2009. In one embodiment of the present invention, the viability of cells of the HZ-293TS cell line is longer than that of other HEK293 cell types. That is, the HZ-293TS cells remain viable for 3, 4, 5, 6, 7, 8, 9, 10, 11, 12, 13, or 14, or more than 14 days viable compared to other HEK293 cell types.

Another aspect of the present invention is any human cell that expresses any of the expression vectors disclosed herein. In one embodiment, the human cell is HZ-293TS deposited under and bears the ATCC biological deposit accession number of PTA-10165, deposited on Jul. 1, 2009.

Another aspect of the present invention is a method for treating a condition associated with cell growth, cell proliferation, cell differentiation, or inflammation, comprising administering (A) any one of the recombinantly-produced authentic human proteins described herein or obtainable by the methods described herein, or (B) any one of the antibodies disclosed herein or obtainable by the methods described herein, to an individual who has a condition associated with cell growth, proliferation, differentiation, or inflammation. In one embodiment, the method comprises administering an inventive antibody raised against TNFα to an individual with a condition associated with inflammation or arthritis.

In one embodiment, the method comprises administering an inventive antibody raised against VEGF to an individual with a condition associated with cancer or cell proliferation.

One aspect of the present invention is the use of an antibody raised against an epitope of any one of the authentic human proteins of the present inventing as a diagnostic agent for detecting that human protein from a sample. In one embodiment, the antibody is used as a diagnostic agent in an ELISA assay to detect the human protein.

In another embodiment, the sample is a human tissue sample, human cell sample, human blood sample, or a human bodily fluid sample. In a further embodiment, the human protein is a cytokine.

Another aspect of the present invention is a method for treating a condition associated with cell growth, cell proliferation, cell differentiation, or inflammation, comprising administering a vector that expresses a desired polynucleotide which encodes a protein to an individual who has a condition associated with cell growth, proliferation, differentiation, or inflammation, wherein the expressed protein in a cell of the individual helps to treat the condition.

BRIEF DESCRIPTION OF THE DRAWINGS

FIG. 14: Vector schematics.

FIG. 22 (H) depicts flow cytometry analysis on Human Th17 Differentiation by Authentic human TGF-β1. See Example 17 below.

FIG. 27: IgK leader sequence showing signal cleavage site and engineered Srf I restriction site (SEQ ID NO:38).

DETAILED DESCRIPTION

A. General Considerations

Cytokines and the Present Invention

Figure 1:
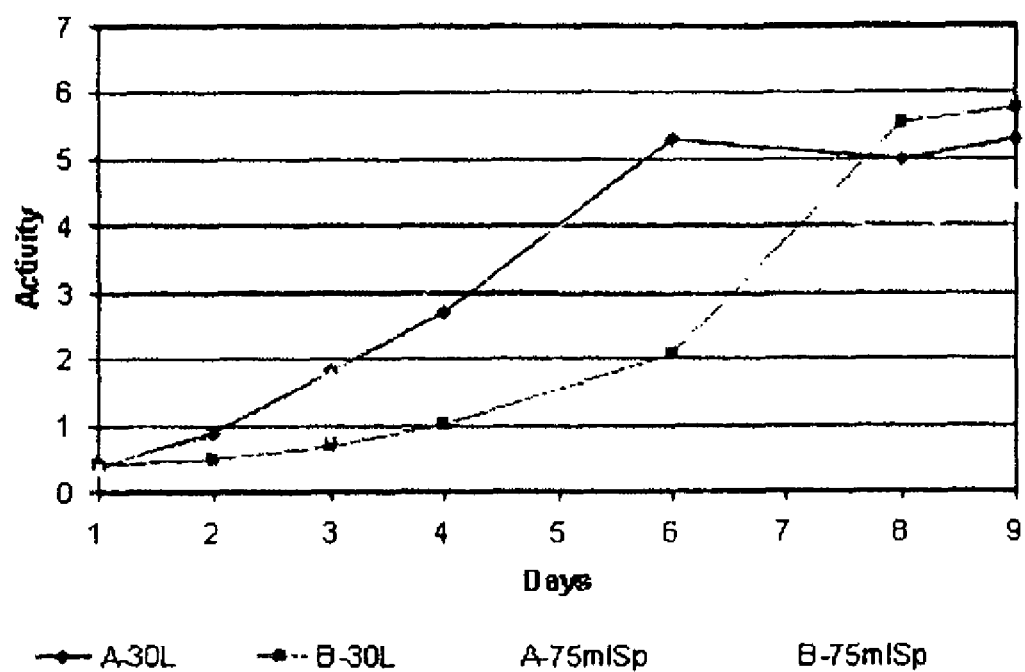
FIG. 1: Protein activity for alkaline phosphastase over the course of 9 days between two different volumes of human cell culture (75 ml vs 30 liters).

Cytokines are a group of proteins and polypeptides that organisms use as signaling molecules. Most cytokines are glycoproteins less than 30 kDa in size and bind to specific, high-affinity cell surface receptors. Due to their central role in the immune system, cytokines are involved in a variety of immunological, inflammatory and infectious diseases and widely used in research, diagnostics and therapeutics. Currently, these proteins are predominantly produced in non-human cells, such as *E. coli*, and therefore lack authenticity, as described below, due to the absence of relevant glycosylation patterns. Furthermore, a number of important cytokines are not commercially available due to inadequate proteolytic processing or other post-translational modification that occur in such non-human cell expression systems. See Table 1. Authentic in this regard intimates that the recombinant human cytokine that is expressed according to the present inventive stable human cell expression method conforms to its native endogenous counterpart that is normally expressed in the human cell in vivo and reproduces certain features that are associated with that native counterpart. That is, for example, a recombinant human IFNα that is expressed using the present inventive stable human cell method, looks like, and has essentially the same structure, biological activity, size, molecular weight, folding patterns, and glycosylation patterns as, the native human IFNα. Thus, a human protein that is expressed by the present inventive method may be regarded as an "authentic protein," or "authentic cytokine" or a "recombinant, authentic" protein and so on. Its in vivo counterpart may be regarded as the native or endogenous cytokine or protein. Such "authentic" features of the proteins and cytokines expressed by the inventive stable human cell expression system are disclosed in more detail below. By contrast, a human IFNα protein that is expressed from an *E. coli* cell, or from a yeast or fungal cell, or from an insect cell, or from a non-human mammalian cell, such as in a Chinese Hamster Ovary cell, is not considered to be an "authentic" human IFNα protein in this context. Accordingly, an "authentic" recombinantly-produced protein of the present invention is one that is highly similar to one or more features and properties of the native version of the protein, such as, but not limited to the same structure, biological activity, size, molecular weight, protein folding patterns, dimerization properties, disulfide-bonding properties, and surface-bound glycosylation patterns.

(a) Cytokine Families

It is possible to group many cytokines together based on structural similarities that each constituent member shares other members, as well as other similarities based on their respective primary amino acid sequences. See Chapter 1 of The Cytokine Handbook, Volumes 1 and 2, Fourth Edition, Eds. Thomson & Lotze, which are both incorporated herein by reference in their entireties. According to shared structural features, therefore, the following "families" of individual cytokines can be grouped as follows:

(1) IL2/IL-4: representative members include IL-2, IL-4, IL-5 GM-CSF.

(2) IL-6/IL12: representative members include IL-6 and IL-12.

(3) Interferons—α/β: representative members include IFN-α (many subtypes), IFN-β, IFN-ω, and IFN-τ.

(4) Tumor necrosis factors: representative members include TNF-α, LT-α (TNF-β), LT-β, Fas ligand, CD40 ligand, TRAIL, BAFF, APRIL, RANK, and LIGHT.

(5) IL-10: representative members include IL-10, IL-19, IL-20, IL-22, and IL24.

(6) IL-17: representative members include IL-17 and IL-25.

(7) Interleukin-1: representative members include IL-1α, IL-1β, IL-1 receptor antagonist, and IL-18.

(8) TGF-β: representative members include TGF-β, bone morphogenetic proteins, Inhibins, and Activins.

(9) Chemokines: representative members include CXC subfamily (CXCLI-16), CC subfamily (CCLI-28), C subfamily (CLI/Lymphotactin), and CX3C subfamily (CX3CLI/Fractalkin).

Most cytokines are simple polypeptides or glycoproteins. Some of them can form dimmers and some are produced transiently and induce biological responses and cellular cascades by binding to specific high affinity cell surface receptors. Phenotypically, such responses include increases or decreases in the rate of cell proliferation, changes in cell differentiation state, and changes in the expression of some differentiated functions. Thus, for example, interleukin-1 (IL-1) activates T cells; IL-2 stimulates proliferation of antigen-activated T and B cells; IL-4, IL-5, and IL-6, stimulate proliferation and differentiation of B cells; Interferon gamma (IFNγ) activates macrophages; and IL-3, IL-7 and Granulocyte Monocyte Colony-Stimulating Factor (GM-CSF) stimulate hematopoiesis. Table 2 (from microvet.arizona.edu/courses/MIC419/Tutorials/cytokines.html), which is incorporated herein by reference, highlights some additional information about the source, target, and function of certain cytokines.

Cytokines can exist as monomers and dimers. With respect to the latter, cytokines can exist as homodimers, where two monomers of the same cytokine are joined together via a disulfide bond, or as heterodimers, such as in the case for IL12, IL23, IL27, and IL35. In the native human cell in vivo, two different cytokine genes are expressed from the genome and joined together via disulfide bond formation between appropriate residues on each cytokine. In artificial recombinant systems, these genes have to be expressed separately in different cultures, the resultant cytokine proteins extracted and isolated and then linked together in a further bonding step. According to the present invention, however, a stable human cell can be transfected with both desired cytokine genes and, because the resultant protein product in each case is authentic with respect to folding, epitope-presentation, and glycosylation, the two cytokines will naturally come together and form the heterodimer via disulfide bond linkage. Hence, the supernatant in that case will contain already-formed heterodimers.

The present invention is not limited to these particular cytokines or to polynucleotides that encode these particular proteins. Rather, an aspect of the invention is the recombinant expression of cytokine mutants, homologs, splice variants, or isomers that either are known to exist or are created to determine its effect on a certain cytokine parameter. Thus, the present invention also encompasses the recombinant production of authentic cytokine variants that comprise one or more amino acid substitutions, deletions, insertions, or splice junctions that differ from a native cytokine sequence, or which represents a mutated cytokine sequence that might be associated with some disease or disorder. A cytokine DNA sequence may be engineered to comprise such mutations and used for research purposes to ascertain the effect of that, or those, mutations on cytokine function or downstream in the relevant cytokine pathway. All of these proteins and mutants and variants therefore can be designed into a polynucleotide that is cloned into an expression cassette of the present invention so that it can be expressed in the human expression system of the present invention and subsequently used as described herein.

(b) Functions and Associated Diseases, such as Asthma and Allergies

Each cytokine can have multiple functions depending upon the cell that produces it and the target cell(s) upon which it acts, which may be on distant target cells (endocrine), on target cells adjacent to those that produce them (paracrine) or on the same cell that produces the cytokine (autocrine).

Of the families identified above, there are four major categories of cytokines:

(1) Interferons: interferon alpha (IFNα) is produced by the buffy coat layer from white blood cells and is used in treatment of a variety of malignant and immune disorders. Interferon beta (IFNβ) is produced by fibroblasts and is currently being evaluated in the treatment of multiple sclerosis. Interferon gamma (IFNγ) is produced by activated T cells and is an important immunoregulatory molecule, particularly in allergic diseases.

(2) Colony stimulating factors: includes granulocyte colony stimulating factor (G-CSF), macrophage colony stimulating factor (M-CSF), and granulocyte-macrophage colony stimulating factor (GM-CSF), as well as Interleukin (IL)-3, which can stimulate a variety of hematopoietic precursors and is being evaluated as a therapy in aplastic anemia and bone marrow transplantation; and c-Kit ligand (stem cell factor), which has recently been demonstrated as a cytokine necessary to cause the differentiation of bone marrow stem cells into their various precursor elements for eventual differentiation into RBC, WBC and megakaryocytes (platelets).

(3) Tumor necrosis factors (TNFs): TNFα is produced by activated macrophages and TNFβ is produced by activated T cells (both TH and CTL). These molecules seem to be involved in the pathogenesis of septic shock. TNFs can be useful clinically for treating human tumors.

(4) Interleukins: produced by a variety of cell types such as monocytes and macrophages, T cells, B cells and even non-leucocytes. Major interleukins that are involved in allergies are IL-4, IL-5, IL-10 and IFNγ. IL-4 causes a switch to IgE production by differentiating B cells. IFNγ can inhibit that switch and prevent the production of specific IgE. IL-10 can actually inhibit the activity of IFNγ, allowing the original IL-4 to proceed in the IgE cascade. Thus, an allergic response can be viewed as an allergen-specific production of excess IL-4 and/or IL-10, lack of adequate IFNγ production or both. Eosinophilic inflammation, a major component of allergic reactions, is under control of IL-5 and TNFα.

Accordingly, recombinantly-produce authentic human cytokines, or antibodies raised against them, can be administered to individuals with such disorders or diseases in which the function of the particular cytokine is implicated, for instance, IFNβ for treatment of multiple sclerosis.

3. Glycosylation and the Present Invention

Most proteins undergo post-translational modification, which can alter their physical and chemical properties, e.g., MW, pI, folding, stability, and biological activity. Glycosylation is the most prevalent type of post-translational modification, with estimations that 80% of all plasma proteins are glycosylated and the major part of the most important known human natural interferon alpha species are glycoproteins.

Glycoproteins are oligosaccharides or sugar chains that are covalently linked to proteins. The attachment of such sugar chains is performed in vivo by specific glycotransferases, which are highly sensitive to stimuli within the cell. The carbohydrate components of the glycoproteins affect the functionality of the molecule because they affect protein folding, oligomer assembly, and secretion, as well as solubility and aggregation of the expressed protein. These polysaccharide sugar chains therefore have various functions which culminate in conferring appropriate bioactivity and stability of the protein. Furthermore, certain protein-bound glycans are abundant in the nucleus and cytoplasm, where they appear to serve as regulatory switches.

The two most common classes of such sugar chains that are covalently attached to expressed proteins in vivo, are (1) N-glycans sugar chains which are covalently linked to a protein's asparagine residue within the consensus "Asn-X-Ser/Thr"; and which share a common pentasaccharide core region and fall into three classes, (a) high-mannose-type, (b) complex-type, and (c) hybrid-type; and (2) O-glycans which are linked to the protein via an N-acetylgalactosamine (GalNAc) to a serine or threonine residue in the protein. The corresponding glycosylation pathways that attach the sugar chains to the expressed protein in these ways typically occur in the cytosol, endoplasmic reticulum and the Golgi complex and involve glycosidases and glycosyltransferases to facilitate those attachments.

While not being bound to any particular theory of mechanistic action, a reason why a human protein that is expressed in the present inventive human cell system is superior to a counterpart that is expressed in a non-human cell lies in its authentically-glycosylated surface and appropriately-folded tertiary structure, for the reasons described above. That is, in an in vivo human cell environment, the post-translation modification machinery of the human cell attaches oligosaccharide or glycan sugar chains to the outer surface of the endogenously expressed protein so that the natively-produced protein is covered in an array of covalently attached sugar chains, which also helps to delay clearance of the protein from the bloodstream via the kidney renal system. Hence, the half-life of circulatory "authentic" human proteins is increased compared to the same protein expressed from a non-human cell.

Accordingly, while a non-human cell might be able express a human polynucleotide sequence from an introduced expression vector, the non-human cell environment does not lend itself to such post-translational modification. Consequently, the resultant and expressed protein necessarily lacks authenticity with respect its in vivo human counterpart that is properly folded and glycosylated. For this reason, the use of human proteins that have been expressed and purified from non-human cells in research, diagnostics, and therapeutic ends is inferior and undesirable.

(a) Human Vs. Non-Human Patterns

The non-human cell expression systems, e.g., bacterial, yeast, fungi, insect, and non-human mammalian systems, do not produce authentic human proteins. Common bacterial expression systems, such as *E. coli* cells, for instance, do not glycosylate recombinant mammalian proteins. Yeast and fungal expression systems can express human DNA sequences but the resultant glycosylation patterns from yeast and fungal cells are significantly different from the glycosylation processing of human cells. For instance, yeast and fungal cells attach non-human high-mannose sugar chains to the recombinantly-expressed human protein. The mannose chains may be immunogenic and the protein cleared much quicker from the system via the renal pathways. Insect cell expression systems are like yeast and fungi, although the length of the mannose chains that become attached to an insect-expressed protein are typically shorter than those attached in the yeast system.

As for non-human mammalian cell expression systems, the Chinese Hamster Ovary cells are the most commonly used by those practicing in this field of art. The CHO cells glycosylate differently to human cells. The CHO glycan structure is not human-like. In CHO cells, for instance, an expressed IFN-γ includes substituted fucose residues and high mannose oligosaccharide chains; in transgenic mice cells, the IFN-γ has variant N-glycan structures and in insect cells, the IFN-γ has tri-mannosyl core structures.

Transgenic animals also are used to produce human proteins, such as in goat milk, but similar problems exist, such as underglycosylation and the addition of non-human sialic acid (N-glycolylneuraminic acid).

Figure 4:
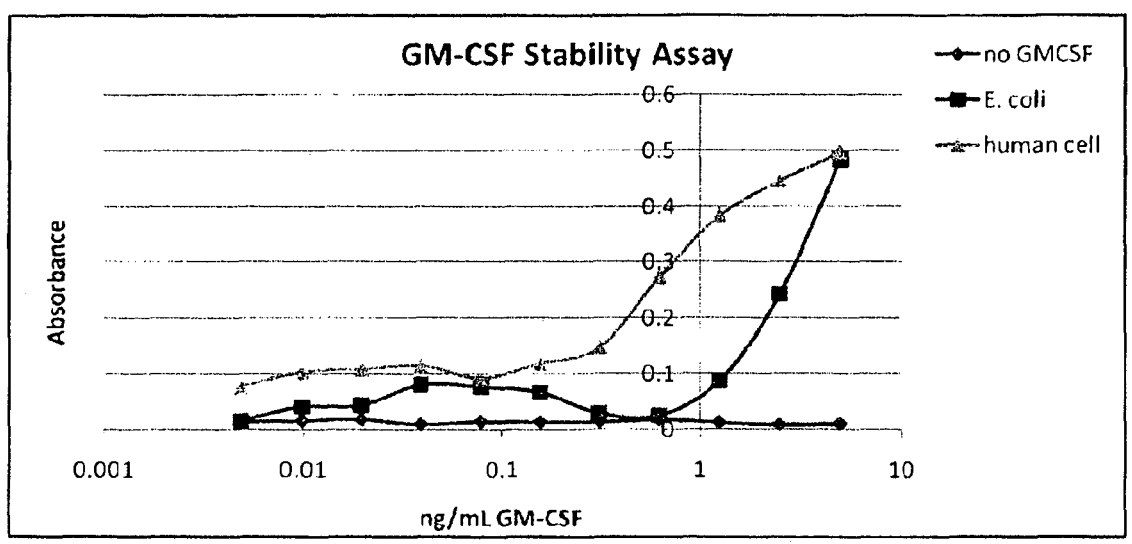
FIG. 4: Graph depicting a GM-CSF stability assay after expression in the inventive human (cell) cells and non-human cells (square).

By contrast, the N-glycans on human proteins have a specific order that terminate in N-acetylneuraminic acid. Accordingly, an aspect of the present invention is the recombinant expression of a human protein that comprises only human sugar chains. That is, an "authentic" protein of the present invention comprises one or more combinations of (1) N-acetylglucosamine, (2) fucose, (3) mannose, and (4) galactose chains which are terminated with N-acetylneuraminic acid. See Table 1 and FIG. 4. Accordingly, the human cell environment provides the appropriate and correct building blocks and mechanisms for processing a recombinantly-expressed, authentic human protein. Thus, in the context of human proteins and human cytokines, a recombinantly-produced, authentic human cytokine/protein that has an authentic glycosylation pattern includes, but is not limited to, a recombinant protein that comprises one or more combinations of (1) N-acetylglucosamine, (2) fucose, (3) mannose, and (4) galactose, sugar chains which are terminated with N-acetylneuraminic acid.

In some cases, not every individual cytokine protein that is expressed according to the present invention will comprise the same glycosylation pattern or extent of glycosylation as other cytokines isolated from an expression run. Thus, there may be subpopulations of an expressed cytokine that contain more or fewer attached human sugar chains, or which are processed to contain longer or shorter attached sugar chains, than others expressed from a particular human cell culture. This is not detrimental but rather approximates the state of glycosylation in vivo. Thus, when visualized on a protein gel, a smear around a predominantly-stained band may appear. In the present expression system, the smear does not represent protein contamination or degraded proteins or debris, but rather the distribution in protein size molecular weight is attributable to the extent of glycosylation and the number or respective sizes of the sugar chains attached to the recombinantly expressed protein. Thus, the more extensive is glycosylation, or the attachment of longer sugar chains, will increase the total apparent molecular weight of the glycosylated protein or cytokine.

B. Overview

The present invention therefore relates to a rapid and scalable method for producing authentic human proteins from stable cultures of human cells in vitro. The human cell expression system of the present invention is made to be more receptive to the introduction of a novel expression vector that encodes a human protein, as well as to suspension media that facilitates subsequent expression of that protein-encoding polynucleotide.

1. Advantages

The human proteins produced using the inventive human cells and methods, possess and exhibit more authentic "human-like" properties and structures than those that are expressed from non-human cells, particularly with respect to protein folding and post-translational modifications, such as proteolytic cleavage processing and glycosylation. For these reasons, a human protein that is expressed using the present methods and reagents exhibits a biological activity and circulatory half-life that more closely approximate its endogenous, naturally-expressed native form. Furthermore, the recombinantly-expressed human protein is more structurally comparable to the native protein in terms of folding and normally-available disulfide bond-forming residues and is consequently less immunogenic than its non-human cell-expressed counterpart. Likewise, the human cell, because it contains the appropriate human enzymes, can more readily glycosylate the expressed recombinant protein since its cellular environment and cytoplasmic organelles are ideally suited, unlike non-human cell systems, to recognize and manipulate human proteins. Accordingly, the glycosylation pattern and state of recombinant cytokines expressed in the stable human cell cultures of the present invention are glycosylated as though they had been produced in vivo endogenously.

Figure 5:
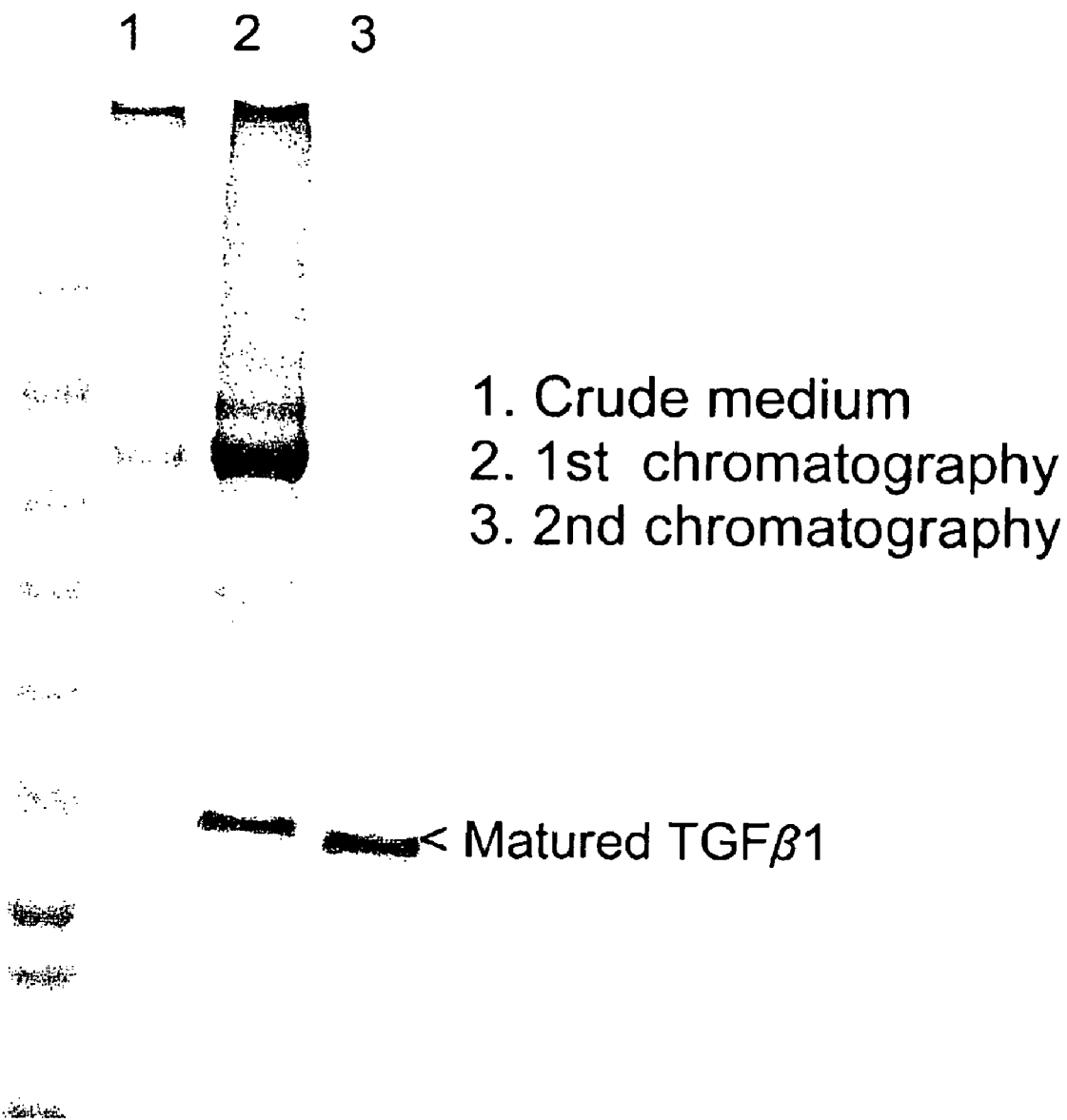
FIG. 5: SDS-PAGE gel evidencing the expression of active and mature TGFβ1, which is notoriously difficult to express.
Figure 6D:
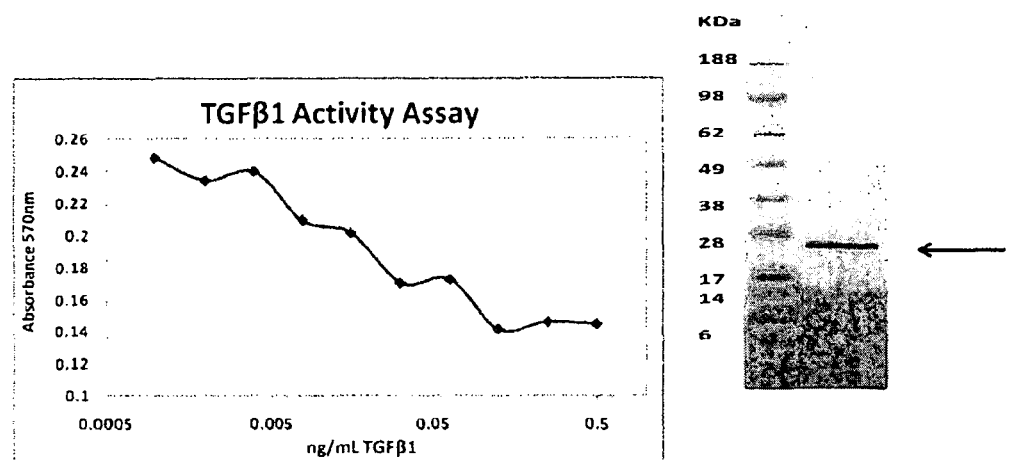
FIG. 6: Graphs and corresponding gels depict the activity and purity (as indicated on SDS gel staining) of cytokines produced according to the present inventive method. These examples convey impressive activity and purity data for GM-CSF (FIG. 6A), IL-4 (FIG. 6B), somatotrophin (FIG. 6C), TGF-β1 (FIG. 6D), VEGF-165 (FIG. 6E), TNF-α (FIG. 6F), M-CSF (FIG. 6G), IL-6 (FIG. 6H, EPO (FIG. 6I), IL-2 (FIG. 6J), SCF (FIG. 6K), Noggin (FIG. 6L), and G-CSF (FIG. 6M).
Figure 6F:
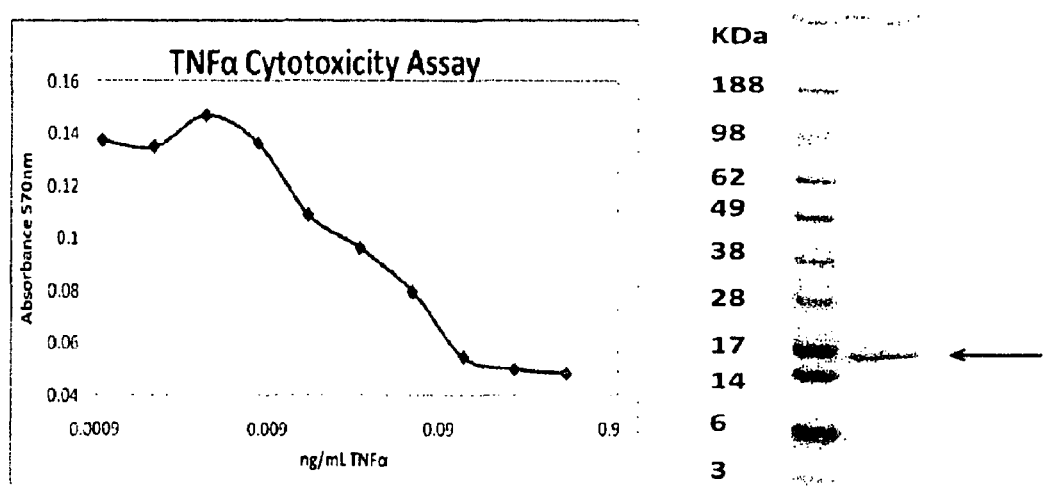
Figure 6G:
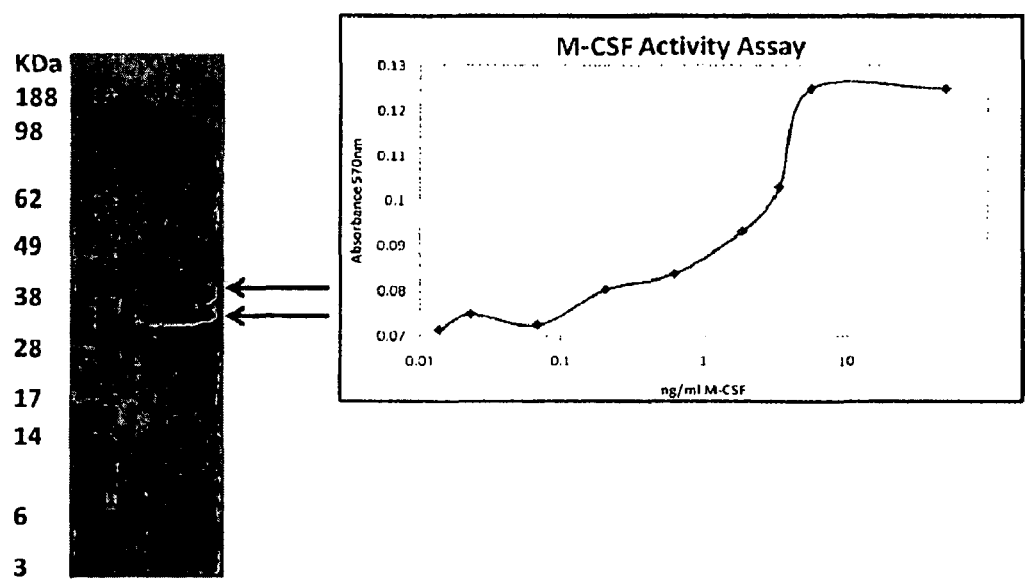
Figure 6I:
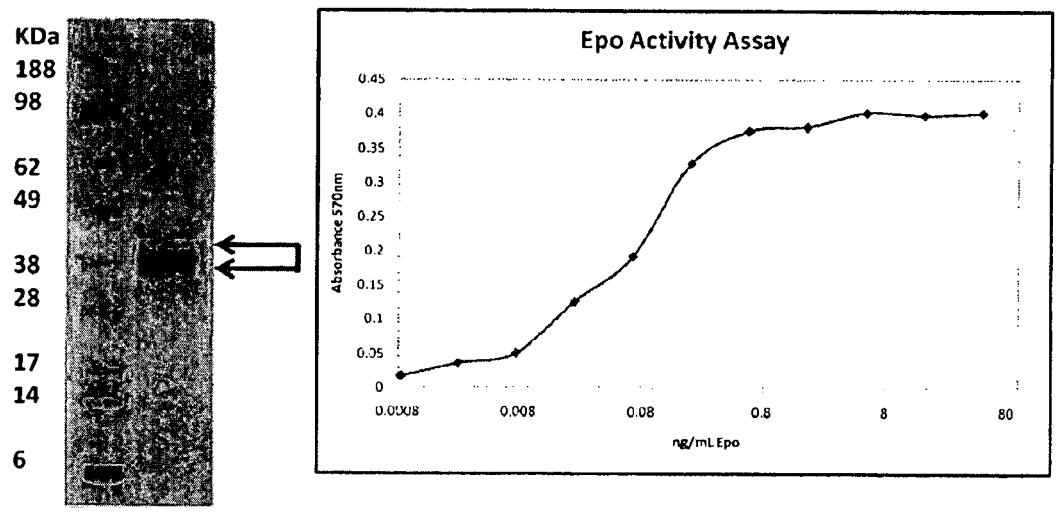
Figure 6J:
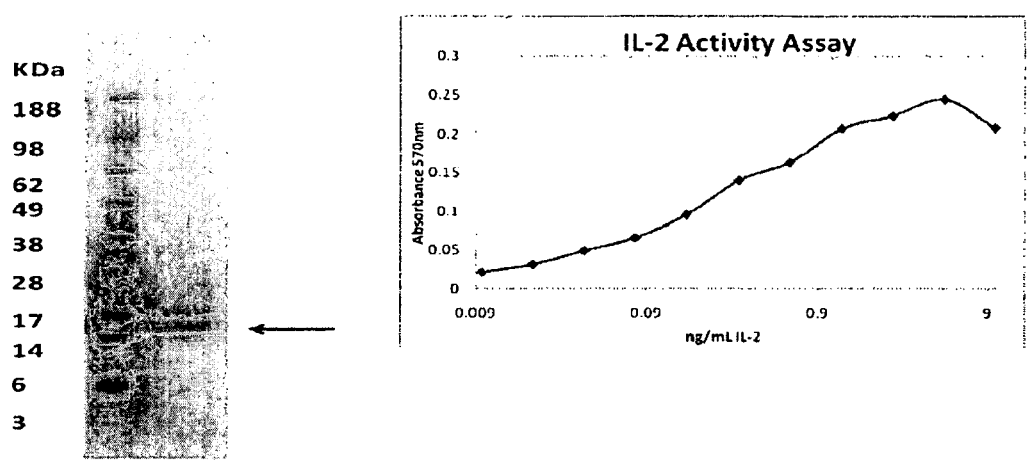
Figure 6K:
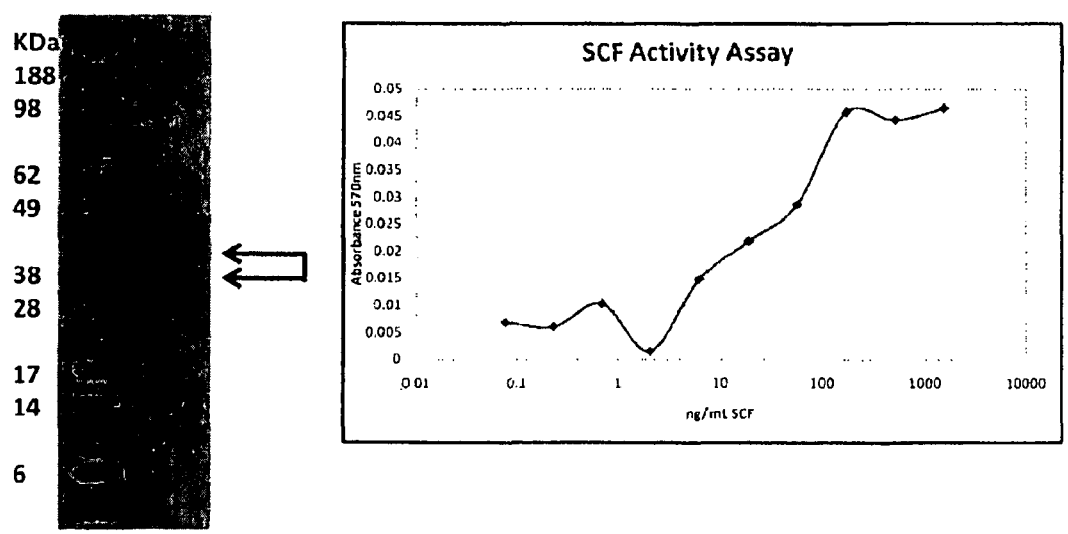
Figure 6L:
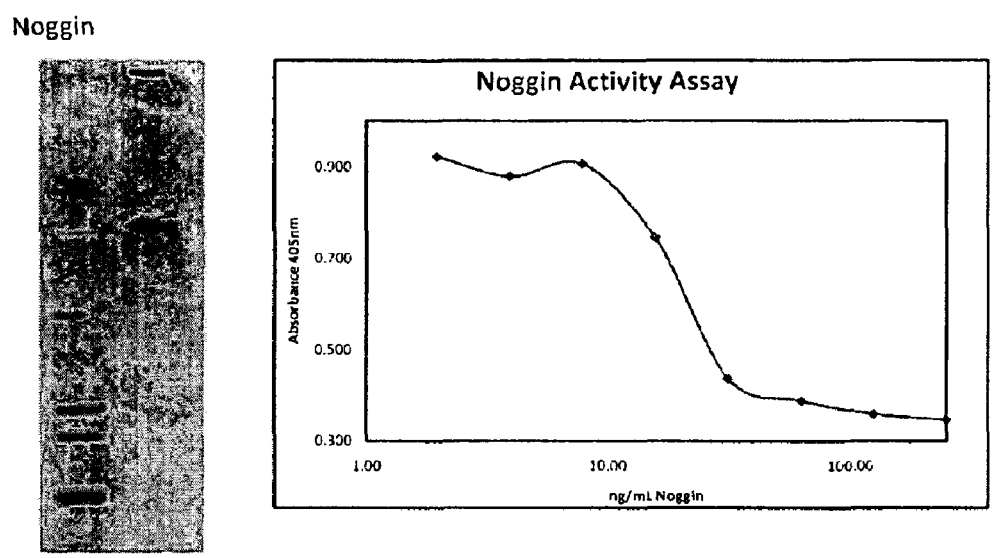
Figure 6M:
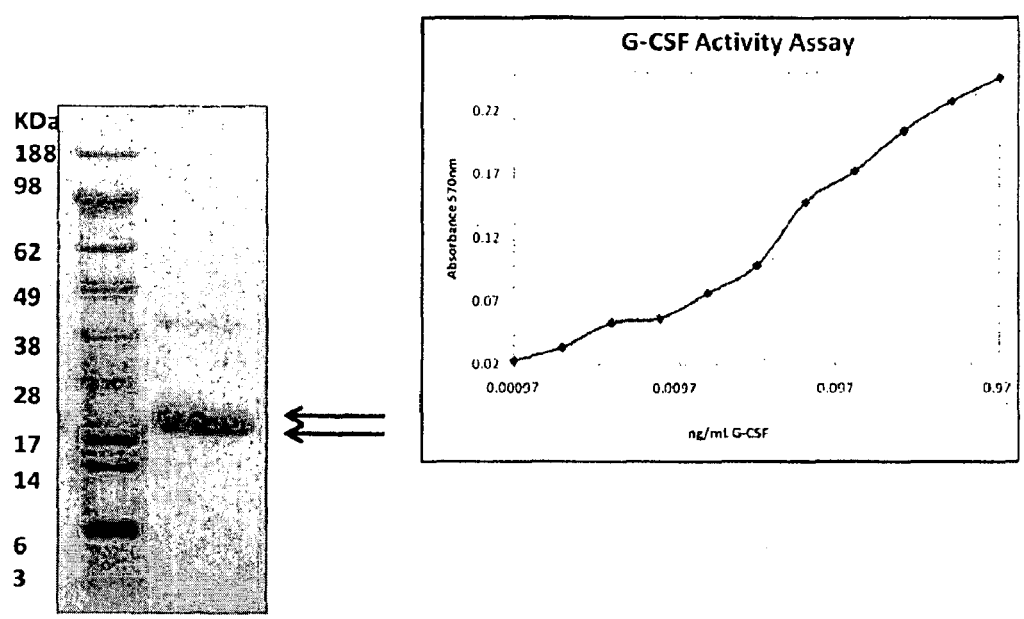

Furthermore, because the surfaces of the recombinantly-expressed protein are more similar to the native surfaces, it possesses more authentic surface epitopes that are ideal for producing high-affinity antibodies. Such high-affinity antibodies therefore are very useful in therapy, diagnostics, and Research & Development studies. Since they have been raised against authentic recombinantly-expressed proteins and are therefore can recognize the endogenous, naturally-expressed counterpart proteins more specifically, a smaller quantity of antibody may be administered to an individual or used in an in vitro method. For that reason, a fraction of the dosage of a particular antibody raised against an authentic protein of the present invention may be used to accomplish a treatment that otherwise requires a much more concentrated dose, as explained in detail elsewhere herein. Not only does the use of lower concentrations of such antibodies mean that the frequency of dosage may be reduced, but also that the incidence of side effects can also be reduced or eliminated entirely. Furthermore, the present human cell line, methods, and compositions make it possible to express human proteins, especially certain cytokines such as TGFβ1, that have hitherto been notoriously difficult, if not impossible, to express in such other non-human cells. See the Examples and FIG. 5, which evidence production of TGFβ1, for instance, using the present inventive method.

As explained herein, the human cell cultures of the present invention are stable. See "Methodology" below and the Examples. That is, the same culture of cells can be used repeatedly to express and subsequently secrete into the supernatant any desired human protein, such as a human cytokine. The human cells are stable because they have been selected for their ability to grow in serum-free media using antibiotic selection techniques. The significance of this is many-fold: the same volume of human cells can be sustained for long periods of time unlike in existing systems which are unable to be replenished. This means that the human cells of a spun-down aliquot of the culture can be returned to the stock culture and allowed to re-proliferate.

By contrast, because the human cell systems of the prior art are not stable, a volume of culture represents only a one-time opportunity to harvest the expressed proteins. That is, once the cells have been lysed or collected by centrifugation to isolate the protein-containing supernatant, the human cells of the prior art are for all intents and purposes dead and unusable. Accordingly, the re-usability of the present human cells is highly appealing.

Not only does this mean that the same volume of cells can be reused time and again, but that the inventive method is adaptable to large-scale processing. Since the stability of the human cells is established early on, then the human cells are able to survive in any volume of culture medium. See FIG. 1. For instance, it is possible to maintain a viable culture of human cells in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 liters, or more than 50 liters of culture, or any integer in between. Accordingly, the present inventive method allows for commercial scale production of recombinant proteins, such as recombinantly-expressed cytokines, at yields that are commercially desirable.

Figure 2:
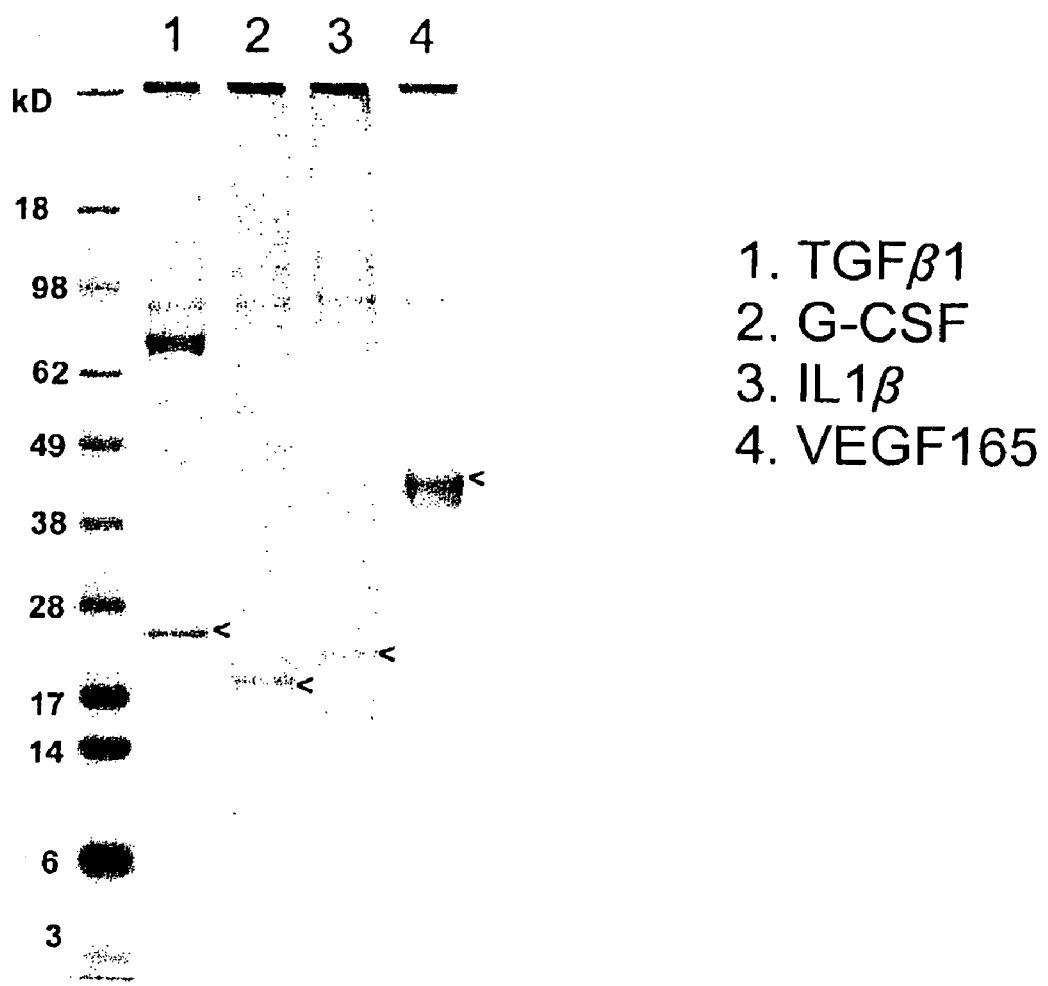
FIG. 2: SDS-PAGE gel showing high expression of cytokines in the inventive stable human cell lines for expression of TGFβ1 (lane 1), G-CSF (lane 2), IL1β (lane 3), and VEGF165 (lane 4).

Thus, the present inventive human cell expression system lends itself to scalability, and thereby to producing increased yields of an authentically-produced protein per unit time. See FIG. 2. Because the cell culture uses serum-free media, the resultant supernatant contains essentially only the secreted expressed recombinant protein. Consequently, the purity of the end product, i.e., of the recombinantly-expressed protein, is very high. Consequently, the concentration and bioactivity of the isolated expressed protein are high and the possibility of contamination with cellular debris and other non-desirable proteins is low.

The purity of the expressed human cytokine and the supernatant into which it is secreted also are important factors in establishing accurate and authentic biological activity and for ensuring that antibodies that are raised against it are also highly specific with high binding affinities in and of themselves. The use of serum-free media therefore for growing a stable human cell culture is very helpful in this regard because there is little, if any, contaminating protein or cell debris in the expressed cytokine eluate or supernatant.

Figure 3:
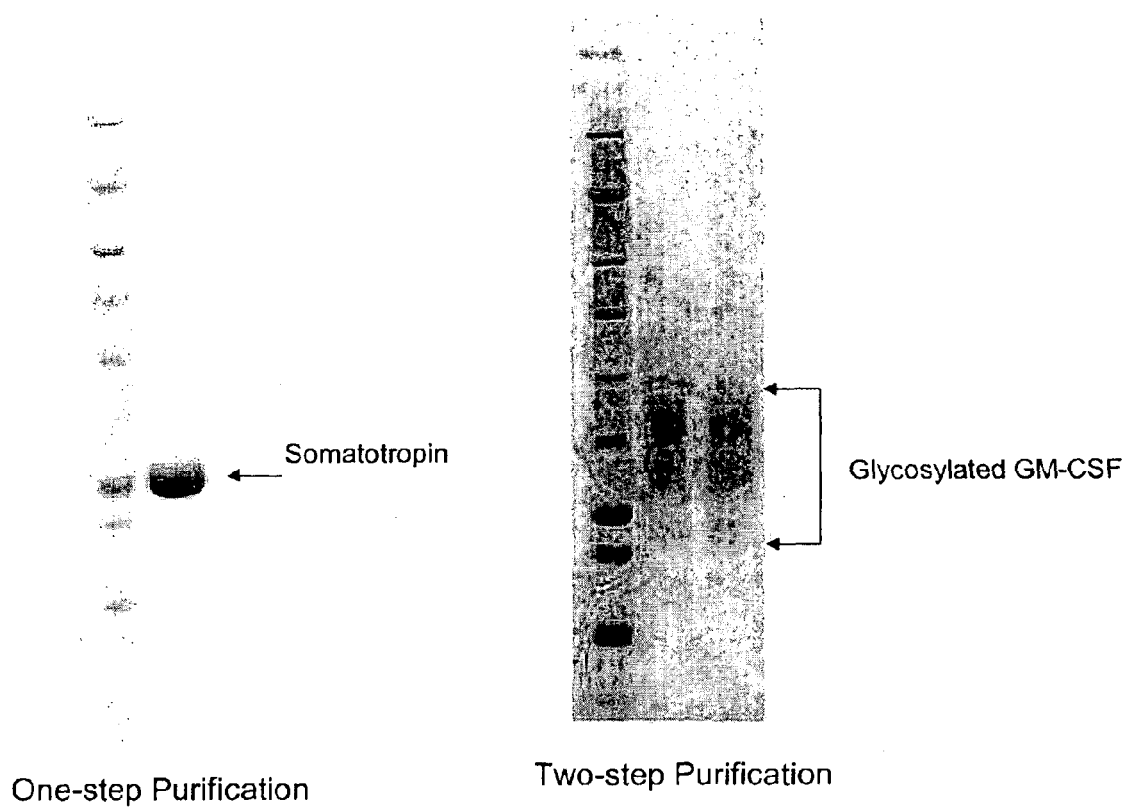
FIG. 3: SDS-PAGE gel showing efficient tag-free purification for somatotropin and GM-CSF.

Along the same lines, because the recombinant protein is secreted from the human cells and into serum-free media, it is relatively straightforward to therefore isolate the expressed and secreted protein. That is, it is not necessary to employ a "His-Tag" isolation scheme to isolate the expressed protein from the supernatant. See FIG. 3. A His-tag is typically a stretch of six histidine amino acid residues which are engineered into the expression cassette so that the expressed protein is a fusion including the six residues, which can subsequently become bound to partnering residues that are coated in the inside of a column. Accordingly, because it is unnecessary to use such a tag to isolate the expressed proteins of the present invention, an additional step toward producing the authentic human protein is eliminated.

Thus, the inventive method is scalable to commercial levels, employs a re-usable, self-perpetuating human cell culture suspended in serum-free media, which eliminates contamination and increases purity yields of the expressed recombinant protein. That resultant recombinant protein is highly authentic with respect to its folding and glycosylation state such that the recombinantly-expressed authentic protein is highly similar to its endogenous, native counterpart.

2. Methodology (a) Preparation of Human Cells

Human cells are plated onto a Petri dish as a monolayer on serum-free medium. The cells that survive on the serum-free medium are then placed into serum-containing medium to produce a working cell bank. Serum-free media includes, but is not limited to 293 SFM II, CD 293, FreeStyle 293, Hybridoma-SFM (Invitrogen), and Ex-Cell 293 (JRH Biosciences).

(b) Transfection

An appropriate concentration of plasmid DNA and transfectant is added to a Petri dish containing a confluent layer of cells. Useful transfectants include, but are not limited to FuGene 6, FuGene HD (from Roche); Lipofectamin, Lipofectamin 2000, 293fectin (Invitrogen), and Polyethylene-imine. The plasmid DNA is engineered to comprise an antibiotic resistance gene to aid in the selection of appropriately transfected human cells. See the sections which follow below.

(c) Selection of transfected cells after exposure to antibiotics

The transfected cells of step (b) are harvested by centrifugation after trypsin treatment (which detaches cells from the Petri dish plate), and then resuspended in serum medium that contains a certain concentration of antibiotics, e.g., 400 ug/ml or 800 ug/ml, of an antibiotic such as neomycine (G418), hygromycine, zeocin, or blasticidine, for a period of time. Surviving cell colonies can then be harvested and exposed to another round of antibiotics for another period of time.

(d) Cell Adaptation

The cells that survive antibiotic treatment are then resuspended in serum-low medium that includes, for instance, 1% serum, and antibiotics, to determine which cells are stable enough to maintain viability and growth in liquid culture.

This "adaptation" period can take a few weeks, after which time the cells are transferred to serum-free medium that contains only antibiotics, and again left to "adapt" for a period of time.

Such a suspension of adapted cells therefore represents a stable culture of human cells that can withstand the rigors of transfection and antibiotic selection. Furthermore, those cells can be continuously grown and used to inoculate larger volumes of culture or also can be cryo-banked in fresh medium for future inoculations of culture.

(e) Producing cytokines from suspended, antibiotic-resistant human cells

The plasmid DNA expresses a cytokine gene or encoding polynucleotide that is secreted from the antibiotic-resistant human cells that are continuously growing in the large volume culture suspension of (d). Aliquots of that large suspension can therefore be centrifuged gently to pellet the human cells and separate the supernatant which will contain the desired cytokine. Since the suspension medium in which the human cells are growing is serum-free, or protein-free, there is little, if any, contaminating cellular material, such as other proteins or cellular debris. Accordingly, the supernatant that contains the secreted cytokine is relatively pure.

The human cell pellet can then be resuspended and reintroduced into the same or different suspension or media to restart the expression process. Thus, the whole system is repeatable and not, unlike prior art expression systems, a one-time usable suspension of cells.

(f) Yield

The yield of protein that can be produced by the present inventive method can depend on the volume of human cell culture used to express the desired polynucleotide construct, the cytokine and its size, and the constituent base of the culture medium itself. Yield can be affected by changing certain components of the culture medium, temperature, pH, or by including glycan precursors in the mix to facilitate glycosylation mechanisms. The yield of expressed human cytokine therefore from the human cell expression system of the present invention can be from 1-500 mg/liter, or more than 500 mg/liter. Accordingly, the present invention contemplates yields of cytokines from the human cell expression system of the present invention of about 1 mg/liter, about 2 mg/liter, about 3 mg/liter, about 4 mg/liter, about 5 mg/liter, about 6 mg/liter, about 7 mg/liter, about 8 mg/liter, about 9 mg/liter, about 10 mg/liter, about 20 mg/liter, about 30 mg/liter, about 40 mg/liter, about 50 mg/liter, about 60 mg/liter, about 70 mg/liter, about 80 mg/liter, about 90 mg/liter, about 100 mg/liter, about 120 mg/liter, about 140 mg/liter, about 160 mg/liter, about 180 mg/liter, about 200 mg/liter, about 220 mg/liter, about 240 mg/liter, about 260 mg/liter, about 280 mg/liter, about 300 mg/liter, about 320 mg/liter, about 340 mg/liter, about 360 mg/liter, about 380 mg/liter, about 400 mg/liter, about 420 mg/liter, about 440 mg/liter, about 460 mg/liter, about 480 mg/liter, or about 500 mg/liter or more than about 500 mg/liter. The invention also contemplates yields between any of these concentrations.

Thus, a yield of the present invention may be between about 10-50 mg/liter, or between about 50-100 mg/liter, or between about 100-150 mg/liter, or between about 150-200 mg/liter, or between about 200-250 mg/liter, or between about 250-300 mg/liter, or between about 300-350 mg/liter, or between about 350-400 mg/liter, or between about 400-450 mg/liter, or between about 450-500 mg/liter, or between about 500-550 mg/liter, or between about 550-600 mg/liter, or between about 600-650 mg/liter, or between about 650-700 mg/liter, or between about 700-750 mg/liter, or between about 750-800 mg/liter, or between about 800-850 mg/liter, or between about 850-900 mg/liter, or between about 900-950 mg/liter, or between about 950-1,000 mg/liter.

In other words, a yield of recombinant-produced, authentic proteins of the present invention made according to the methods disclosed herein may be 2-fold, 3-fold, 4-fold, 5-fold, 6-fold, 7-fold, 8-fold, 9-fold, or 10-fold greater than the yield obtained from other cell expression systems.

3. Vector Design

An aspect of the present invention is a novel expression cassette that comprises (1) a cytomegalovirus enhancer element, such as the CMV immediate early enhancer element (CMV IE);

(2) a human promoter sequence selected from the group consisting of (i) a human actin promoter, (ii) a human serum albumin promoter, and (iii) a human fibrinogen promoter.

(3) a human globin gene intron; and (4) a signal peptide, such as immunoglobulin superfamily 8 signal peptide or an alpha-fibrinogen signal peptide.

The expression vector may also comprise a nucleic acid sequence of interest or a desired polynucleotide operably linked to the above-described elements (1)-(4), positioned downstream of the signal peptide, so that it can be subsequently expressed in a cell.

A desired polynucleotide sequence may be one that encodes a desired cytokine or cytokine fragment. The expression cassette also may comprise a sequence for an antibiotic resistance gene, which may be cloned between the regulatory elements used to express the cytokine polynucleotide, or which may be operably linked to its own promoter and terminator independently from the expression cassette that is used to express the cytokine-signal peptide fusion protein.

Thus, expression vectors of the present invention include, for instance, the following:

1. pHZhag comprising operably linked nucleotide sequences for (i) an hCMV IE, (ii) a human beta-actin promoter, and (iii) a human beta-globin intron;

2. pHZA comprising operably linked nucleotide sequences for (i) an hCMV promoter, and (ii) a human fibrinogen subunit A signal peptide;

3. pHZI comprising operably linked nucleotide sequences for (i) an hCMV promoter, and (ii) a human Ig superfamily 8 signal peptide;

4. pHZhagA comprising operably linked nucleotide sequences for (i) an hCMV IE, (ii) a human beta-actin promoter, (iii) a human beta-globin intron, and (iv) a human fibrinogen subunit A signal peptide;

5. pHZhagI comprising operably linked nucleotide sequences for (i) an hCMV IE, (ii) a human beta-actin promoter, (iii) a human beta-globin intron, and (iv) a human Ig superfamily 8 signal peptide;

6. pHZhag-TGFβ1 comprising operably linked nucleotide sequences for (i) an hCMV IE, (ii) a human beta-actin promoter, (iii) a human beta-globin intron, and (iv) TGFβ1; and 7. phZhagI-TGFβ1 comprising operably linked nucleotide sequences for (i) an hCMV IE, (ii) a human beta-actin promoter, (iii) a human beta-globin intron, (iv) a human Ig superfamily 8 signal peptide, and (v) TGFβ1.

Control expression cassettes include:

1. pCAG comprising operably linked nucleotide sequences for (i) hCMV IE, (ii) chicken beta-actin promoter, and (iii) rabbit beta-globin intron; and 2. pHZsec comprising operably linked nucleotide sequences for (i) hCMV promoter, and (ii) mIg-kappa leader.

(a) Cloning

Cloning of cytokines can be accomplished by various methods available to one skilled in the art of genetic engineering. For example, total RNA or poly-A RNA can be purified from human tissues samples abundant in particular cytokine expression (for example lymphocytes) and used as a template for gene specific RT-PCR. Additionally, pre-made cDNA libraries can be purchased from commercial sources and PCR can be employed to amplify the cytokine cDNA directly. Still further, synthetic oligonucleotides can be constructed to create a synthetic gene for the cytokine based on sequence information available in National Center for Biotechnology Information with their gene accession numbers. Additionally, full length cDNA clones can be obtained from, for example, the IMAGE clone consortium (image.IInI.gov/) or Openbiosystems (Huntsville, Ala.). The full length cytokine cDNA clones were obtained from Openbiosystems (Huntsville, Ala.). Gene accession numbers of cloned cytokines are presented in Table 3.

A cytokine typically has a signal peptide at its N-terminal which can be identified by numerous tools available to one skilled in the art; for example using Swiss-Prot protein knowledgebase. Some cytokines have variants due to different transcription that can be also identified by the available tools. Sequences of the secreted cytokines are listed in Subsection 10 above. To facilitate rapid cloning of cytokines with different signal peptides, it is possible to engineer an expression cassette so that the expressed cytokine contains a signal peptide. For instance, pSecTag2c (Invitrogen, Carlsbad Calif.), which is suitable for the production of secreted recombinant protein in mammalian cells (for example, CHO and HEK293), can be engineered into a vector of the present invention by site directed mutagenesis using appropriate cloning and restriction digest strategies to integrate the DNA encoding the signal peptide in the correct reading frame orientation so that it is properly transcribed and translated along with the co-joined cytokine sequence. For instance, it is possible to introduce a Srf I restriction site in frame with the Igκ leader sequence (see FIG. 27) using mutagenesis primers SecTag2c-srflf (TCCACTGGTGACGCGCCCGGGCCG-GCCAGGCGCGCC) (SEQ. ID. NO 34) and SecTag2c-srflr (GGGGCGCCTGGCCGGCCCGGGCGCGT-CACCAGTGGA) (SEQ. ID. NO: 35).

4. Human Cells

The types of human cells that can be used to express a protein of the present invention includes human stem cells, human precursor cells, human kidney cells, human retina-derived PER-C6 cell, a human embryonal kidney cell line. Particularly useful human cell lines include but are not limited to HEK 293 cells and derivatives thereforeof, such as HEK 293T, HEK 293S, and HEK 293 EBNA.

In particular the present invention provides a novel human cell line denoted as HZ-293TS, which was adapted herein to serum-free and chemically-defined media. See Example 2. The cell line named HZ-293TS is deposited under and bears the ATCC biological deposit accession number of PTA-10165, deposited on Jul. 1, 2009.

5. Products (a) Cytokines

According to the present inventive methods, it is possible to conduct medium and large scale production of human cytokines from human cells. The inventive method has been successful in producing more than 60 tag-free cytokines, including difficult-to-express proteins of the TGF-β superfamily. Using GM-CSF, IL4 and VEGF165 as examples, for instance, it is demonstrated herein that highly-authentic glycosylated cytokines can be expressed and isolated from human cells and used as highly preferred reagents for subsequent development of treatments of inflammation, cancer, stem cell research, and raising of antibodies. Furthermore, not only are the human cytokines that are produced by the present inventive technology more natively glycosylated but the appropriate disulfide bonds that are sometimes necessary to create a fully functional complex are also intact. This is unlike the situation in certain non-human cells, where disulphide bonding between expressed monomers is not possible.

Being able to produce highly authentic human proteins without the use fo purification- or isolation-required tags, such as histamine-tags is a highly desirable feature of the present invention. The present inventive method and vector system permit the expression of human proteins that are highly authentic in terms of their structural, biochemical, and functional identities to their native, endogenous human versions; meaning that the polynucleotides that encode the authentic protein sequences of the present invention do not necessarily require the incorporation of histidine-encoding residues to aid in purification and isolation of the subsequently expressed protein. Thus, an aspect of the present invention is a method for recombinantly producing authentic human proteins without the use of peptidic tags, and the authentic proteins themselves which are "tag-free." Hence, one aspect of an "authentic" protein of the present invention is that it is tag-free. However, this is not meant to exclude the possible use of tags, such as his-tags in conjunction with the present inventive methods and vectors. That is, the present invention also encompasses the recombinant production of an authentic protein in which a tag, such as a his-tag, is incorporated as a fusion protein to the N- or C-terminus of the authentic protein to aid in its identification, purification, and isolation.

It is highly desirable to express the following cytokines in the stabilized human cell expression system of the present invention: Activin A, Activin B, Activin A/2xINHbA, Activin B/2xINHbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2B, IFN-γ, ß1IFN-β$_1$, IGF I, IGF II, IGF IIv1, IGF IIv2, IL10, IL11, IL12, IL15, IL17/IL17A, IL17F, β IL1 β1 IL2, IL23, IL27, IL28A/IFN-lambda-2, IL28B/IFN-lambda-3, IL29/IFN-lambda-1, IL1β, IL2 IL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFα, PDGFβ, Persephin, SCF, SDF1α, SHH, Somatotropin, TGF β1, TGF β2, TGF β3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14. See also the "List of Cloned Cytokine Genes" at Table 5. See also the list of cytokines listed in Table 5. Any of those cytokines may be expressed in the human cell expression system of the present invention too.

The Examples below and the corresponding figures demonstrate successful expression of highly pure, authentically-glycosylated bioactive cytokines, namely EPO, G-CSF, GM-CSF, IL-2, IL-4, IL-6, M-CSF, Noggin, SCF, Somatotropin, TGFβ1, TNFα, and VEGF-165. See FIGS. 6A-M, 7A-D, and 8A-C for graphical and gel data evidencing recombinant expression of these cytokines and their respective bioactivities and comparisons against cytokines expressed from other cell systems.

(b) Antibodies

Another benefit attributable to authentically glycosylated, folded, and phosphorylated proteins of the present invention is that they are excellent reagents for raising highly specific antibodies.

Monoclonal antibodies are useful for assaying for the presence of a particular cytokine or for isolation and purification of the proteins to which they specifically bind. Accordingly, monoclonal antibodies are useful for diagnostic assays, detection assays, and purification protocols. Because the recombinant cytokines produced by the present inventive human expression system are more authentically glycosylated and folded than had they been expressed in non-human cells, any antibodies that are raised against them will have a higher affinity toward endogenous cytokines in the human body or in a human biological sample.

Monoclonal antibodies can be made according to known methods using recombinant human interferon(s) used as specific antigen(s). One or more antigens can be injected at one time. For instance by using interferons made from *E. coli*, and from interferons made from transfected according to previous methods described in this invention using transfected human cell producing the identical interferon(s). Cross board analytic testing of several of the clones producing antibodies selected from recombinant interferons made from *E. coli* when compared to antibodies selected from clones immunized with authentic recombinant human interferon, made from transfected human cells. It also is possible to obtain a cell line which is able to produce monoclonal antibodies by fusing mouse myeloma cells to spleen cells followed by subsequent selection of clones capable of producing the desired antibody. See Köhler & Milstein, Nature (1975), 256 (5517): 495-497; and Köhler et al., Eur J. Immunol. (1976), 6:292-295. Panels of monoclonal antibodies produced against epitopes can be screened for various properties; i.e., for isotype and epitope affinity. An alternative technique involves screening phage display libraries where, for example the phage express scFv fragments on the surface of their coat with a large variety of complementarity determining regions (CDRs). This technique is well known in the art.

Polyclonal antibodies using antigens made from the secretion of glycosylated recombinant human cytokines can produce antibodies that besides recognizing the protein part of the molecule, also recognizing the glycosylated part of the particular recombinant human interferon. Polyclonal antibodies may be raised by immunizing various species of animals, such as rabbits, goats, sheep, or other animals, by immunizing the animals with the authentic recombinant human interferon, made using the method encompassed in this invention by repeated injections of microgram to mg amounts of one of these interferons as antigen, often together with Freunds Incomplete adjuvant. Examples of polyclonal antibodies ("pAbs") encompassed by the present invention include, but are not limited to, pABs for EPO, FLt3, G-CSF, GM-CSF, M-CSF, IFN-α2A, IL-4, and IL-6.

As used herein, an "antibody" refers to a protein consisting of one or more polypeptides substantially encoded by immunoglobulin genes or fragments of immunoglobulin genes. Antibodies may exist as intact immunoglobulins or as a number of fragments, including those well-characterised fragments produced by digestion with various peptidases. While various antibody fragments are defined in terms of the digestion of an intact antibody, one of skill will appreciate that antibody fragments may be synthesised de novo either chemically or by utilising recombinant DNA methodology. Thus, the term antibody, as used herein also includes antibody fragments either produced by the modification of whole antibodies or synthesised de novo using recombinant DNA methodologies. Antibody fragments encompassed by the use of the term "antibodies" include, but are not limited to, Fab, Fab', F(ab')2, scFv, Fv, dsFv diabody, and Fd fragments. Furthermore, the antibodies and fragments thereof may be humanised antibodies, for example as described in EP-A-239400, which is incorporated herein by reference.

Examples of antibodies prepared according to the present invention include polyclonal antibodies raised against recombinantly-produced, authentic human IL-2, IL-4, IL-6, EPO, G-CSF, GM-CSF, M-CSF, FLT3L, and IFN-α2A. Monoclonal antibodies that are being made include, but are not limited to, monoclonal antibodies against recombinantly-produced, authentic human IL-2, IL-4, IL-6, EPO, G-CSF, TGF-β1, IFN-α, and IL-17.

(c) Kinases

It is also highly desirable to express the following human kinase genes in the stabilized human cell expression system of the present invention so as to obtain recombinantly-produced, authentic human kinases, including but not limited to: AKT1, AKT2, AMPK1, ATM, Aurora A, BTK3, CDK6, ERK5, Fyn-1, GRK5, JNK1, LYN, MAPKAPK2, MAPKAPK3, MEKK3, MKK3, MKK4, mTOR, P38-α, P70S6K2, PDK1, PKC-β, PKC-γ, PTEN, SYK, and Zap70.

(d) Other Proteins

The present invention is not limited to producing only cytokines and antibodies raised against those cytokines. Other human proteins can be expressed according to the present invention using the inventive stable human cell line, including, but not limited to kinases and other enzymes. Thus, the present invention also encompasses the recombinant production of authentic human plasma proteins selected from the group consisting of albumin, IgG, IgA, IgM, IgD, IgE, alpha-1-proteinase inhibitors, blood pro-coagulation proteins, blood anti-coagulation proteins, thrombolytic agents, anti-angiogenic proteins, alpha.-2-antiplasmins, C-1 esterase inhibitors, apolipoproteins, HDL, LDL, Fibronectin, beta-2-glycoprotein I, fibrinogens, plasminogens, plasmin, plasminogen activators, plasminogen inhibitors, plasma protease inhibitors, anti-thrombin III, streptokinases, inter-alpha-trypsin inhibitors, alpha.-2-macroglobulin, amyloid protein, ferritins, pre-albumin, GC-globulin, haemopexin, C3-complement, transferrin, urokinase, alpha.-1-acid-glycoprotein, coagulation, anti-coagulation factor(s) (such as Factor II, Factor V, Factor VII, Factor VIII, von Willebrand factor, Factor VIII—von Willebrand factor complex, Factor IX, Factor X, Factor XI, Cl inhibitor, protein C and Protein S), extracellular membrane proteins, or extracellular domains of receptors.

7. Purification

Purification of the authentic-like recombinant is tailor made to the expression of cells, and human cells such as HEK cells, and other related human cells after having expanded the necessary amount of the targeted interferon genes in coli bacteria culture. The cells used for the particular interferons are chosen and is tailor made to the particular vector, where one has chosen the correct human-component originated promoter. The particular human cell selected for individual interferons necessitates thorough selection of the optimal human cell line(s). Due to the fact that the cells are adapted to cell suspension culture serum-free medium, purification methods applied to the harvested medium are easier to design when compared to serum containing cell culture medium.

For instance, the supernatant of the serum-free medium can be collected by centrifugation and the cell pellet resuspended in fresh serum-free medium for further production of the cytokine. Expression of cytokines can be readily identified on SDS-PAGE gel analysis using Coomassie stain by known molecular weight or via traditional Western blot analysis. To capture the cytokine, the supernatant was at first loaded on an immobilized metal affinity chromatography (IMAC) column. Based on their properties some cytokines were bound on IMAC column while some were found in flow through. As next purification step cytokine fraction pool was loaded on an ion exchange chromatography (IEX) column after buffer exchange to a proper buffer condition. Finally as polishing step cytokine fraction pool was loaded on another IEX or different affinity chromatography (for example Heparin resin) column.

(b) Purity (i) Cytokine Purity Levels

Figure 7:
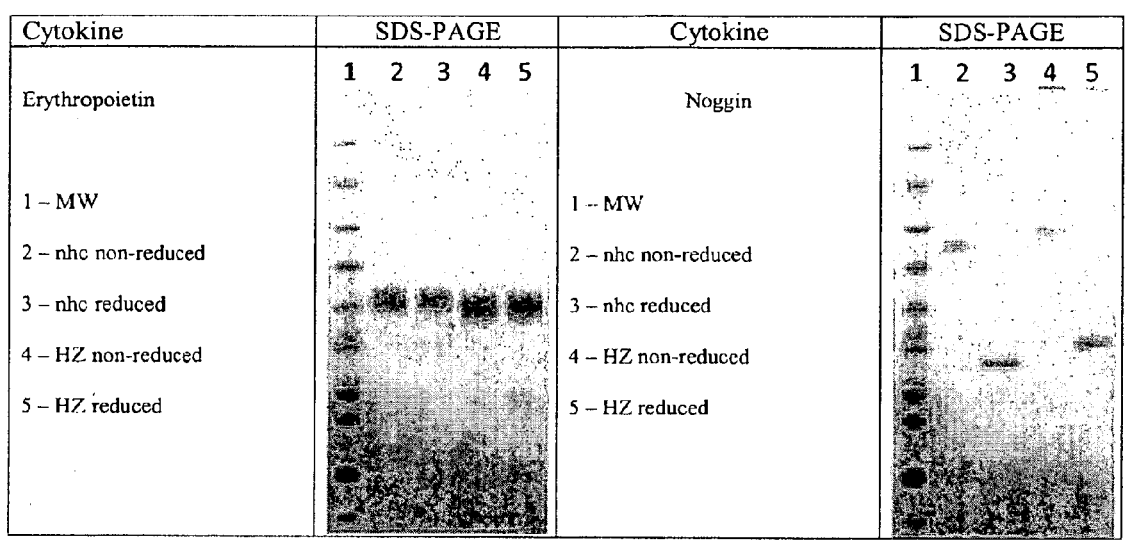
FIG. 7: SDS-PAGE gel analyses of purified cytokines from the inventive human cell system compared with cytokines from non-human cell system: (A) EPO, Noggin; (B) G-CSF, SCF, GM-SCF, Somatotropin; (C) IL-2, TGF-β1, IL-4, and TNFα; and (D) 1L6, VEGF165, and M-CSF.
Figure 7:
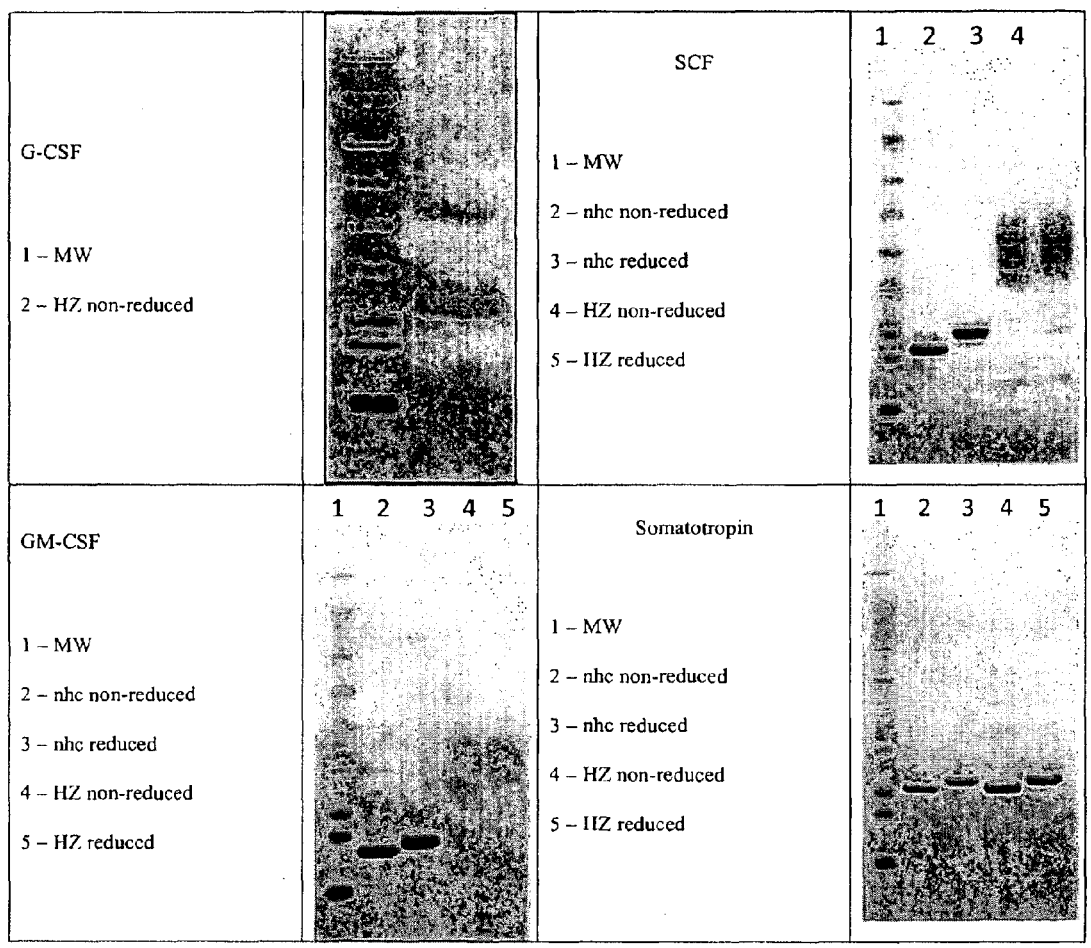
Figure 7:
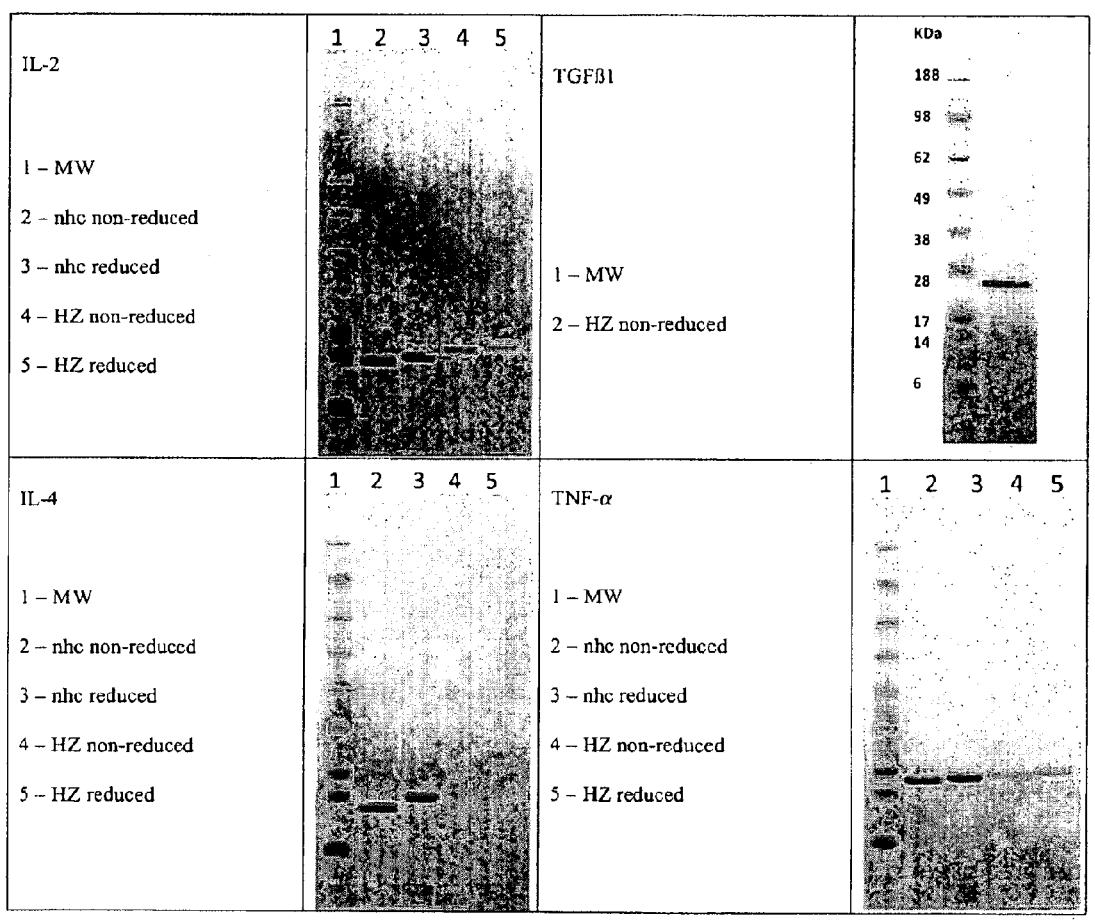
Figure 7:
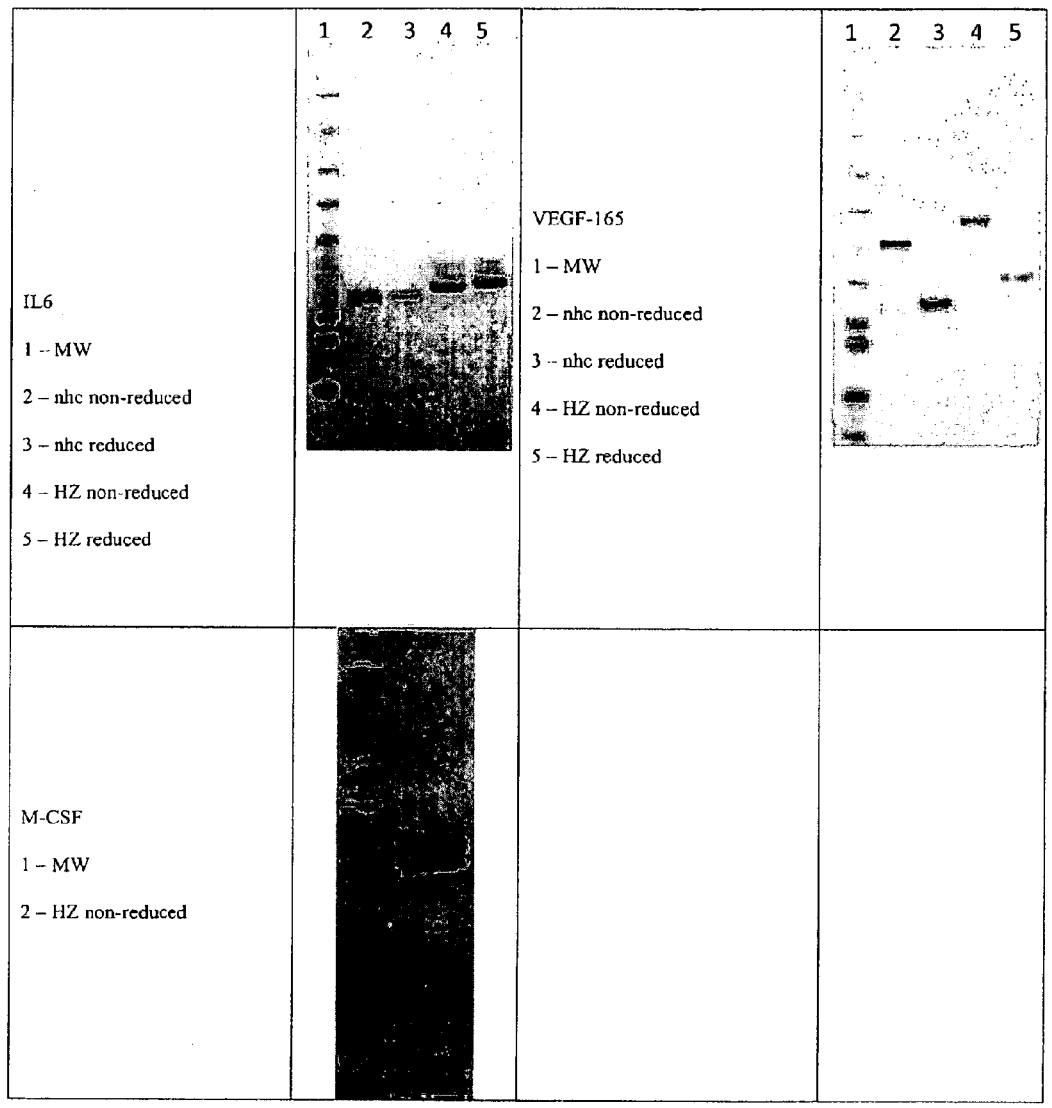
Figure 8:
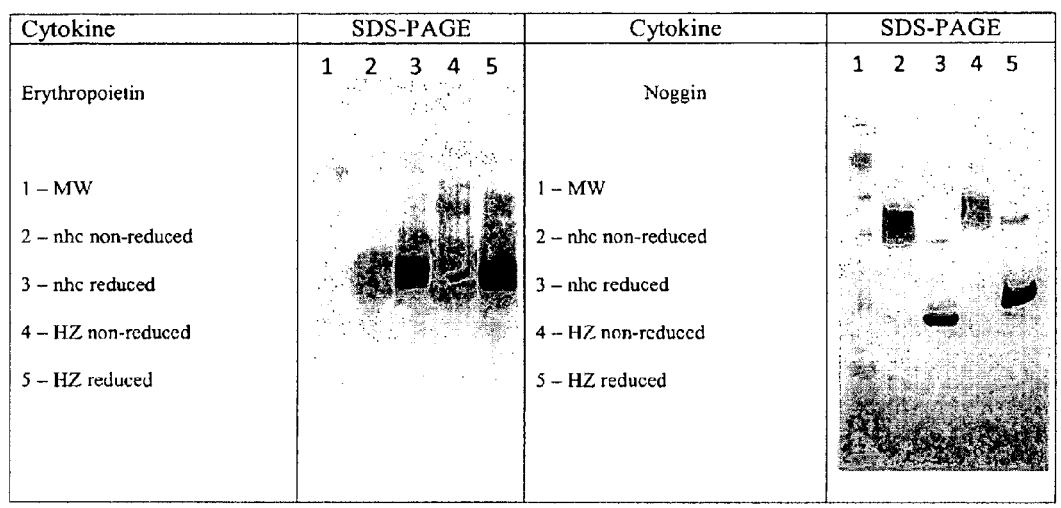
FIG. 8: Western blot on purified cytokines from the inventive human cell system compared with cytokines from non-human cell system: (A) EPO, Noggin; (B) GM-CSF, SCF, IL-2, Somatotropin; (C) IL4, TNFα, IL6, and VEGF165.
Figure 8B:
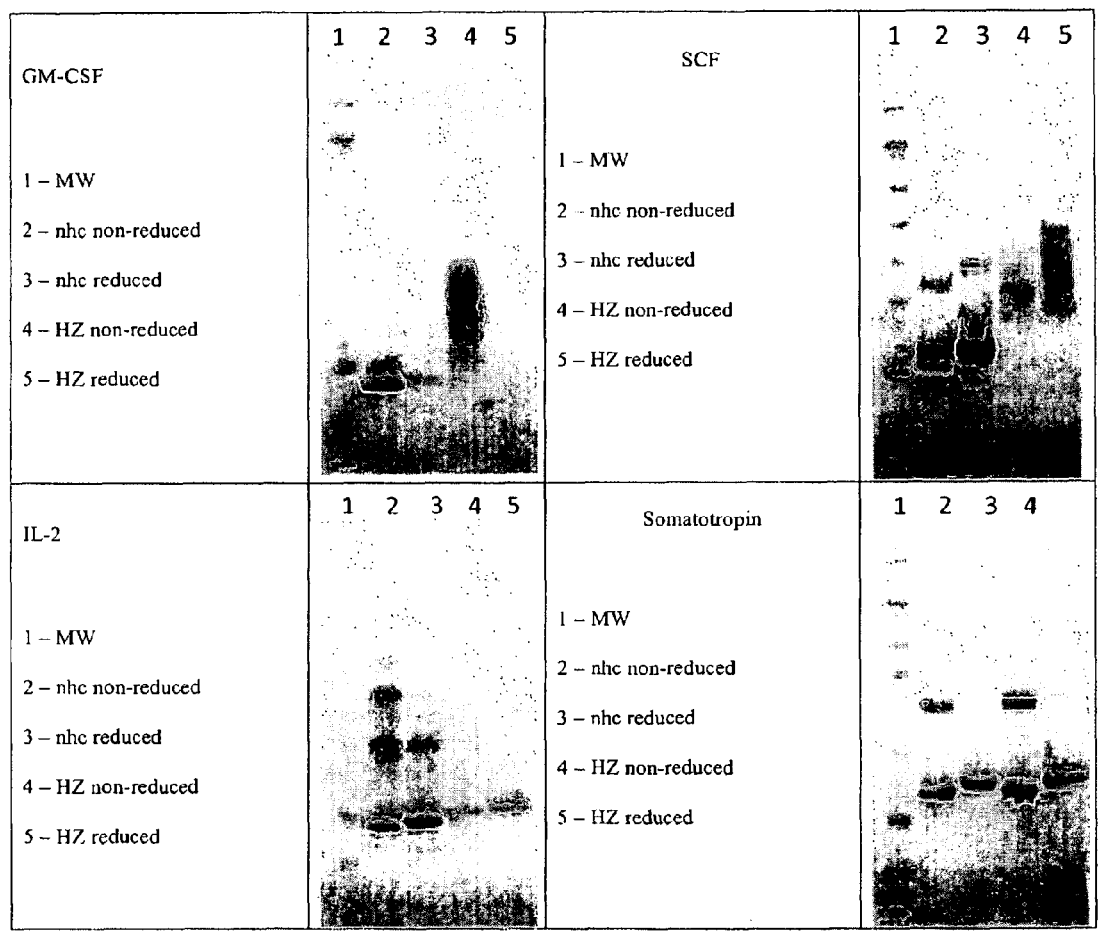

After up to three chromatography steps cytokines were more than 95% pure judged by Coomassie stain on SDS-PAGE gel (FIG. 7) and by Western blot with available antibodies (FIG. 8). Pure cytokines then were quantified using known methods available to one skilled in the art (for example Bradford assay, Coomassie stain on the gel, and OD280 nm). After the quantification cytokines were analyzed endotoxin level by endotoxin detection kit from Lonza (Allendale, N.J.) according to manufacturer's manual, aliquoted based on required amounts and lyophilized for commercialization.

(ii) Low Contaminants

Endotoxins are frequent contaminants in the cytokines prepared from bacterial and other expression systems. Even low levels of endotoxins can be toxic to cells or organisms and must be removed. The industry standard reported value for commercially supplied cytokines is <1.0 EU/µg. The present inventive methods are able to produce proteins, such as various different human cytokines, with ultra-low levels of endotoxin contamination. Cytokines, as disclosed below, have been prepared according to the present invention which yield ten times to one thousand times less endotoxin than the levels reported in standard commercial preparations.

8. Assays

Many different assay systems are available for ascertaining cytokine "purity," "activity" and for quantifying concentrations of cytokines or for detecting cells that express them. Cytokine bioassays measure, for instance: (i) cell proliferation induced by cytokines, (ii) chemotaxis, (iii) cytotoxicity, (iv) capacity to induce colony formation, (v) cellular degranulation, or (vi) the induction of secretion of further cytokines or other compounds.

(a) Activity

As mentioned above, standard assays for determining cytokine activity include (a) cytokine-induced proliferation of indicator cell lines; (b) cytokine-induced apoptosis; (c) cytokine-induced protection from viral infection; and (4) cytokine-induced cytokine production. Details for each particular method are well known to the skilled artisan.

Biological responses induced by cytokines show saturation kinetics, which can be used to quantitate their amounts from dose-response curves. These assays involve the use of primary cell cultures and, more frequently, established cell lines that depend upon the presence of (a) particular cytokine(s) for their growth or survival or that respond to a given cytokine in a particular way. (See www.copewithcytokines.de/cope.cgi?key=bioassays). One method is the MTT assay, a quantitative colorimetric method that determines the effect of a cytokine on cell proliferation. The MTT assay utilizes the yellow tetrazolium salt [3-(4,5-Dimethylthiazol-2-yl)-2,5-diphenyltetrazolium-bromide] which is metabolized by mitochondrial succinic dehydrogenase activity of proliferating cells to yield a purple formazan reaction product, which can be detected using a colorimeter.

Other cytokine assays include (1) immunoassays which generally measure immunoreactivities and are useful indicators, therefore, of the presence of cytokines and include (a) radioimmunoassays, (b) immunoradiometric assays, and (c) enzyme-linked immunosorbent assays. These particular assays require cytokine-specific antibodies or labeled cytokines, receptors, or antibodies. Accordingly, the high-affinity antibodies created by the present invention are ideally useful for implementing such immunoassays, especially since the synthesis of some cytokines in vivo often occurs at such low levels that it is difficult their presence by standard immunoassay techniques; (2) the Cytometric Bead Array combines sandwich immunoassays with flow cytometry for simultaneous measurement of the characteristics of multiple particles and has been adapted to the simultaneous determination of a variety of cytokines in small volumes; (3) immunological assays are commercially available for many cytokines; (4) the in vivo cytokine capture assay is a method allowing the determination of in vivo concentrations of cytokines; (5) radioreceptor assays measure concentrations of cytokines by displacing ligands from cell-bound receptors; (6) the reverse hemolytic plaque assay is an adaptation of a immunoglobulin-secreting cell plaque assay that can be used to detect individual cells that secrete cytokines and to determine the amounts of a particular cytokine secreted by this cell; (7) the cell blot assay also allows visualization of release of cytokines by producer cells; (8) the kinase receptor activation assay which exploits the fact that ligand binding to receptors can cause tyrosine phosphorylation of the receptor; hence, activity can be inferred by measuring the amount of receptor phosphotyrosine rather than cell proliferation or cell survival; (9) Factor-dependent cell line assays are assays in which cells respond in a particular way to individual cytokines or freshly isolated cells; (10) cytokine immunotrapping is an assay for studying the kinetics of production and consumption or degradation of cytokines; (11) RT-PCR quantification of cytokine mRNA using probes and PCR primers can be designed to anneal and amplify cytokine genes or their alternatively spliced variants, e.g., the splice variants of HGF, designated as HGF/NK1, HGF/NK2, HGF/NK4, for example, can be amplified or detected using variant-specific primers or probes.

In particular, biological activity of an expressed cytokine can be measured by ED50 on the dose-dependant cytotoxicity (for example, TNFα), stimulation of the proliferation (for example, IL-2), or inhibition of other cytokine induced proliferation on effective cells (for example, TGF-β1) based on the nature of the cytokine.

(b) Comparative Assays

Also provided herein are side-by-side gel comparisons of cytokines that have been expressed by the inventive system alongside the same cytokines expressed in non-human cells to demonstrate the differences in purity and glycosylation state between the two protein products. See FIGS. 7 and 8.

9. Exemplary Therapeutic Uses of Recombinantly-Produced Authentic Cytokines

As detailed in the preceding passages and sections, the cytokines that are expressed from the present inventive stable human cell expression system have a number of advantages and benefits over cytokines that are produced in other cell systems, such as more "human-like" or more "authentic" folding, glycosylation, phosphorylation state, epitope-presentation, and native dimerization characteristics. Accordingly, the actual protein structure produced according to the present inventive method is more similar to its native, endogenous counterpart. This translates into significant advantages in the context of therapeutic uses for these authentic recombinant cytokines. See also Table 2 below for correlations between various cytokines and function. The skilled person is able to correlate particular disorders and diseases with abnormal or malfunctioning cytokine activity and thereby devise a therapy to compensate or rectify that abnormality as is discussed in more detail below.

Cytokines that are expressed in non-human cell systems are not authentic, e.g., they lack human-specific glycosylation patterns, are covalently linked to non-human sugar chains, or are incorrectly folded. Furthermore, those cell cultures cannot be replenished, i.e., the culture of cells cannot be re-used after the recombinant protein has been expressed and isolated from it. For these reasons, such non-authentic cytokines have low potency, short half-life and can induce allergies and undesirable immunogenic responses from the body.

By contrast, the cytokines of the present invention are authentic and human-like. Therefore, the cytokines produced by the present invention have a higher potency and long half-life which means, in realistic and practical terms, that a lesser dosage of the cytokine needs to be administered to an individual in need of it. The lower dose and longer half-life also means that the frequency of dosing can be reduced. Furthermore, because the present cytokines are more human-like, they are less likely to induce allergies or be immunogenic. Overall, therefore, the individual who needs to receive treatment can be entered into a course of treatment that requires him or her to take fewer pills or tablet formulations of the cytokine, or injections of a cytokine preparation, and not so frequently, without fear of side-effects attributable to immunogenic responses triggered by present non-authentic cytokines. See, for instance, the potential side-effects and problems associated with currently available drugs such as Roferon® which is formulated to contain recombinant IFN-$\alpha$2a.

In this regard, because the present invention provides for the recombinant production of highly authentic human cytokine proteins, dosage amounts of the cytokine that are required for a particular use, are dramatically lower than the dosage amounts required for the same cytokine produced from different constructs in different cell types. For instance, the recombinant expression of highly authentic human leukocyte interferon requires only 3 to 5 million IU, as compared to 40 million units per dose required to elicit the same effect from non-authentic human leukocyte interferon (based on yield and authenticity analyses of the presently produced cytokines). This represents a log-10 higher efficacy than the currently produced recombinant human interferons alpha. Accordingly, the side effects produced by interferon alpha are minimal, if any, at 3-5 million units; whereas the 40 million units used to produce the same effect as 3-5 million units however, produces very serious side effects, including serious neurological side effects.

The skilled person is aware of the various in vivo and ex vivo therapeutic uses for the present inventive authentic human cytokines. For instance, the present invention encompasses, and is not limited to, the use of:

(1) recombinantly-produced, authentic interferons for treating multiple sclerosis, immune mediated disease, cancer, autoimmune diseases (such as lupus, asthma, and Crohn's Disease), and viral hepatitis;

(2) recombinantly-produced, authentic interleukins for treating autoimmunity, cancer; IL-6 (Tocilizumab) for treating Castleman's Disease; IL10, IL-11, IL-12, and IL-13 for treating immune cell modulation; IL-21 and Its Receptor for preparing cancer models in mice; IL-1 for treating autoimmune disease (such as rheumatoid arthritis and psoriasis); IL-4 Receptor and IL-5 for treating asthma; IL-8 for treating psoriasis; and IL-12, IL-13, IL-17, and IL-18 for treating TH1-mediated autoimmunity;

(3) recombinantly-produced, authentic TNF-$\alpha$ and inhibitors thereof in FDA-approved and follow-on drugs such as but not limited to Enbrel (Etanercept), Remicade (Infliximab), Golimumab (ONTO 148), Humira (Adalimumab), Cimzia (Certolizumab Pegol), Additional TNF-a Antibody Inhibitors in Autoimmunity and Inflammation; and Tumor Necrosis Factor-$\alpha$ for treating cancer and infection.

(4) recombinantly-produced, authentic chemokines for treating autoimmune diseases; cancer; CCR2 for use as an anti-inflammatory drug.

(5) recombinantly-produced, authentic proteins for development of therapeutics for disorders concerning growth and colony stimulating factors, such as, but not limited to, VEGF for treating angiogenesis, angiogenesis antibodies (Avastin and Lucentis), VEGF Antagonists Macugen, Multi-kinase Inhibitor Sutent, and Nexavar, VEGF Monoclonals and Inhibitors, VEGF Gene Therapy; Hepatocyte Growth Factor; Platelet-derived Growth Factor; Gleevec and other Protein Tyrosine Kinase Inhibitors; Fibroblast Growth Factor; TGF Binding Proteins, and Inhibitors of TGF Beta Signaling; Insulin-like Growth Factor; Keratinocyte Growth Factor; rhKGF for treating oral mucositis; connective tissue growth factor (CTGF); Colony Stimulating Factors (CSF); Erythropoietin; Thrombopoietin; Angiopoietin; Bone Morphogenetic Proteins and Growth Differentiation Factors; rhBMP-2, rhBMP-7, and OPG; Growth and Differentiation Factors GDF; rhGDF-5, rhBMP, Inhibition of Myostatin; and neurotrophic factors for treating development disorders.

The recombinantly-produced, authentic human proteins of the present invention may be formulated into drugs, vaccines, liposomes, or delivered as proteins directly into an individual in vivo or administered to cells or cell cultures in vitro or ex vivo. For instance, the skilled person is aware of a number of approaches have been used to modify peptides for therapeutic application. One approach is to link the peptides or proteins to a variety of polymers, such as polyethylene glycol (PEG) and polypropylene glycol (PPG). See for example U.S. Pat. Nos. 5,091,176, 5,214,131 and 5,264,209, which are each incorporated herein by reference.

A recombinantly-produced, authentic human protein of the present invention may therefore be suitably formulated in pharmaceutical preparations for the oral or parenteral administration. Formulations for parenteral administration include but are not limited to injectable solutions or suspensions and liquids for infusions. For the preparation of the parenteral forms, an effective amount of the active ingredient is dissolved or suspended in a sterile carrier, optionally adding excipients such as solubilizers, isotonicity agents, preservatives, stabilizers, emulsifiers or dispersing agents, and subsequently distributed in sealed vials or ampoules.

The present invention also contemplates conjugates of the authentic human proteins produced by the methods disclosed herein. For instance, an authentic human protein can be combined with a pharmaceutically acceptable carrier, diluent or excipient to produce a pharmaceutical composition (which may be for human or animal use). Suitable carriers and diluents include isotonic saline solutions, for example phosphate-buffered saline. Details of excipients may be found in The Handbook of Pharmaceutical Excipients, 2nd Edn, Eds Wade & Weller, American Pharmaceutical Association, which is incorporated herein by reference. A composition of the invention may also be administered by direct injection. Thus, a therapeutic composition of the present invention may be formulated for parenteral, intramuscular, intravenous, subcutaneous, intraocular, oral or transdermal administration.

The preparation of human proteins, such as cytokines, in liposomal form also can improve the biological activity thereof.

A therapeutic authentic protein of the present invention may be formulated such that administration daily, weekly or monthly will provide the desired daily dosage. The skilled person will appreciate that such a therapeutic composition may be conveniently formulated for administrated less frequently, such as every 2, 4, 6, 8, 10 or 12 hours.

The authentic proteins of the present invention also can be employed in gene therapy of these and other diseases by administering the authentic human protein directly to a patient or individual, or to the patient's or individual's cells. The treated cells may then be reintroduced into the patient or individual. Thus, a desired polynucleotide encoding an authentic human protein of the present invention may be administered directly as a naked nucleic acid construct, and may also be linked to flanking sequences homologous to the host cell genome that facilitate incorporation of the internal expression cassette and, hence desired polynucleotide, into the host cell genome. The individual can be any mammal, reptile, bird, fish, or amphibian. In one embodiment, the individual recipient of gene therapy is a human. Any vector of the present invention can be used to express a desired protein, such as a desired therapeutic cytokine, directly in a cell in vivo and thereby provide a gene therapy approach to treating a particular disease, e.g., a cytokine-related disease or disorder.

The present invention contemplates the use of any of the vectors disclosed herein in the gene therapy treatment of a variety of diseases and disorders. For instance, the present invention contemplates the use of any of the vectors disclosed herein to express in vivo the CFTR gene (cystic fibrosis transmembrane conductance regulator) for the treatment of cystic fibrosis; genes for factors VIII and IX, deficiency of which is responsible for hemophilia A and B), respectively; genes called E1A and P53 that cause cancer cells to undergo cell death or revert to normal; AC6 gene which increases the ability of the heart to contract and may help in heart failure; and VEGF, a gene that induces the growth of new blood vessels (angiogenesis) of use in blood vessel disease. Thus, in one embodiment of the present invention, a vector contains an expression cassette with a desired polynucleotide that encodes a therapeutic protein gene selected by the group consisting of the CFTR gene, the factor VIII gene, the factor IX gene, the E1A gene, the P53 gene, the AC6 gene, and the VEGF gene.

Gene diseases that can be treated with gene therapy using any vector of the present invention includes but is not limited to the expression of one or more genes for the treatment of Spinocerebella ataxia type 1, Huntington s disease, familial hypercholesterolemia (FH), AIDS, cancers such as melanoma, or skin cancer, involves introducing a gene with an anticancer protein called tumor necrosis factor (TNF) into test tube samples of the patient's own cancer cells, which are then reintroduced into the patient; brain cancer, the approach is to insert a specific gene that increases the cancer cells' susceptibility to a common drug used in fighting the disease; and prostate cancer and cervical cancer cells; and Gaucher disease is an inherited disease caused by a mutant gene that inhibits the production of an enzyme called glucocerebrosidase.

A vector of the present invention also can be used in gene therapy to solve problems associated with surgical procedures, such as balloon angioplasty, a procedure which induces the body's immune system to cascade and cause restenosis. Gene therapy using any of the vectors described herein can express gene reduce this overactive healing response.

Thus examples of gene therapies that can be treated by introducing a vector of the present invention into a patient, wherein the vector expresses an appropriate gene to counter or treat the genetic disease include but are not limited to (A) gene transfer therapy for Treating Children and Adults With Limb Girdle Muscular Dystrophy Type 2D (LGMD2D), wherein the vector encodes and expresses in vivo rAAV1.tMCK.human-alpha-sarcoglycan in patients with LGMD2D; (B) gene therapy for treating HIV-1 Infected Patients with any of the vectors disclosed herein that expresses GX-12; (C) gene therapy treatment of prostate cancer using Ad5-yCD/mutTKSR39rep-ADP, RTVP-1, Ad.hIL-12, FP253/Fludarabine, or Ad5-CMV-NIS Gene; (D) gene therapy treatment of Leber Congenital Amaurosis using tgAAG76 (rAAV 2/2.hRPE65p.hRPE65); (E) gene therapy treatment of Sickle Cell Anemia or Thalaassemia; (F) gene therapy treatment of pleural malignancies using BG00001 (adenoviral-mediated interferon-beta); (G) gene therapy treatment of chronic granulomatous disease using phagocyte oxidase subunit transduced CD34 hematopoietic stem cells; (H) gene therapy treatment of in transit melanoma using INGN 241; (I) gene therapy treatment of malignant gliomas using AdV-tk; (J) gene therapy treatment of Bilateral Idiopathic Parkinson's Disease using ProSevin; (K) gene therapy treatment of metastatic breast cancer using adenovirus-mediated human interleukin-12; (L) gene therapy treatment of patients who have received a left ventricular assist device using AAV6.5ERCA2a; and (M) gene therapy treatment of Leber congenital amaurosis caused by RPE65 mutations by using rAAV2-hRPE65

Accordingly, any of these genes can be engineered into any one of the vectors disclosed herein and then that vector introduced into cells of an individual wherein the vector expresses the encoded protein the presence of which in the cell acts to counteract, correct, or otherwise treat the genetic basis or bases of the underlying disease. The vector that encodes the therapeutic protein may be introduced into cells that have been cultured outside of the individual or may be administered directly into the individual and the encoded protein expressed in vivo. Thus, the present invention contemplates both in vivo and ex vivo/in vitro gene therapy methodologies for treating a particular disease.

Thus, one aspect of the present invention is the use of a vector selected from the group consisting of pHZhag, pHZA, pHZA, pHZI, pHZhagA, and pHZhagI in gene therapy wherein the vector expresses a therapeutic protein from a particular expression cassette inserted into the vector. In one embodiment, the pHZhag vector comprises operably linked nucleotide sequences for (i) an hCMV IE, (ii) a human beta-actin promoter, and (iii) a human beta-globin intron. In another embodiment, the pHZA vector comprises operably linked nucleotide sequences for (i) an hCMV promoter, and (ii) a human fibrinogen subunit A signal peptide. In another embodiment, the pHZI vector comprises operably linked nucleotide sequences for (i) an hCMV promoter, and (ii) a human Ig superfamily 8 signal peptide. In another embodiment, the pHZhagA vector comprises operably linked nucleotide sequences for (i) an hCMV IE, (ii) a human beta-actin promoter, (iii) a human beta-globin intron, and (iv) a human fibrinogen subunit A signal peptide. In another embodiment, the pHZhagl vector comprises operably linked nucleotide sequences for (i) an hCMV IE, (ii) a human beta-actin promoter, (iii) a human beta-globin intron, and (iv) a human Ig superfamily 8 signal peptide.

Uptake of naked nucleic acid vectors, such as these, which contain the inventive expression cassettes by mammalian cells can be enhanced by several known transfection techniques for example those including the use of transfection agents. Examples of these agents include cationic agents (for example calcium phosphate and DEAE-dextran) and lipofectants (for example Lipofectam™ and Transfectam™). If desired, nucleic acid constructs may also mixed with the transfection agent to produce a composition. An expression vector of the present invention may also be a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The routes of administration and dosage regimens described are intended only as a guide since the skilled artisan will be able to readily determine the optimum route of administration and dosage regimens for any particular individual and condition.

Accordingly, the present invention also therefore encompasses the use of any of the recombinantly-produced, authentic proteins of the present invention in the preparation of a medicament that is useful for treating a particular disease or disorder, such as any of those disclosed herein. Hence, the present invention encompasses the use of a recombinantly-produced, authentic human cytokine for preparation of a medicament for treating cancer and disease abnormalities concerning cell growth, cell proliferation, cell differentiation, and inflammation. An aspect of the present invention therefore is the use of a recombinantly-produced, authentic human cytokine for preparation of a medicament for treating cancer. An aspect of the present invention therefore is the use of a recombinantly-produced, authentic human cytokine for preparation of a medicament for treating a cell proliferation-associated disorder or disease. An aspect of the present invention is also the use of a recombinantly-produced, authentic human cytokine for preparation of a medicament for treating a cell growth-associated disorder or disease. Another aspect of the present invention is the use of a recombinantly-produced, authentic human cytokine for preparation of a medicament for treating a cell differentiation-associated disorder or disease. An aspect of the present invention is the use of a recombinantly-produced, authentic human cytokine for preparation of a medicament for treating an inflammation-associated disorder or disease.

10. Exemplary Therapeutic Uses of Antibodies Raised Against Recombinantly-Produced Authentic Cytokines Overexpression of certain cytokines are known to be associated with certain diseases and abnormal pathological states. For instance, too much TNFα is associated with inflammation and arthritis. Accordingly, antibodies that block TNFα activity and binding to ligands and receptors helps to alleviate problems associated with inflammation and arthritis. Likewise, blocking VEGF cytokine activity via specific antibody binding is an effective mechanism for treating cancer and undesirable cell proliferation by reducing angiogenesis.

Since the cytokines of the present invention are more human-like and therefore present more authentic epitopes at their surface than cytokines expressed in other cell systems, then the antibodies that are raised against them also will be more authentic with respect to their ability to recognize and target them as antigens in vivo. Thus, antibodies raised against recombinantly-produced, authentic human proteins of the present invention have a higher sensitivity and higher specificity than antibodies that have not been raised against the recombinantly-produced, authentic human proteins of the present invention.

Thus, the antibodies of the present invention, which are raised against the cytokines produced by the inventive method, have higher specificity and higher binding affinity than antibodies raised against cytokines produced elsewhere.

As in the case for the cytokines, since the antibodies have a higher affinity and specificity, it is possible to use a lower concentration or dose in any therapeutic regime that requires administering an antibody to combat a particular cytokine-pertinent disease or disorder.

The skilled person is aware that the present recombinantly-produced, authentic human proteins can be formulated into therapeutic anticancer antibodies, such as those currently available. That is, an antibody raised against the relevant recombiantly-produced, authentic human protein of the present invention can be formulated into antibody-based drugs such as, but not limited to, Panorex® (edrecolomab), Rituxan® (rituximab), Herceptin® (traztuzumab), Mylotarg® (gentuzumab), Campath® (alemtuzumab), Zevalin™ (ibritumomab), Erbitux™ (cetuximab), and Avastin™ (bevicizumab).

Antibodies raised against the recombinantly-produced, authentic human proteins of the present invention, or fragments of such antibodies, can be useful as immunoconjugated anticancer antibodies.

Antibodies of the present invention also are useful for treating cardiovascular disorders, infectious diseases, and inflammatory Diseases; and thus formulated into drugs such as those currently available for treating such disorders and diseases, such as Raptiva™ (efalizumab), Remicade® (infliximab), Humira™ (adalimumab), and Xolair™ (omalizumab).

Antibodies of the present invention also can be useful in the context of transplantation, such as in drugs like Orthoclone OKT3® (muromomab-CD3), Simulect® (basiliximab), and Zenapax® (daclizumab).

Accordingly, the present invention also therefore encompasses the use of any of antibodies (monoclonal or polyclonal), raised against any one of the recombinantly-produced, authentic proteins of the present invention, in the preparation of a medicament that is useful for treating a particular disease or disorder, such as any of those disclosed herein. Hence, the present invention encompasses the use of an antibody raised against one or more epitopes of a recombinantly-produced, authentic human cytokine for preparation of a medicament for treating cancer and disease abnormalities concerning cell growth, cell proliferation, cell differentiation, and inflammation. An aspect of the present invention therefore is the use of an antibody raised against an recombinantly-produced, authentic human cytokine for preparation of a medicament for treating cancer. An aspect of the present invention is the use of an antibody raised against a recombinantly-produced, authentic human cytokine for preparation of a medicament for treating a cell proliferation-associated disorder or disease. An aspect of the present invention is also the use of an antibody raised against a recombinantly-produced, authentic human cytokine for preparation of a medicament for treating a cell growth-associated disorder or disease. Another aspect of the present invention is the use of an antibody raised against a recombinantly-produced, authentic human cytokine for preparation of a medicament for treating a cell differentiation-associated disorder or disease. An aspect of the present invention is the use of an antibody raised against a recombinantly-produced, authentic human cytokine for preparation of a medicament for treating an inflammation-associated disorder or disease.

11. Exemplary Ex Vivo and DIAGNOSTIC uses of Antibodies and Recombinantly-Produced Authentic Cytokines The skilled person also is aware that the authentic proteins of the present invention can be useful in a diagnostic environment too and in screening assays for testing candidate drugs and substances with and without exposure to a particular authentic human protein. Antibodies raised against recombinantly-produced, authentic human proteins of the present invention have a higher sensitivity and higher specificity than antibodies that have not been raised against the recombinantly-produced, authentic human proteins of the present invention. One such diagnostic tool is the cytokine bead array. See Lambeck et al., Clinical Cancer Research 13, 2385, (Apr. 15, 2007), which is incorporated herein by reference. That method permits the simultaneous measurement of multiple cytokines in a small volume of serum, such as by using a LINCOplex kit and related protocol (Linco research, St. Charles, Mo.).

Basically, a diagnostic or detection method of the present invention can entail comparing the expression levels of one or more cytokines from a sample taken from an individual against known amounts of control cytokines, such as in titration comparative studies like ELISA assays and the cytokine bioassays and activity assays described in subsection 8 above. According to the present invention, the authentic human proteins, such as recombinantly-produced, authentic human cytokines, can be used as highly sensitive controls since they are highly similar in size, structure, and molecular weight to native cytokines. Thus, a comparison of an unknown sample against a known concentration of an authentic human cytokine of the present invention will be highly sensitive and accurate. Depending on the results of that comparison of cytokine levels, a conclusion can be made on whether or not the invidual's expression level for one or more cytokines is abnormal and, if so, whether that abnormal expression level is indicative of, or diagnostic of, a particular disease or disorder.

Accordingly, the recombinant authentic proteins and antibodies raised against them according to the present invention can be used in a number of different arrays and multiplexed arrays in diagnostic assays. For instance, the present invention includes the use of authentic proteins and antibodies of the present invention in Multiplex Immunoassay Designs, such as Sandwich assays, Antigen-down assays, Competitive assays, and Reverse-phase assays; in Array Substrates, such as in 96-well plates, on membranes, coated on to slides, deposited onto flow-through chips, and adhered to porous filters; in Array Fabrication, where the protein or antibody is contact printed onto a surface, or used in non-contact dispensing; in Detection Methodologies, such as colorimetric, fluorescent, chemiluminescent, surface plasmon resonance imaging techniques; in Array Processing, such as in microfluidic manipulation and surface acoustic wave processing; and in Image Analysis and Data Acquisition methods.

The antibodies raised against the authentic proteins of the present invention also are useful for producing diagnostic kits for detecting cytokines and related antigens in vitro tests, such as in ELISA assays and histological analyses on human tissue sections. Accordingly, the present invention encompasses kits and reagents that include one or more antibodies that have been raised against one or more of the cytokines produced by the inventive human cell system.

Antibodies that block binding of cytokines to their specific receptors and neutralize their effects ("neutralizing antibodies") can be very useful in studies of cytokine function in particular disease states. In vitro bioassays using neutralizing anti-mouse and anti-human cytokine antibodies therefore are useful for determining the effectiveness of a particular antibody in neutralizing cytokine-induced cell proliferation, apoptosis, viral protection, and inappropriate cytokine production.

For example, using a reference standard calibrated against the World Health Organization natural interferon beta standard (Second International Standard for Interferon, Human Fibroblast GB 23 902 531), authentic recombinant human interferon beta can be tested and can be compared to a recombinant interferon-betala product called Rebif® has a specific activity of approximately 270 million international units (MW) of antiviral activity per mg of interferon beta-1a determined specifically by an in vitro cytopathic effect bioassay using WISH cells and Vesicular Stomatitis virus. Rebif 8.8 mcg, 22 mcg and 44 mcg contains approximately 2.4 MW, 6 MW or 12 MIU, respectively, of antiviral activity using this method.

As mentioned in a preceding subsection, both monoclonal and polyclonal antibodies can be raised against the authentic cytokines produced by the present inventive method. This means, that it is possible to raise antibodies that specifically recognize and target one cytokine in a highly effective manner, as well as antibodies that recognize and target closely related cytokine homologs and variants that might have been produced in vivo by various splicing mechanisms.

With respect to diagnostic kits, the inventive authentic cytokines against which high affinity and specific antibodies were raised, can themselves be used for the creation of titration standards in such kits like those used for conducting ELISA assays or other immunological kits. Thus, the standard curve, when using an authentic cytokine and the antibody that was raised against it, is a much more accurate measurement of antibody-to-antigen binding, than if the antibody was titrated against a cytokine prepared from non-human cells. Thus, the present invention contemplates kits that not only include authentic antibodies, and fragments thereof, but also aliquots of the authentic cytokines produced by the present inventive method as standards against which the antibody binding standard curve can be created in such assays. The sensitivity of antibody-antigen binding will be high. Thus, detection and quantification of the presence and amount of a particular cytokine in a biological sample or tissue section can be readily and more accurately determined using those authentic cytokine/antibody partners to create a standard curve against which unknown samples can be accurately compared and quantified.

The antibodies of the present invention also can be used to prepare and construct cytokine antibody arrays, which can simultaneously detect, in one assay, multiple human cytokines from a variety of sources, including cell lysates, conditioned media, patient sera, plasma, and urine. Such an array, especially when using the antibodies of the present invention, has a high sensitivity making it possible to detect cytokine proteins at very low concentrations, such as in the pg/ml range.

The authentic human proteins and antibodies of the present invention also can be used in screening assays to identify candidate substances, chemicals, compounds, and other proteins that interact with them in some way. For instance, a recombinantly-produced, authentic human cytokine of the present invention can be isolated and purified and then exposed directly to a particular candidate substance, and subsequently monitored under any one of a variety of assays known to the skilled person, and as identified in the Assay subsections above, to determine whether any interaction has occurred between the protein and the candidate substance.

See also for example Table 4 which relates the results of one such screening assay utilizing a recombinantly-produced kinase, p38α to identity and record inhibitor IC50 values when exposed to various compounds. That experiment is described elsewhere herein in more detail but is mentioned here as an example in which a protein or antibody of the present invention can be used in an ex vivo-style screening assay. This current study demonstrates that the properties of the human protein kinase p38 α produced in human cells are distinct from the non-human cell version. Using human kinases with high authenticity for drug screening will allow researchers to avoid pursuing false negative leads and missing promising targets.

The proteins and antibodies produced by the present inventive method and vectors also can be used as reagents in and of themselves. That is, a recombinantly-produced, authentic cytokine of the present invention can be used, for instance, in cell cultures by adding the cytokine to help promote cell growth and viability during culturing; and, as described above, a vector of the present invention can be used in gene therapy regimes to express a particular protein with the cells of an individual.

Each reference and citation disclosed herein is incorporated herein by reference in its entirety. The following examples are merely exemplary and in no way limit the scope of the present invention.

EXAMPLES

Example 1

Cloning of Cytokines

Cloning of cytokines can be accomplished by various methods available to one skilled in the art of genetic engineering. For example, total RNA or poly-A RNA can be purified from human tissues samples abundant in particular cytokine expression (for example lymphocytes) and used as a template for gene specific RT-PCR. Additionally, pre-made cDNA libraries can be purchased from commercial sources and PCR can be employed to amplify the cytokine cDNA directly. Still further, synthetic oligonucleotides can be constructed to create a synthetic gene for the cytokine based on sequence information available in National Center for Biotechnology Information with their gene accession numbers. Additionally, full length cDNA clones can be obtained from, for example, the IMAGE clone consortium (image.IInl.gov/) or Openbiosystems (Huntsville, Ala.). The full length cytokine cDNA clones were obtained from Openbiosystems (Huntsville, Ala.). Gene accession numbers are presented in Table 3.

Cytokines contain signal peptides at their N-terminal that are typically lost in the secreted forms and that can be identified by numerous tools available to one skilled in the art (for example Swiss-Prot protein knowledgebase). Some cytokines have a number of variants, by different transcription that can be also identified by the available tools. Sequences of the secreted cytokines are listed in Subsection 10 above.

To facilitate rapid cloning of cytokines with different signal peptides, pSecTag2c (Invitrogen, Carlsbad Calif.), which is suitable for the production of secreted recombinant protein in mammalian cells (for example, CHO and HEK293), was modified to pHZsec by site directed mutagenesis (Quick Change, Stratagene, Carlsbad, Calif.) to introduce a Srf I restriction site in frame with the Igic leader sequence (see schematic below) using mutagenesis primers SecTag2c-srflf (TCCACTGGTGACGCGCCCGGGCCGGC-CAGGCGCGCC) (SEQ. ID. NO 27) and SecTag2c-srflr (GGGGCGCCTGGCCGGCCCGGGCGCGT-CACCAGTGGA) (SEQ. ID. NO: 33). See FIG. 27 for a schematic of the cleavage site.

The secreted forms of the cytokine genes were translationally fused to the SrfI site in plasmid pHZsec using In-Fusion™ PCR Cloning Kits from Clontech (Mountain View, Calif.) with designed primers.

Vectors (A) pHZsec: Conventional CMV Expression Vector Control

Human cytomegalovirus (CMV) promoter-based vectors are typically used in the design of vectors employed in mammalian cell expression systems. See, for instance, the Product Notes for Invitrogen's "Mammalian Expression Systems" available at tools.invitrogen.comicontent/sfs/productnotes/F_051025_MammalianExpression Vectors-TS-TL-MKT-HL.pdf, and which is incorporated herein by reference.

(B) pHZhag: a Vector with a Human Promoter and a Human Intron

The pHZhag vector, designed herein, consists of human beta-actin promoter and human beta-globin intron. The pHZhag vector expresses a desired polynucleotide or gene sequence at much higher levels than conventional CMV-based vectors; and, unexpectedly, cells expressing the pHZhag vector have higher cell viability and yield fewer contaminating background proteins during purification.

Figure 11:
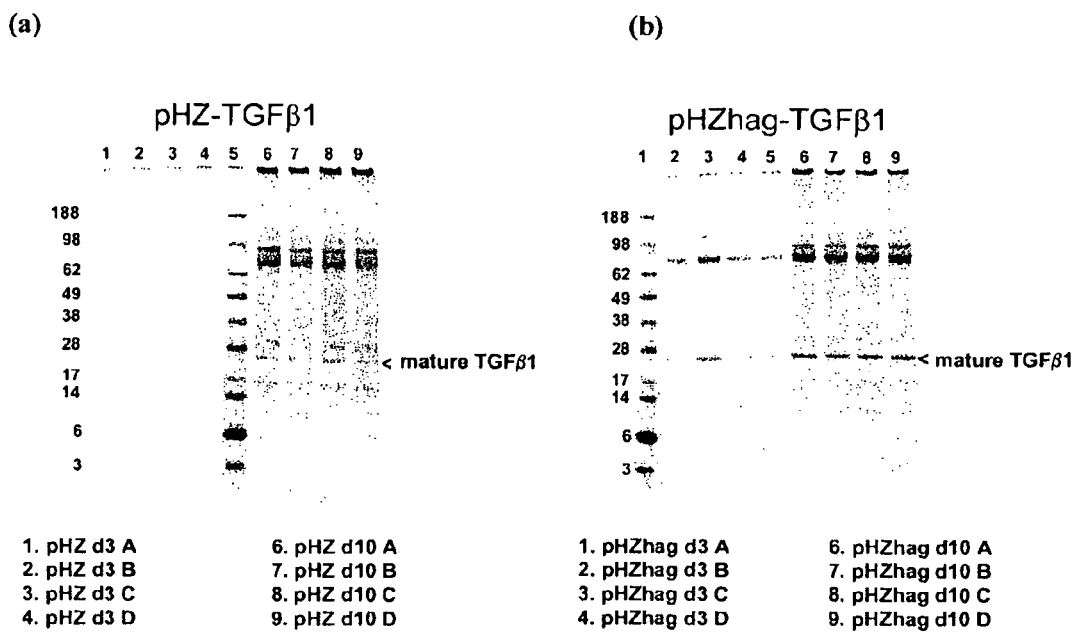
FIG. 11: Example of TGFβ1 expression from HEK293T using (a) pHZsec vector (pHZ-TGFb1) or (b) pHZhag vector (pHZhag-TGFb1). TGFβ1 latency-associated peptide (LAP) and mature TGFβ1 are indicated by red arrows. Both cell lines transfected with pHZhag-TGFβ1 and pHZ-TGFβ1 was treated with extra 20 mM glucose at day 3 (A), day 4 (B), or day 5 (C) and no added (D) in the culture medium. Gels were run the samples of day 3 (d3) and day 10 (d10) for each treatment. For both LAP and mature TGFβ1, pHZhag-TGFβ1 in (b) shows 2-3 fold higher expression than pHZ-TGFβ1 in (a).

The expression profile of the cytokine TGF-131 was compared after expression in human cells using the newly constructed pHZhag vector and the pHZsec vector. See the expression results for pHZ-TG F-β1 and pHZhag-TGF-β1 in FIGS. 11a and 11b, respectively. When the cell lines transfected with each vector reached a comparable cell density and viability TGF-β1 expression level was then compared. The results showed that cells transfected with the pHZhag vector expressed TGF-β1 two to three times fold higher than the expression level for pHZsec.

In addition to the higher expression there was an unexpected observation that pHZhag-transfected cells had a higher cell viability during day 7 to day 9 in contrast to the pHZsec-transfected cells, the viability of which sharply declined during that same time period.

Figure 12:
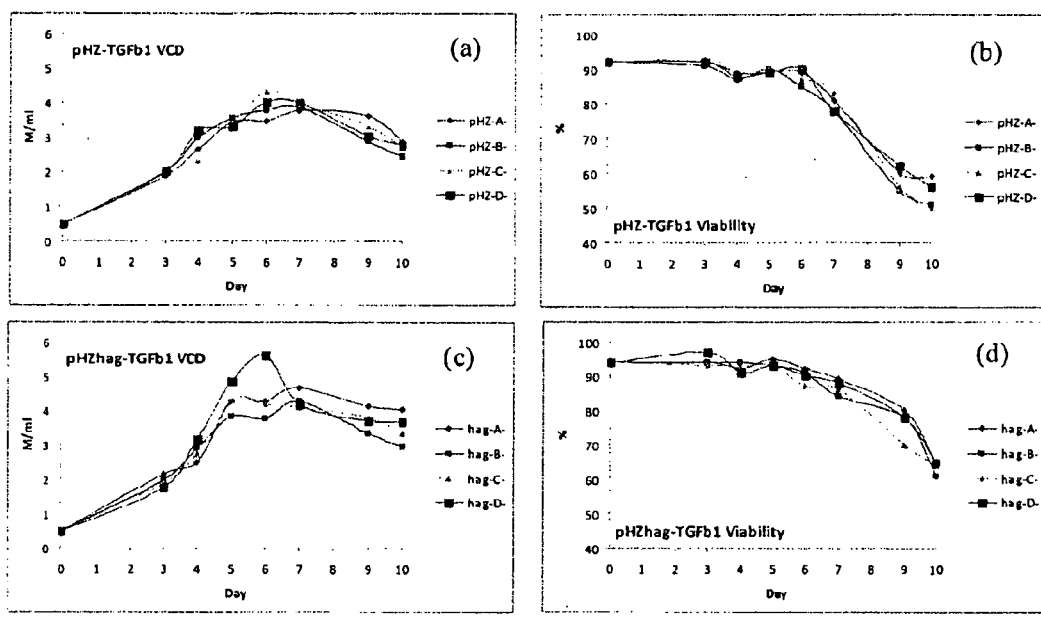
FIG. 12: Cell growth curves of HEK293T cells transfected with pHZ-TGFβ1 (a) and pHZhag-TGFβ1 (c). Viability (%) over the culture period is presented for pHZ-TGFβ1 (b) and pHZhag-TGFβ1 (d). HEK293T cells transfected with pHZhag-TGFβ1 were more than 60% viable even at day 10 (d) where as cells with pHZ-TGFβ1 were below 60% viable at day 8 (b). Higher viability of pHZhag-TGFβ1 transfected cells was also reflected in much less background proteins on the gel in FIG. 11(b).

To elaborate, culture cells are typically harvested at day 7 or day 8 when the cell's viable cell density ("VCD"—million cells per milliliter) reaches over 3 million cells/mL (FIG. 12a) and viability (%) reaches around 60% (FIG. 12b). However, pHZhag-transfected cells kept their viability above 60% even at day 10 (FIG. 12d) and had a VCD of over 3 million cells/mL (FIG. 12c). This is a new and unexpected finding with pHZhag vector.

(C) pHZA and pHZI: Vectors with Human Signal Peptide Sequences

The next step in the design of high-expression vectors that produce highly authentic human proteins was the replacement of the murine Ig kappa chain leader signal peptide sequence, which is widely used in CHO cells, with a human protein signal peptide. The results shown herein indicate that the use of a human signal peptide sequence improves expression levels by at least two fold.

Candidate signal peptide sequences were selected from genes that encode fibrinogen Aa chain (hFbgA), fibrinogen Bb chain (hFbgB), fibrinogen g chain (hFbgG), and human immunoglobulin superfamily 8 precursor signal peptide (hIg8). Protein informatics analysis had showed that a good signal peptide has a high content of Leucine (L). Particularly hIg8 precursor signal peptide was chosen after comparing the signal peptide to the signal peptides of human immunoglobulin superfamilies 1, 2, 3, and 6 because it has high content of Leucine residue (37%) and five consecutive leucines).

Figure 13:
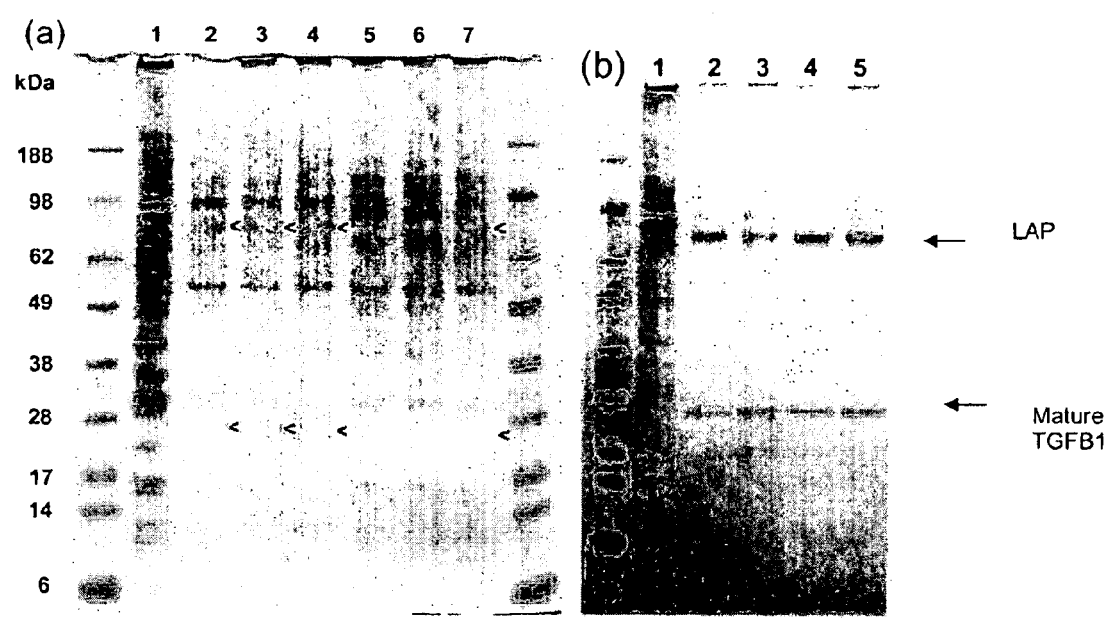
FIG. 13: TGFβ1 expression from HEK293T cells. (a) Expression test with another promoter or signal peptides: Lane 1: mock vector (negative control); Lane 2: pHZsec vector (CMV promoter and mig kappa signal peptide); Lane 3: hag promoter; Lane 4: hFbgA signal peptide; Lane 5: hFbgB signal peptide; Lane 6: hFbgG signal peptide; Lane 7: hIg8 signal peptide. There was no expression with hFbgB and hFbgG signal peptides. (b) Comparison of TGF-β1 expression using mock vector (negative control), pHZ-TGF-β1 (Lanes 2 and 3; murine Ig kappa signal peptide) or pHZA-TGF-β1 (Lanes 4 and 5; human FbgA signal peptide).

Each signal peptide encoding sequence was subcloned into a pHZhag vector and the expression of TGFb1 monitored. The vector, pHZA, which contained the fibrinogen Aa chain signal peptide expressed TGFβ1 well. See FIG. 13a, Lanes 4, 5, and 6. The pHZI vector, expressing the human Ig 8 precursor signal peptide, also expressed TGFβ1 well. See FIG. 13a, Lane 7.

pHZA-TGFβ1 was cultured to the appropriate cell density and its cell viability was recorded to be comparable to that of pHZ-TGFβ1 and pHZhag-TGFβ1. The cells expressing pHZI and pHZA-TGFβ1 had two-fold higher levels of expression of TGFβ1 than that for pHZ-TGFβ1. See FIG. 13b.

(D) pHZhagA and pHZhagI: Vectors with Human Promoter, Human Intron, and Human Signal Peptide Sequences Vectors were designed herein that comprise a human beta-actin promoter, a human intron sequence, and either one of the human signal peptides described above (hFbgA signal peptide or hIg8 signal peptide).

Data comparing pHZhag-TGF-β1 and pHZhagI-TGFβ1 shows about two fold higher expression of pHZhagI-TGFβ1 than that of pHZhag-TGFβ1 and 4-fold higher than pHZsec vector. The following comparative expression studies can be performed using the denoted constructs:

Promoter comparison: pHZ-TGFβ1 vs pHZhag-TGFβ1;

Signal peptide comparison: pHZ-TGFβ1 vs pHZI-TGFβ1 and pHZhag-TGFβ1 vs pHZhagI-TGFβ1 or pHZhagA-TGFβ1, and Promoter and signal peptide combination comparison: pHZ-TGFβ1 vs pHZhagI-TGFβ1 or pHZhagA-TGFβ1.

See FIG. 14 for schematic representations of these vectors.

Example 2

Preparing HEK Cells

Human embryonic kidney cells were placed on a 100 mm Petri dish with the recommended medium (typically DMEM medium with 10% bovine calf serum/2 mM L-Glutamine/10 mM HEPES/1×MEM non-essential amino acid). Cells were kept in the manner for 3 to 4 passages to select the population that attached the plate. The cells attached on the plate were then exposed to various serum-free media (293 SFM II, CD 293, FreeStyle 293, Hybridoma-SFM (from Invitrogen); Ex-Cell 293 (JRH Biosciences)), for 4 days in the plate to select the cells that grow or survive in the serum-free medium. Those cells were then placed back in the 10% serum medium to produce working cell bank.

(A) Cell Line Adapted to Serum-Free and Chemically Defined Media

Figure 15:
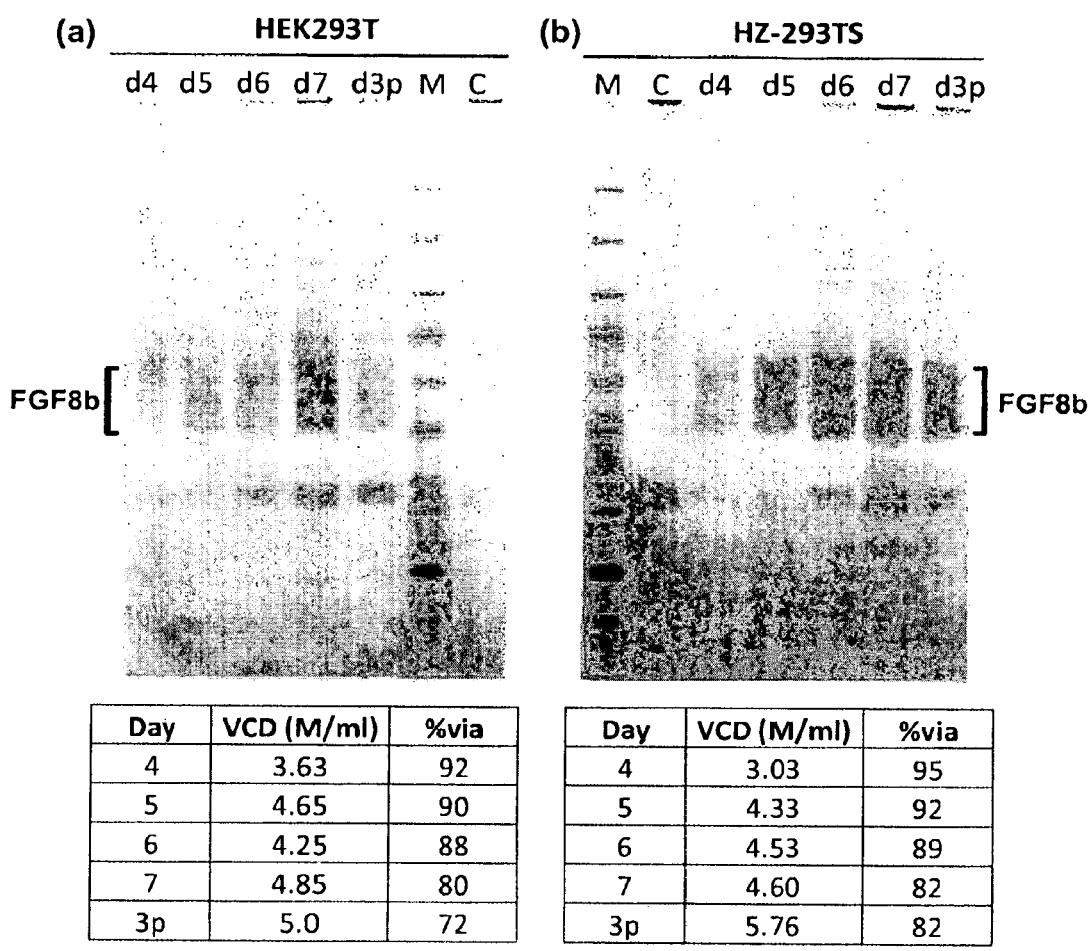
FIG. 15: Human FGF8b expression from HEK293T (a) and HZ-293TS (b). Two to three fold higher expression of FGF8b from HZ-293TS than that from HEK293T was unexpected observation. As the cells in suspension their viable cell density (VCD) reached up to 5-6 million cells per milliliter as in the tables below the gels.
Figure 16:
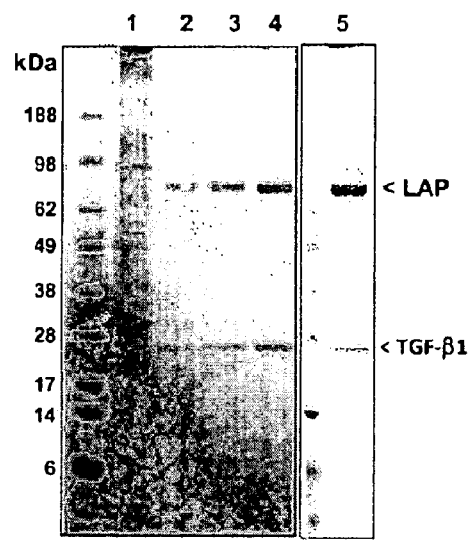
FIG. 16: Comparative gene expression results for different vectors expressing TGF-β1. Comparison of TGF-b1 expression level at day 5 from suspension 293T culture using different vectors. 1, negative control; 2, hCMV promoter with murine IgK signal peptide; 3, hag promoter with murine IgK signal peptide; 4, hCMV promoter with human fibrinogen alpha chain signal peptide; 5, hCMV promoter with human Ig superfamily 8 signal peptide. Latency-associated peptide (LAP) and mature TGF-b1 are indicated by arrows. All the cells are about three million cells/ml and 90% viability. Lane 1=control; Lane 2—pHZ-TGF-β1; Lane 3=pHZhag-TGF-β1 (hCMV IE+β-actin promoter+β-globin intron+TGF-β1); Lane 4=pHZA-TGF-β1 (hCMV promoter+fibrinogen subunit A signal peptide+TGF-β1); Lane 5=pHZI-TGF-β1 (hCMV IE+β-actin promoter+β-globin intron+human Ig superfamily 8 signal peptide+TGF-β1).

HZ-293TS: HEK293T (or 293T) is a HEK293 cell genetic variant (ATCC CRL-11268). This cell line was adapted to serum-free and chemically defined media using the manufacturer's reagents (Invitrogen). Adapting HEK293T cells to suspension and completely serum-free and chemically defined media is novel. HZ-293TS reaches at least about 5 to 6 million cells per milliliter (VCD) in suspension culture (FIG. 15b, table). The human cell line which is denoted as HZ-293TS is deposited under, and bears the ATCC biological deposit accession number of PTA-10165, deposited on Jul. 1, 2009.

HZ-293TS cell lines can be cultured in serum-media as adherent on the plates, as well as in serum-free and chemically defined media, as suspension in the shaking flasks, spinners, and bioreactors. This feature allows HZ-293TS cells to be plated as monolayer in serum media and subsequently transfected. Transfected cells then can go to suspension directly or can be selected on the plate prior to the suspension culture like a shuttle system.

There have been three 293 cell lines reported available for suspension culture: HEK293S, FreeStyle293, 293EBNA. Among those three HEK293S and FreeStyle293 are of HEK293 cell line that has been known to have much less recombinant protein expression than 293T and 293EBNA that are capable for episomal amplification of the plasmid of interest. Further advantage of HZ-293TS over and FreeStlye293 and 293EBNA is that the selected cells stably expressing the recombinant of interest have versatile scalability and continuous culture (more than 20 passages without losing expression level) while transfected in suspension 293EBNA and FreeStyle293 are mostly for single harvest within a short period of time. To evaluate what is the characteristic of HZ-293TS in terms of recombinant protein expression level human FGF8b cytokine was transfected to HZ-293TS using the shuttle way and its expression level was compared with that from current HEK293T system in following section 2.

HZ-293S: HEK293 cell line (ATCC CRL-1573) adapted to the serum-free and chemically defined media. This cell line has not yet been tested for recombinant protein production.

HZ-293EBNA: 293EBNA cell line (Invitrogen R6200&7) adapted to the serum-free and chemically defined media. Although 293EBNA has episomal amplification ability, like HEK293T, it requires OriP (EBV origin of replication) in the plasmids that limited further use of this cell line. This cell line has not yet been tested for recombinant protein expression.

(B) Application of HZ-293TS to Recombinant Cytokine Production

Because of its easiness of maintaining in suspension culture and adaptation to monolayer culture, the HZ-293TS cell line was tested for its recombinant protein production capability compared to that of HEK293T for expressing human FGF8b cytokine-encoding plasmid. When both cell lines reach a comparable cell density and viability, the cytokine expression in the HZ-293TS cells was unexpectedly 2 to 3 fold higher than that of 293T. Thus, HZ-293TS has become a very different cell line from 293T and that can be the reason for higher recombinant cytokine expression.

Other proteins have been expressed at much higher levels in the inventive HZ-293TS cells than in HEK293T cells, including but not limited to expression of Activin A, FGFbasic, IL-1β, IL-23, VEGF165, and TGFβ1. See for example the comparative data presented in the Figures for FGFbasic and TGFβ1.

Example 3

Transfection

One day before transfection a confluent 100 mm dish of the cells was passed to 5 dishes (70~80% confluency). A 100 mm dish transfection requires 500 ul DMEM medium without supplements, 10 ug plasmid DNA, and a certain amount of transfectant (FuGene 6, FuGene HD (from Roche); Lipofectamin, Lipofectamin 2000, 293fectin (Invitrogen); Polyetheleneimine), according to the manufacturer's manual. Mixture of transfection materials was added to the culture dish in drop wise.

Example 4

Antibiotics Selection

Forty-eight hours later the transfected cells were harvested by centrifugation after trypsin treatment. The cell pellet was resuspended in 5 ml fresh 10% serum medium. One hundred micro liters of resuspended cells was added into a six well plate with 2 ml of the serum medium with certain concentration of antibiotics (for example, 400 ug/ml or 800 ug/ml) (neomycine (G418), hygromycine, zeocin, blasticidine).

Media in the six-well plate was changed with fresh including antibiotics every 3 to 4 days later for two weeks by then transfected cells grow as cell colonies while untransfected ones died out. Cell colonies were harvested with trypsin treatment and transferred into new plate with fresh serum medium including a quarter concentration of antibiotics and grown for two weeks.

Example 5

Suspension Adaptation

Once the selected cells were confluently grown in the plate the cells were trypsin treated to detach from the plate. Two plate amounts of cells were harvested after trypsin treatment and resuspended in 10 ml of serum-free medium (for example CD 293) including 1% serum and antibiotics. Adaptation may take up to 8 weeks and the medium was changed every 3 to 4 days depending on the cell condition. Later the cells were transferred to serum-free medium and antibiotics only. This adaptation takes up to 4 weeks and the medium was changed every 3 to 4 days depending on the cell condition. Once suspension adapted cells were continuously grown to larger scales for production and cryo-banked in fresh medium plus 10% DMSO for future production.

Example 6

Transfection and Establishment of Stable HEK 293 Cells Expressing Cytokines

Cytokine expression plasmids were transfected into 293 cell lines, or derivatives thereof (e.g., HEK 293T, HEK 293S, and HEK 293 EBNA) that are serum-free adapted in house, in 100 mm Petri dishes using transfectant FuGene 6 (Roche) according to manufacturer's recommendations. Transfected cells were grown in DMEM medium, supplemented with 10% BCS, 1% MEM non-essential amino acids, 1% penicillin-streptomycin and 2 mM L-glutamine. Forty-eight hours later the transfected cells were harvested by centrifugation after trypsin treatment. The cell pellet was resuspended in 5 ml fresh 10% serum medium. One hundred micro liters of resuspended cells was added into a six well plate with 2 ml of the serum medium with certain concentration of antibiotics (for example, 400 µg/ml or 800 µg/ml zeocin).

Media in the six-well plate was changed with fresh including antibiotics every 3 to 4 days later for two weeks by then transfected cells grow as cell colonies while untransfected ones died out. Cell colonies were harvested with trypsin treatment and transferred into new plate with fresh serum medium including a quarter concentration of antibiotics and grown for two weeks.

Once the selected cells were confluently grown in the plate the cells were trypsin treated to detach from the plate. Two plate amounts of cells were harvested after trypsin treatment and resuspended in 10 ml of serum-free medium (for example CD 293) including 1% serum and antibiotics. Adaptation takes up to 8 weeks and the medium was changed every 3 to 4 days depending on the cell condition. Later the cells were transferred to serum-free medium and antibiotics only. This adaptation takes up to 4 weeks and the medium was changed every 3 to 4 days depending on the cell condition. Once suspension adapted cells were continuously grown to larger scales for production and cryo-banked in fresh medium plus 10% DMSO for future production.

Example 7

Purification of Cytokines

Human cytokines are modified by complicated post-translational molecular mechanisms such as glycosylation, phosphorylation, and multimerization, and are subjected to a complicated cleavage and conversion process that modifies their intrinsic physicochemical properties based on bare amino acid sequences and that make their purification difficult without any tag in particular. The present invention encompasses the development of efficient purification scheme utilizing up to three steps of conventional chromatography and yielding >95% purity on SDS-PAGE. The purification scheme is consisted of capture with immobilized metal ion affinity chromatography followed by purification and polishing with ion exchange chromatography.

After 6 days growth, the supernatant of the serum-free medium was collected by centrifugation and the cell pellet was resuspended in fresh serum-free medium for further production of the cytokine. Expression of cytokines was identified on SDS-PAGE gel with Coomassie stain by known molecular weight or on PVDF membrane with Western blot. To capture the cytokine, the supernatant was at first loaded on an immobilized metal affinity chromatography (IMAC) column. Based on their properties some cytokines were bound on IMAC column while some were found in flow through. As next purification step cytokine fraction pool was loaded on an ion exchange chromatography (IEX) column after buffer exchange to a proper buffer condition. Finally as polishing step cytokine fraction pool was loaded on another IEX or different affinity chromatography (for example Heparin resin) column.

After up to three chromatography steps cytokines were more than 95% pure judged by Coomassie stain on SDS-PAGE gel (FIG. 7) and by Western blot with available antibodies (FIG. 8). Pure cytokines then were quantified using known methods available to one skilled in the art (for example Bradford assay, Coomassie stain on the gel, and OD280 nm). After the quantification cytokines were analyzed endotoxin level by endotoxin detection kit from Lonza (Allendale, N.J.) according to manufacturer's manual, aliquoted based on required amounts and lyophilized for commercialization.

Figure 17:
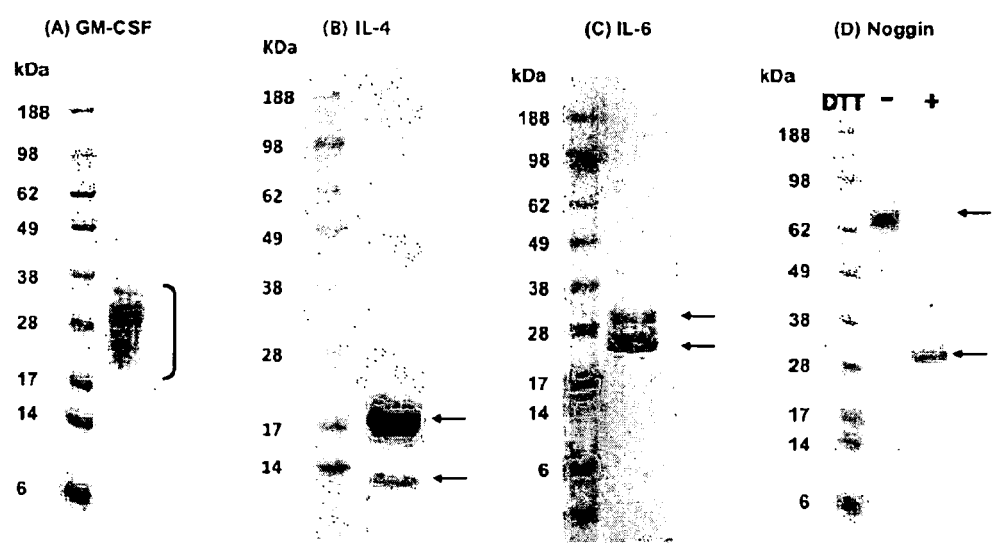
FIG. 17: Efficient tag-free purification. Purified recombinant human (A) GM-CSF, (B) IL-4, (C) IL-6, and (D) Noggin from engineered human cells. All cytokines are expressed as native proteins without tag. Efficient purification protocols were developed to yield authentic cytokines with native heterogeneous glycosylation (A-D) and a disulfide bond (D).

GM-CSF, IL-4, and IL-6 recombinantly-produced using the inventive human cell expression system are glycoproteins with different degrees of glycosylation. The disclosed and inventive, efficient purification scheme yielded GM-CSF with a range of heterogeneous glycosylation (FIG. 17A), and IL-4 and IL-6 with distinct glycosylation (FIGS. 17B&C) in high purity. The purification scheme was also applied to purify authentic homodimer Noggin purification (FIG. 17D).

Example 8

Activity Assay

Biological activity of the cytokine was measured by $ED_{50}$ on the dose-dependant cytotoxicity (for example, TNFα), stimulation of the proliferation (for example, IL-2), or inhibition of other cytokine induced proliferation on effective cells (for example, TGF-β1) based on the nature of the cytokine. See FIGS. 6A-M.

Example 9

Comparative Analysis of Cytokines Expressed from the Inventive Human Cell System and Non-Human Cells Experiments were conducted to compare the purity and extent of glycosylation between cytokines expressed according to the present inventive method and those that were expressed in non-human cells. FIGS. 7 and 8 depict side-by-side comparisons of SDS-PAGE gel analyses of different cytokines in non-reduced and reduced human cells as compared against non-reduced and reduced non-human cells. The cytokines that were compared in such fashion include EPO, Noggin, G-CSF, SCF, GM-CSF, Somatotropin, IL-2, TGFβ1, IL-4, TNFα, IL-6, VEGF-165, and M-CSF. FIG. 8 shows the comparative results of Western Blot analyses of those same cytokines between the inventive human expression system and non-human expression system. This data show that the stable human cell culture of the present invention expressed cytokines that have molecular weights and authentic tertiary structures and activities that are comparable to native human cytokines and distinct from the sizes and structures of cytokines expressed from non-human cells. Furthermore, the antibodies raised against the authentic cytokines, due to the presentation of authentic epitope surfaces, have high affinity binding properties.

Example 10

VEGF165 AND IL-4 Comparative Data

Figure 9:
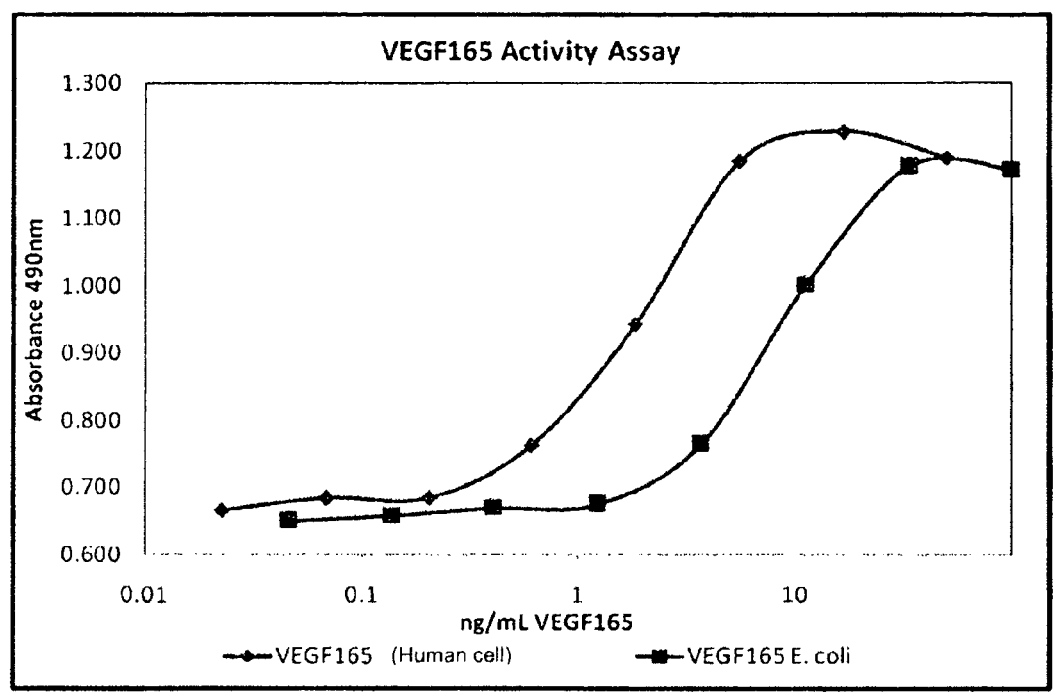
FIG. 9: Comparison of VEGF165 activity in human and non-human cells.

VEGF165 plays a prominent role in normal and pathological angiogenesis. It has been demonstrated that inhibition of VEGF activity by treatment with a monoclonal antibody specific for VEGF can suppress tumor growth in vivo. Currently, commercially available VEGF165 protein reagents are produced from non-human cells including *E. coli* and insect cells. The inventive method disclosed herein has been use to produce VEGF165 from engineered human 293 cells. FIG. 9 shows a comparison of activities of VEGF165 expressed between *E. coli* and human cells the molecular mass of the *E. coli* expressed protein in monomer is 18 kD. This compares with the inventive VEGF165 which migrates as a band of 28 kD due to glycosylation. See FIG. 9 for comparative activities of VEGF in human and non-human cell systems.

The bioactivity of the VEGF165 produced by the inventive stable human cells was determined by its ability to induce proliferation of human umbilical vein endothelial cells, indicating that that VEGF165 is 6-fold more active than the *E. coli* expressed protein.

Figure 10:
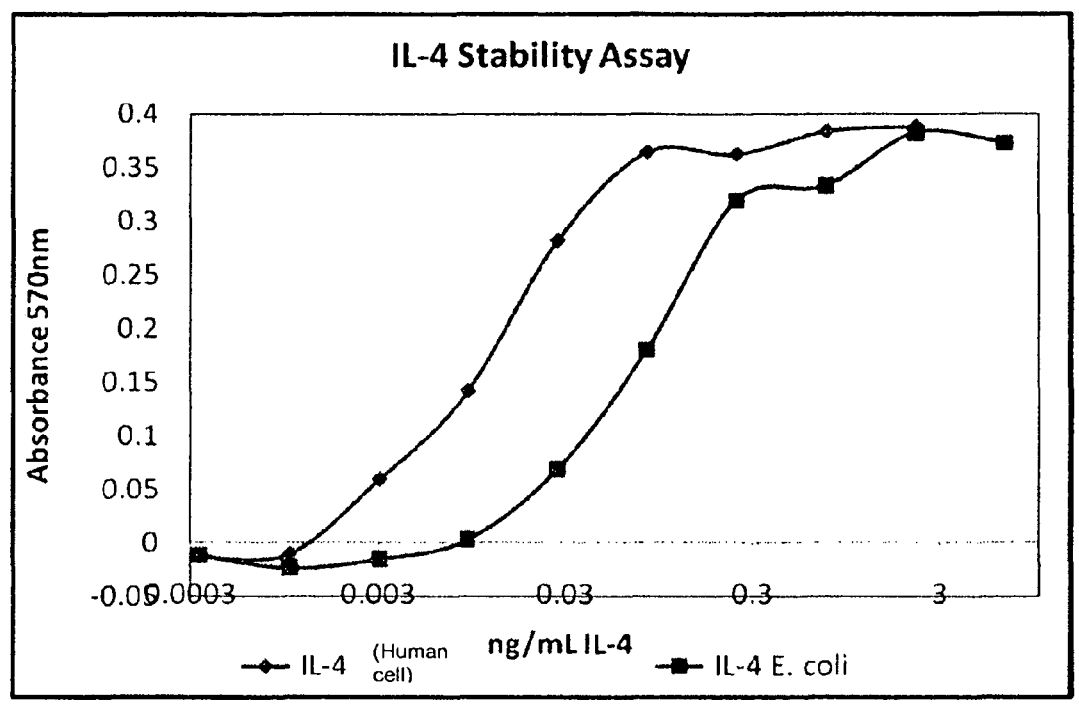
FIG. 10: Comparison of IL-4 activity in human and non-human cells.

IL-4 plays a critical role in the development of allergic inflammation and asthma. Currently, commercially available IL4 protein reagents are produced from *E. coli* with a molecular mass of 14 kD (FIG. 7C). This compares with the IL4 from human cells which migrates as a major band of 19 kD due to glycosylation. The biological activity of IL-4 was determined by the dose-dependent stimulation of the proliferation of human TF-1 cells. As shown in FIG. 10, IL4 has 4-fold higher potency than the *E. coli* expressed cytokine. See FIG. 10 for comparative activities of IL4 in human and non-human cell systems.

Figure 8C:
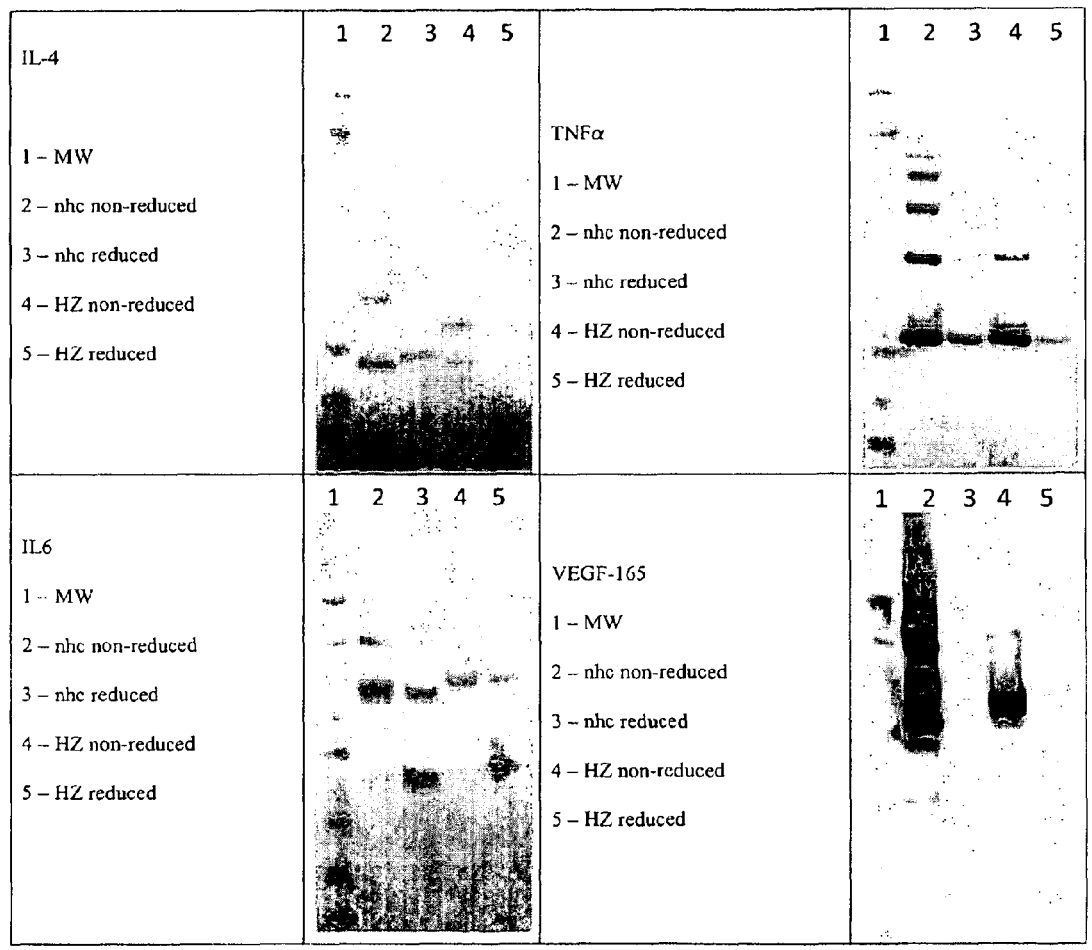

Cytokines produced in *E. coli* are not glycosylated and may expose cryptic or normally hidden epitopes. Hence, antibodies may have different affinities for native human proteins compared to the *E. coli* produced proteins. Indeed, Western blot analysis shows the monoclonal antibodies raised against a full length protein from insect cells recognize the VEGF165 protein from *E. coli* as well as other highly reactive species that may correspond to micro-aggregates (FIG. 8C). In contrast, only one band is seen with the human cell version. The monoclonal antibodies raised against a full length protein from *E. coli* recognize the protein from *E. coli* under both reducing and non-reducing conditions. In contrast, only the protein under non-reducing conditions is detected with the human cell version.

Example 11

Authentic TGF-β1

Figure 18:
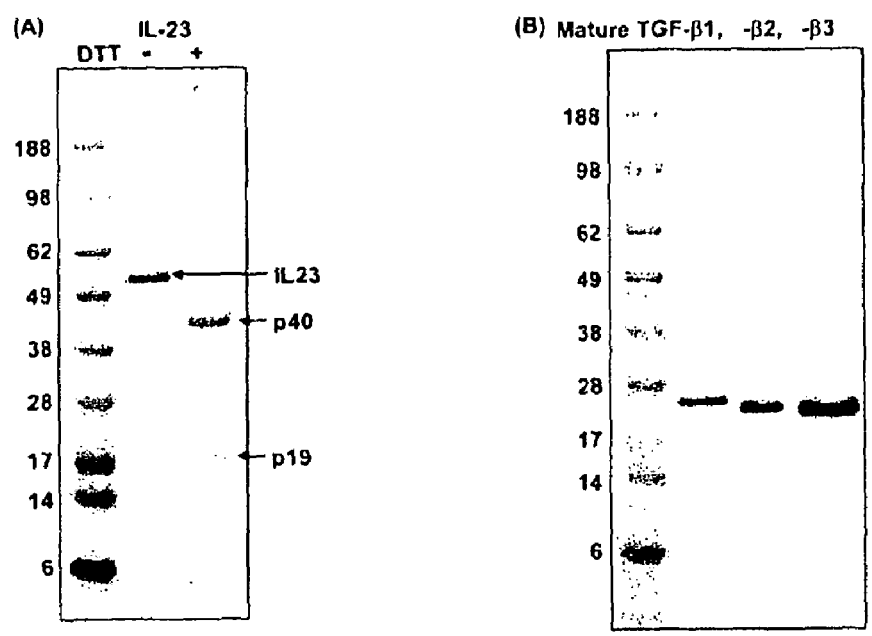
FIG. 18: Production of difficult to express cytokines. Purified recombinant human IL-23 (A) and mature TGF-β1, -β2, and -β3 (B) from the human cell expression system. Human cell expression system efficiently expressed cytokines that are very difficult to express or not properly expressed in non-human cells due to its complexity of glycosylated and disulfide linked subunits (A: IL-23) or due to a delicate conversion process from latency-associated peptide (LAP) complex to mature form (B: TGF-β1, -β2, and -β3).

Transforming growth factors beta (TGF-β) are highly pleiotropic cytokines that act as cellular switches and regulate immune function, proliferation and epithelial-mesenchymal transition. These proteins are produced as precursors. A furin-like convertase processes the proprotein to generate an N-terminal latency-associated peptide (LAP) and a C-terminal mature TGF-β. Disulfide-linked homodimers of LAP and TGF-β remain non-covalently associated after secretion, forming the small latent TGF-β complex. Covalent linkage of LAP to latent TGF-β binding proteins create large latent complex that may interact with the extracellular matrix. Commercially available TGF-β proteins are produced as a recombinant protein expressed in CHO cells or as purified native protein from human platelets. Due to complex post-proteolytic modifications, TGF-β yield is low and the products are not available in economic bulk quantity. The efficient and inventive human-cell based expression system has been herein developed for scalable production of various human cytokines and produces highly authentic human TGF-β1, β2 and β3 proteins from engineered human 293 cells. The proteins are highly purified disulfide-linked dimers of 25 kD that can be cost-effectively produced in large scale (FIG. 18B).

IL-17-producing CD4+ T cells (Th-17 cells) have been identified as a unique subset of Th cells that develop along a pathway that is distinct from the Th1, and Th2-cell differentiation pathways. This finding has provided exciting new insights into immunoregulation, host defense and the pathogenesis of autoimmune diseases. Recently it has been shown that IL1β, IL6 and IL23 are important in driving human Th17 differentiation. However, TGF-β1, which is important for the differentiation of murine Th17 cells, is reported to be not required, and even inhibits human Th17 differentiation (McGeachy & Cua (2008) *Immunity* 28:445, Chen & O'Shea (2008) *Cytokines* 41:71). In this study, whole CDE4+ cells isolated from a healthy donor were stimulated with 10 μg/mL plate bound anti-CD3 and 10 μg/ml soluble anti-CD28 in the presence of Th17 polarizing cytokines from the inventive human cell expression system and from an insect cell or bacterial expression system. After 5 days supernatants were harvested for measurement of IL-17 by ELISA.

Figure 22:
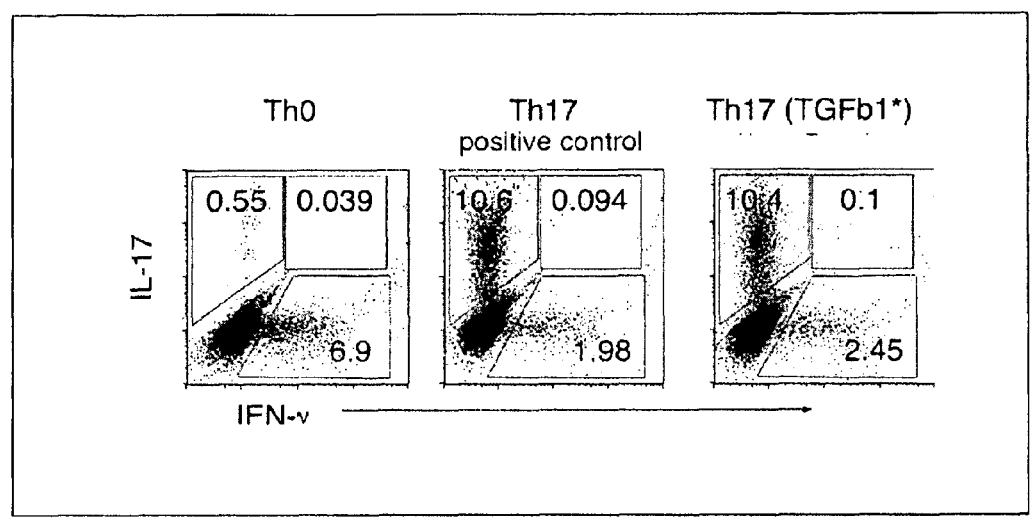
FIG. 22: Efficient differentiation of Th17 cells with authentic cytokines expressed in human cells. Whole CD4+ T cells isolated from a healthy donor were stimulated with 2 μg/mL plate bound anti-CD3 and 1 μg/mL soluble anti-CD28 in the presence of Th17 polarizing cytokines, including a titration of IL-23. After 5 days, supernatants were harvested for measurement of IL-17 by ELISA. See (A)-(G).

The results show that recombinantly-produced, authentic human IL1β, IL6 and IL23 are significantly more effective in inducing IL-17 secretion. More importantly, it demonstrates the recombinantly-produced, authentic human TGF-β1 is also effective in enhancing the effect. In contrast, this cytokine from insect cells only showed marginal effect. The results indicate that by using more authentic cytokines, it is possible to more effectively induce Th17 cell differentiation and lead to more accurate scientific understanding of human biological process. A separated study performed under the same condition with TGF-β1, TGF-β2, and TGF-β3 (FIG. 18B) from the inventive human cell expression system demonstrated that all three biologically relevant cytokines can effectively induce Th17 cell polarization (FIG. 22E-G). Furthermore, in another study, among commercially available TGF-β1 cytokines only authentic TGF-β1 FIG. 22H) matched human platelet derived native TGF-β1 ('positive control' in FIG. 22H) in differentiation of a naïve T cell (Th0) to Th17 cells presented by flow cytometry analysis on the population of IL-17 and INF-γ producing cells (FIG. 22H).

Example 12

Authentic VEGF

VEGF165 is a member of the cysteine-knot growth factor superfamily. This cytokine stimulates proliferation and survival of endothelial cells, and promote angiogenesis and vascular permeability. Expressed in vascularized tissues, VEGF165 plays a prominent role in normal and pathological angiogenesis. It has been demonstrated that inhibition of VEGF165 activity by treatment with a monoclonal antibody specific for VEGF165 can suppress tumor growth in vivo.

Figure 19:
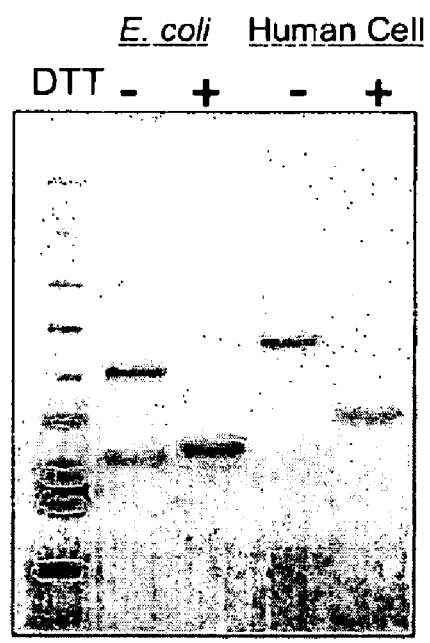
FIG. 19: Recombinantly-produced, authentic human VEGF165 a homodimer. VEGF165 expressed from E. coli and engineered human 293 cells. The E. coli expressed protein is lack of glycosylation and a mixture of monomer and dimer (19 kDa and 38 kDa, respectively), whereas human cell expressed protein is fully glycosylated homodimer of 45 kDa.

Currently, commercially available VEGF165 proteins are produced from non-human cells including *E. coli* and insect cells. Authentic VEGF165 has herein been produced from engineered human 293 cells. The *E. coli* expressed protein is a mixture of monomer and dimer and has a molecular mass of 18 and 38 kD in SDS-PAGE. This compares with the recombinantly-produced, authentic human VEGF165 which migrates as a glycosylated band of 45 kD due to glycosylation and dimerization (FIG. 19). The bioactivity of the recombinantly-produced, authentic human VEGF165 was determined by its ability to induce proliferation of human umbilical vein endothelial cells. These results indicate that the recombinantly-produced, authentic human VEGF165 is 10-fold more active than the *E. coli* expressed protein under the same bioassay condition: $ED_{50}$ of 1 ng/mL for the recombinantly-produced, authentic human VEGF protein vs 10 ng/mL for *E. coli* expression (FIG. 9).

Example 13

Authentic EPO

Figure 20C:
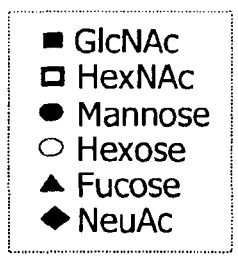
FIG. 20: More authentic: human EPO vs CHO EPO. Recombinant EPO expressed from human cells exhibits apparent molecular mass of 34 kDa on SDS-PAGE as native human serum EPO (Skibeli et al. 2001 Blood 98:3626) whereas CHO EPO exhibits apparent molecular mass of 40 kDa (A). Human EPO contains substantially high content of neutral glycans compared to CHO EPO (B). (C) Acidic glycan structures of human EPO and CHO EPO. The most abundant glycans in human EPO are tetra-antennary complex types whereas those in CHO EPO are enlongated bi-antennary complex types. Symbols are GlcNAc (■), HexNAc (□), Mannose (•), Hexose)(°), Fucose (▲), NeuAc (♦).

Erythropoietin (EPO) is a 34 kD glycoprotein hormone which is related to thrombopeietin. This protein promotes erythrocyte formation by preventing the apoptosis of early erythroid precursors. It has been shown glycosylation of EPO is required for biological activities in vivo. Currently, commercially available recombinant human EPO proteins are produced from CHO cells. These recombinant proteins differ from the native human EPO by having higher apparent molecular mass of 40 kD on SDS-PAGE gel (FIG. 20A) and lower content of neutral glycans (FIG. 20B). Recombinantly-produced, authentic human EPO has herein been produced from engineered human 293 cells. Similar to the native human protein in the literature (Skibeli et al. (2001) *Blood* 98:3626), recombinantly-produced, authentic human EPO exhibits a lower apparent molecular mass and substantially higher content of neutral glycans. Furthermore, recombinantly-produced, authentic human EPO has more abundant and diverse glycan profiles than the CHO cell produced version. The most abundant glycans in the recombinantly-produced, authentic human EPO are tetra-antennary complex types whereas those in CHO EPO are elongated bi-antennary complex types (FIG. 20C).

Example 14

Authentic IL-23

Currently, commercially available recombinant IL-23 cytokine is produced as a heterodimeric or fusion protein from an insect cell expresion system. Recombinantly-produced, authentic human IL-23 has been herein produced in a stable cell culture of engineered human HEK293 cells. The protein is expressed as a disulfide-linked heterodimer of 55 kD and, due to the scalability of the stable culture, can be cost-effectively produced and efficiently purified (FIG. 18A).

Figure 21:
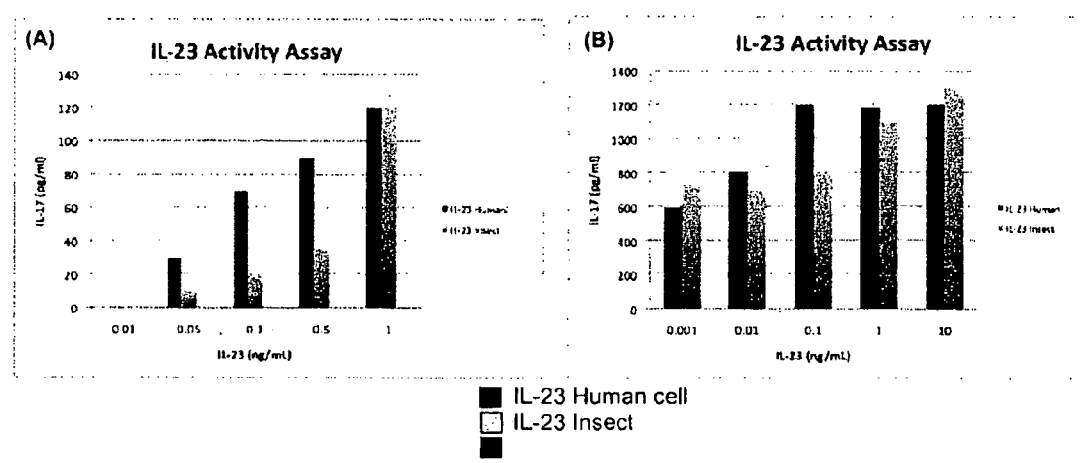
FIG. 21: IL23 expressed in human cells of the present invention is 500-fold more potent than the cytokine produced from insect cells. Authentic IL-23 expressed in human cells 100× more potent for induction of human Th17 cells. (A) IL-23 activities determined by the dose-dependent secretion of IL-17 from mouse splenocytes activated with 10 ng/ml PMA. (B) IL-23 activities determined by the dose-dependent secretion of IL-17 from human CD4+ T cells stimulated with 2 mg/ml plate bound anti-CD3 and 1 mg/ml soluble anti-CD28 in the presence of Th17 polarizing cytokines.

IL-17-producing CD4+ T cells (Th17 cells) have been identified as a unique subset of T helper cells that develop along a pathway that is distinct from the Th1 and Th2-cell differentiation pathways. This finding has provided exciting new insights into immunoregulation, host defense and the pathogenesis of autoimmune diseases. Recently it has been shown that TGF-β1, IL-β1, IL-6 and IL-23 are important in driving human Th17 differentiation (Chen & O'Shea (2008) *Cytokines* 41:71). The bioactivities of IL-23 from human and insect cells were first determined by the dose-dependent secretion of IL-17 from mouse splenocytes activated with 10 ng/ml PMA, which shows that recombinantly-produced, authentic human IL-23 is ten fold more active (FIG. 21A). The activities were further assayed with human CD4+ cells which were isolated from a healthy donor and stimulated with 10 μg/ml plate bound anti-CD3 and 10 μg/ml soluble anti-CD28 in the presence of Th17 polarizing cytokines. After 5 days supernatants were harvested for measurement of IL-17 by ELISA. The results show that recombinantly-produced, authentic human IL-23 is 100-fold more potent for inducing IL-17 secretion in two independent studies, maximum induction was achieved with 0.1 ng/ml of the recombinantly-produced, authentic human IL-23 vs 10 ng/ml with insect cell-produced IL-23 (FIG. 21B). These results demonstrate that authentic human cell expressed cytokines can induce Th17 cell differentiation at physiologically relevant concentrations.

IL-23 is a glycosylated hetero dimer protein of IL12p40 and IL23p19. Currently, commercially available recombinant IL-23 cytokine is produced as a heterodimeric or fusion protein from an insect cell expression system. Authentic IL-23 has been herein produced in a stable cell culture of engineered human HEK293 cells. The protein is expressed as authentic disulfide-linked dimer of 55 kD and, due to the scalability of the stable culture, can be cost-effectively produced. (FIG. 18A).

Example 15

Authentic GM-CSF and IL-4 Enable Medium-Change-Free Differentiation of Dendritic Cells Purified human peripheral blood monocytes were cultured in either G4 DC medium (as specified below) at $5 \times 10^5$ cells/ml in humidified air containing 5% $CO_2$ at 37° C. for a total of 7 days. HZ G4 DC was used at 5 ng/ml of recombinantly-produced, authentic human GM-CSF and IL-4 without medium replacement whereas EC G4 DC was used routinely (50 ng/ml of *E. coli* GM-CSF and IL-4 with 50% medium replacement on day 3 and day 5). On day 6, Lipopolysaccharide (LPS) was added to half of the wells to induce DC maturation while the other half of the wells were used as sham treatment. At the end of the culture (7 days), the supernatants were harvested for cytokine measurement, while the resulting DCs were analyzed for the surface markers by flow cytometry, the antigen uptake by phagocytosis of FITC-dextran, and the antigenpresenting capacity by allogeneic MLR.

Figure 23:
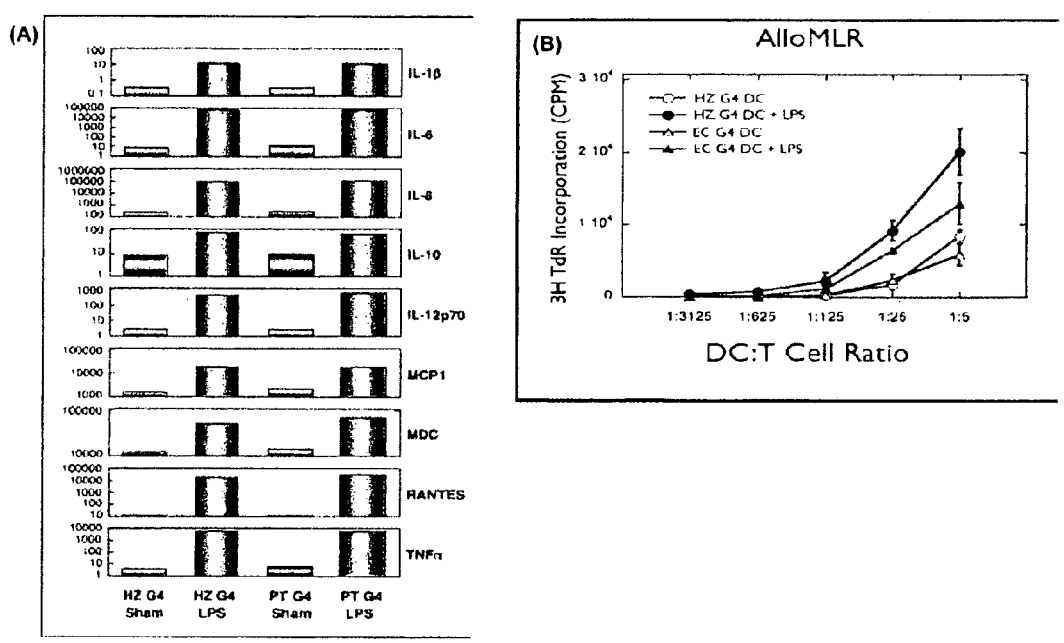
FIG. 23: Cost and time-saving G4 protocol for dendritic cell differentiation. (A) The profile of DC generation of selected cytokines and chemokines demonstrated that DCs generated in HZ G4 DC medium (5 ng/ml GM-CSF (authentic human, expressed in human cells) and IL-4 (authentic human, expressed in human cells) without medium replacement) showed a similar profile to DCs in EC G4 DC medium (50 ng/ml *E. coli* GM-CSF and IL-4 with twice medium replacement) before and after maturation by lipopolysaccharide (LPS). (B) Allogenic MLR of DCs generated and matured in HZ G4 DC medium appeared to be even better than DCs in EC G4 DC medium.

The profile of DC generation of selected cytokines and chemokines was measured by Pierce Cytokine Array. The data indicate that DCs generated in the presence of HZ G4 DC (5 ng/ml without medium replacement) showed a similar profile of cytokines and chemokines as DCs generated in the presence of EC G4 DC (50 ng/ml with medium replacement) before and after maturation (FIG. 23A). DCs differentiated in the presence of HZ G4 DC or EC G4 DC before or after LPS maturation were cultured in triplicate with allogeneic human peripheral blood T cells at various ratios for 5 days. The cultures were pulsed with 3H-TdR (0.5 uCi/well) for the last 18 h before cell harvest. The proliferation of T lymphocytes was measured by beta scintillation counting. As shown by FIG. 23B, DCs differentiated in the presence of either HZ G4 DC or EC G4 DC showed similar low capacities to stimulated the proliferation of allogeneic T cells in particular when DC:T ratio was low. After LPS induced maturation, DCs differentiated under both conditions increased their capacity to stimulate the proliferation of allogeneic T cells. DCs generated in the presence of HZ G4 DC seemed to be even better than DCs generated in the presence of EC G4 DC in this regard (FIG. 23B). Therefore, DCs differentiated in the presence of HZ G4 DC had similar or better antigen-presenting capacity than DCs differentiated in the presence of EC G4 DC.

Example 16

Authentic Noggin

Figure 24:
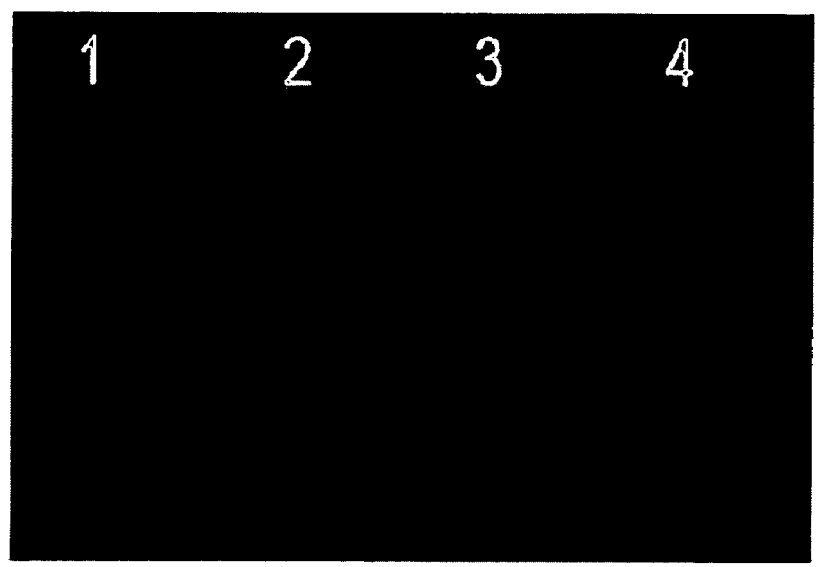
FIG. 24: Noggin Expressed in Human Cells of the Present Invention Treated HES Cells Are OCT3/4 Positive. Treated with recombinantly-produced, authentic human Noggin at 10-20 pg/ml, human embryonic stem (hES) cells consistently expressed Oct3/4, which is a marker for undifferentiated ES cells. Western blot analysis of Oct3/4. 1, Negative control; 2, Positive control; 3, authentic Noggin 10 pg/ml treatment; 4, authentic Noggin 20 pg/ml treatment.

Noggin is a secreted homodimeric glycoprotein that is an antagonist of bone morphogenetic proteins (BMPs). During culture of human embryonic stem (hES) cells without feeder layer or conditioned medium (but with addition of FGF basic), the addition of Noggin allows the stem cells to maintain their undifferentiated, pluripotent state. Commercially available Noggin products are produced in a variety of forms none of which are authentic: non-glycosylated protein expressed in *E. coli*; glycosylated Fc-fusion protein expresed in NSO, for example. Recombinantly-produced, authentic human Noggin has herein been produced in a stable, engineered human 293 cell expression system. The protein is expressed as an authentic glycosylated, disulfide-linked dimer. The recombinantly-produced, authentic human homodimer Noggin expresses so effectively and consistently Oct3/4, which is a marker for undifferentiated hES cells, as at the concentration of 10 pg/ml treatment (FIG. 24, lane 3) and 20 pg/ml treatment (FIG. 24, lane 4) compared to negative and positive controls (FIG. 24, lanes 1 and 2). See Wang et al., Biochem. Biophys. Res. Comm., 330:934-942 (2005), and Itsykson et al., Mol. Cell. Neurosci. 30:24-36 (2005), which are each incorporated herein by reference.

Example 17

Monoclonal Antibodies to Authentic G-CSF

Cytokines produced in *E. coli* are not glycosylated and may expose cryptic or normally hidden epitopes. Similarly, cytokines produced in SF9 or CHO cells have post-translational modifications which are not human-like. Because of these factors, antibodies may have different affinities depending on whether they were created from human cell expressed protein antigens or non-human cell expressed protein antigens.

Figure 25:
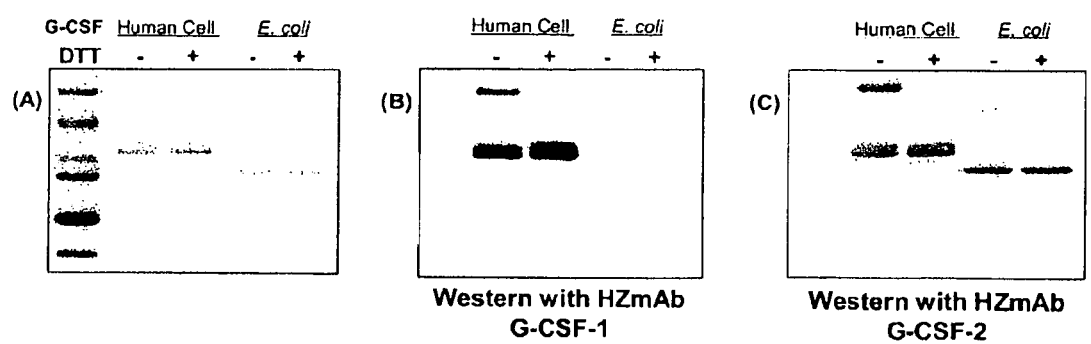
FIG. 25: G-CSF antibodies will more accurately monitor human biology. Recombinant human G-CSF expressed from human cells according to the present invention is authentically glycosylated and presents unique epitopes that may not exist in the protein expressed from non-human cells (A). In Western blot a monoclonal antibody (HZ mAb1) raised against a unique epitope recognize only human cell G-CSF (B) while another antibody (HZ mAb2) against a common epitope recognize both (C).
Figure 26:
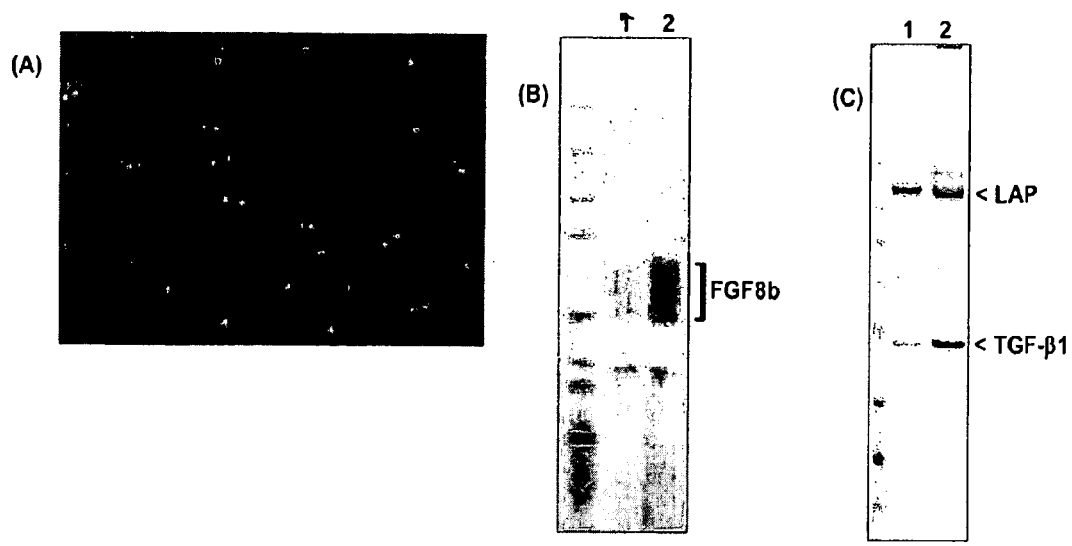
FIG. 26: New Cell Line (HZ-293TS). (A) New cell line HZ-293TS, a 293T cell line adapted to suspension culture in a serum-free chemically defined medium. (B) Comparison of FGF8b expression level from 1, 293T and 2, HZ-293TS. (C) Comparison of TGF-β1 expression level from 1, 293T and 2, HZ-293TS. In both cases protein expression level was 2-fold higher from HZ-293TS cell line compare to that from 293T cell line.

Several monoclonal antibodies against G-CSF from the inventive human cell expression system have been raised which have a higher apparent molecular mass of 22-25 kD due to its glycosylation compare to that of 18 kD from *E. coli* on SDS-PAGE gel (FIG. 25A). Among the monoclonal antibodies HZmAb G-CSF-1 recognizes only G-CSF from the human cells and not G-CSF from *E. coli* (FIG. 25B) whereas HZmAb G-CSF-2 recognizes both G-CSFs (FIG. 25C). These results indicate that recombinant cytokines from the human cell expression system are highly preferred antigens to raise antibodies that can selectively detect unique epitope sites of human serum cytokines as well as to use as standards in ELISA assays.

Example 18

Other Proteins that can be Expressed in the human Cell System of the Present Invention The present inventive human expression system is not limited to the expression of human cytokines. Human proteins other than human cytokines can be expressed in the stable human cell expression system of the present invention. For instance, human kinases, and human phosphatases, and other human proteins and enzymes can also be authentically expressed in the present human cell expression system to produce recombinant, authentic human-like kinases, phosphatases, proteins, and enzymes.

Due to their critical role in intracellular communication, dysregulation of protein kinases has been implicated in as many as 400 human diseases including cancer, diabetes, heart disease, neurological disorders and rheumatoid arthritis. Hence, protein kinases are important for drug design and screening. Currently, kinases are predominantly produced in non-human cells (e.g. *E. coli* or insect cells) many of which require protein truncation and/or in vitro activation steps, due to the limitations of the expression system. It is possible, according to the present invention to express human protein kinases which are full length and in vivo activated. Using p38α as an example, it has been demonstrated herein that the properties and inhibition profiles of the human protein kinases produced in the human cell system of the present invention are differentiated from versions of the same kinase that were produced in non-human cell systems.

Recombinantly-produced, authentic human p38a was produced and activated in human cells in the presence of arsenite according to the present invention. Sample kinases from Vendor A and B were expressed and purified from *E. coli*, in vitro activated by MKK6, and repurified. SDS PAGE analysis shows that p38a produced in the human cell expreseeion system is pure with a dominant band of 60 kD and minor band of endogenous human GST of 23 kD. This was confirmed by MS analysis and no other contaminant proteins were found. The Km.ATP for the authentic p38α is 109±12 µM while the Km was 212±26 µM for the Vendor preparation. The Km of 120 µM was found with Vendor B enzyme. The IC50 values were determined for 14 known kinase inhibitors. See Table 4. While the IC50 values for SB-202190 (the known p38a selective inhibitor) for both p38α preparations were similar (0.02 µM and 0.03 µM respectively), there is clearly a difference in the sensitivity to the inhibitors between the two preparations. See Table 4. The Vendor A preparation was only sensitive to AMP-PNP (a non-hydrolysable ATP analog). Yet, the protein was 7-fold less sensitive than p38α, which is consistent with its higher Km. p38α on the other hand, had measurable IC50 values against staurosporine, K252a, Ro 31-8220, KT5720, and SB-202190. The inhibition profile of Vendor A kinase is comparable to that of Vendor B. See Table 4.

Tables

TABLE 1

| Expression system | E. coli | Insect cell | CHO cell | Human cell |
|---|---|---|---|---|
| Protein folding | + | ++ | +++ | ++++ |
| Phosphorylation | | ++ | +++ | ++++ |
| Proteolytic processing | | + | +++ | ++++ |
| Glycosylation | − | Poor | Not human-like | Authentic |

TABLE 2

CYTOKINES AND THEIR ACTIVITIES

| Cytokine | Cell Producing | Target Cell | Function |
|---|---|---|---|
| GM-CSF | Th cells | progenitor cells | growth and differentiation of monocytes and DC |
| IL-1α | monocytes | Th cells | co-stimulation |
| IL-1β | macrophages | B cells | maturation and proliferation |
| | B cells, DC | NK cells, various | Activation, inflammation, acute phase response, fever |
| IL-2 | Th1 cells | activated T and B cells, NK cells | growth, proliferation, activation |
| IL-3 | Th cells | stem cells | growth and differentiation |
| | NK cells | mast cells | growth and histamine release |
| IL-4 | Th2 cells | activated B cells | proliferation and differentiation IgG$_1$ and IgE synthesis |
| | | macrophages | MHC Class II |
| | | T cells | proliferation |
| IL-5 | Th2 cells | activated B cells | proliferation and differentiation IgA synthesis |
| IL-6 | monocytes | activated B cells | differentiation into plasma cells |
| | macrophages | plasma cells | antibody secretion |
| | Th2 cells | stem cells | differentiation |
| | stromal cells | various | acute phase response |
| IL-7 | marrow stroma thymus stroma | stem cells | differentiation into progenitor B and T cells |
| IL-8 | macrophages endothelial cells | neutrophils | chemotaxis |
| IL-10 | Th2 cells | macrophages | cytokine production |
| | | B cells | activation |
| IL-12 | macrophages B cells | activated Tc cells | differentiation into CTL (with IL-2) |
| | | NK cells | activation |
| IFN-α | leukocytes | various | viral replication MHC I expression |
| IFN-β | fibroblasts | various | viral replication MHC I expression |
| IFN-γ | Th1 cells, Tc cells, NK cells | various | Viral replication |
| | | macrophages | MHC expression |
| | | activated B cells | Ig class switch to IgG$_{2a}$ |
| | | Th2 cells | proliferation |
| | | macrophages | pathogen elimination |
| MIP-1α | macrophages | monocytes, T cells | chemotaxis |
| MIP-1β | lymphocytes | monocytes, T cells | chemotaxis |
| TGF-β | T cells, monocytes | monocytes, macrophages | chemotaxis |
| | | activated macrophages | IL-1 synthesis |
| | | activated B cells | IgA synthesis |
| | | various | proliferation |
| TNFα | macrophages, mast cells, NK | macrophages | CAM and cytokine expression |
| | | tumor cells | cell death |
| TNF-β | Th1 and Tc cells | phagocytes | phagocytosis, NO production |
| | | tumor cells | cell death |

TABLE 3

GENE ACCESSION NUMBERS FOR EXEMPLARY CYTOKINES

| Cytokine | Gene Accession Number | Cytokine | Gene Accession Number |
| --- | --- | --- | --- |
| Erythropoietin | BC093628 | Noggin | BC034027 |
| G-CSF | NM_000759 | SCF | BC074725 |
| GM-CSF | BC113999 | Somatotropin | BC075012 |
| IL-2 | BC066255 | TGF-β1 | BC001180 |
| IL-4 | BC067514 | TNFα | BC028148 |
| IL-6 | BC015511 | VEGF165 | NM_003376 |
| M-CSF | BC021117 | | |

TABLE 4

INHIBITOR IC50 VALUES

| | Human Cell IC50 μM | E coli-I IC50 μM | E coli-II IC50 μM |
| --- | --- | --- | --- |
| Staurosporine | 0.14 | >10 | >10 |
| H-9 dihydrochloride | >10 | >10 | >10 |
| AMP-PNP | 257 | 1806 | >2000 |
| HA-1077 dihydrochlorie | >10 | >10 | >10 |
| Rottlerin | >200 | >200 | >200 |
| H89 Dihydrochloride | >10 | >10 | >10 |
| 5-iodotubercidin | >10 | >10 | >10 |
| K252a | 0.005 | >10 | >10 |
| Ro 32-0432 | >10 | >10 | >10 |
| Ro 31-8220 | 9.9 | >10 | >10 |
| GF 109203X | >10 | >10 | >10 |
| KT5720 | 5.0 | >10 | >10 |
| Imatinib mesylate | >10 | >10 | >10 |
| SB | 0.02 | 0.03 | 0.01 |

TABLE 5

LIST OF CLONED CYTOKINE GENES

| | | | |
| --- | --- | --- | --- |
| Activin A/2xINHbA | GDF5/BMP14 | IL3 | TGF β2 |
| Activin B/2xINHbB | GDF8/myostatin | IL32 | TGF β3 |
| AMH/MIS | GDF9 | IL35 | TGFβ4/LEFTY2/LeftyA |
| Artemin | GDNF | IL4 | TNF α |
| BDNF | GM-CSF | IL5 | TPOα |
| BMP15/GDF9B | HGF | IL6 | VEGF121aa |
| BMP2/BMP2A | IFN α2A | IL7 | VEGF165aa |
| BMP3/Osteogenin | IFN α2B | IL8 | WIF1 |
| BMP4/BMP2B | IFN γ | IL9 | WNT1 |
| BMP5 | IFN β1 | Inhibin A/INHa&INHbA | Wnt10A |
| BMP7/OP-1 | IGF I | Inhibin B/INHa&INHbB | Wnt10B/12 |
| β-NGF | IGF II | Inhibin C/INHa&INHbC | Wnt11 |
| Cystatin C | IGF IIvI | Inhibin E/INHa&INHbE | Wnt16 |
| Delta 1 | IGF IIv2 | LEFTY1/LeftyB | Wnt2 |
| EGF | IL10 | M-CSF | Wnt2B/13 |
| Erythropoietin (Epo) | IL11 | NODAL | Wnt3 |
| FGF acidic | ILI2 | Noggin | Wnt3A |
| FGF basic | IL15 | NT3 (neurotrophin3) | Wnt4 |
| FGF10 | IL17 | Oncostatin M | Wnt5A |
| FGF5 | IL17F | PDGF α | Wnt5B |
| FGF7 | IL1β | PDGF β | Wnt6 |
| FGF8b | IL2 | Persephin | Wnt7A |
| FLT3 ligand | IL23 | SCF | Wnt7B |
| G-CSF | IL27 | SDF1α | Wnt8B |
| GDF15 | IL28A/IFNλ2 | SHH | Wnt9A/14 |
| GDF2/BMP9 | IL28B/IFNλ3 | Somatotropin | |
| GDF3 | IL29/IFNλ1 | TGF β1 | |

Sequences (1) VEGF165
DNA sequence is SEQ ID NO: 1.
Amino acid sequence is SEQ ID NO: 2.

```
gcacccatggcagaaggagagggcagaatcatcacgaagtggtgaagttcatggatgtc
 A  P  M  A  E  G  G  Q  N  H  H  E  V  V  K  F  M  D  V tatcagcgcagctactgccatccaatcgagaccctggtggacatcttccaggagtaccct
 Y  Q  R  S  Y  C  H  P  I  E  T  L  V  D  I  F  Q  E  Y  P gatgagatcgagtacatcttcaagccatcctgtgtgcccctgatgcgatgcgggggctgc
 D  E  I  E  Y  I  F  K  P  S  C  V  P  L  M  R  C  G  G  C tgcaatgacgagggcctggagtgtgtgcccactgaggagtccaacatcaccatgcagatt
 C  N  D  E  G  L  E  C  V  P  T  E  E  S  N  I  T  M  Q  I atgcggatcaaacctcaccaaggccagcacataggagagatgagcttcctacagcacaac
 M  R  I  K  P  H  Q  G  Q  H  I  G  E  M  S  F  L  Q  H  N
```

```
aaatgtgaatgcagaccaaagaaagatagagcaagcaagaaaatccctgtgggccttgc
 K  C  E  C  R  P  K  K  D  R  A  R  Q  E  N  P  C  G  P  C tcagagcggagaaagcatttgtttgtacaagatccgcagacgtgtaaatgttcctgcaaa
 S  E  R  R  K  H  L  F  V  Q  D  P  Q  T  C  K  C  S  C  K aacacagactcgcgttgcaaggcgaggcagcttgagttaaacgaacgtacttgcagatgt
 N  T  D  S  R  C  K  A  R  Q  L  E  L  N  E  R  T  C  R  C gacaagccgaggcggtgataa
 D  K  P  R  R  -  -

(2) G-CSF
DNA sequence is SEQ ID NO: 3.
Amino acid sequence is SEQ ID NO: 4.
acccccctgggccctgccagctccctgcccagagcttcctgctcaagtgcttagagcaa
 T  P  L  G  P  A  S  S  L  P  Q  S  F  L  L  K  C  L  E  Q gtgaggaagatccagggcgatggcgcagcgctccaggagaagctgtgtgccacctacaag
 V  R  K  I  Q  G  D  G  A  A  L  Q  E  K  L  C  A  T  Y  K ctgtgccaccccgaggagctggtgctgctcggacactctctgggcatcccctgggctccc
 L  C  H  P  E  E  L  V  L  L  G  H  S  L  G  I  P  W  A  P ctgagcagctgccccagccaggccctgcagctggcaggctgcttgagccaactccatagc
 L  S  S  C  P  S  Q  A  L  Q  L  A  G  C  L  S  Q  L  H  S ggccttttcctctaccaggggctcctgcaggccctggaagggatctcccccgagttgggt
 G  L  F  L  Y  Q  G  L  L  Q  A  L  E  G  I  S  P  E  L  G cccaccttggacacactgcagctggacgtcgccgactttgccaccaccatctggcagcag
 P  T  L  D  T  L  Q  L  D  V  A  D  F  A  T  T  I  W  Q  Q atggaagaactgggaatggcccctgccctgcagcccacccagggtgccatgccggccttc
 M  E  E  L  G  M  A  P  A  L  Q  P  T  Q  G  A  M  P  A  F gcctctgctttccagcgccgggcaggaggggtcctggttgcctcccatctgcagagcttc
 A  S  A  F  Q  R  R  A  G  G  V  L  V  A  S  H  L  Q  S  F ctggaggtgtcgtaccgcgttctacgccaccttgcccagccctgataa
 L  E  V  S  Y  R  V  L  R  H  L  A  Q  P  -  -

(3) M-CSF
DNA sequence is SEQ ID NO: 5.
Amino acid sequence is SEQ ID NO: 6.
gaggaggtgtcggagtactgtagccacatgattgggagtggacacctgcagtctctgcag
 E  E  V  S  E  Y  C  S  H  M  I  G  S  G  H  L  Q  S  L  Q cggctgattgacagtcagatggagacctcgtgccaaattacatttgagtttgtagaccag
 R  L  I  D  S  Q  M  E  T  S  C  Q  I  T  F  E  F  V  D  Q gaacagttgaaagatccagtgtgctaccttaagaaggcatttctcctggtacaagacata
 E  Q  L  K  D  P  V  C  Y  L  K  K  A  F  L  L  V  Q  D  I atggaggacaccatgcgcttcagagataacacccccaatgccatcgccattgtgcagctg
 M  E  D  T  M  R  F  R  D  N  T  P  N  A  I  A  I  V  Q  L caggaactctctttgaggctgaagagctgcttcaccaaggattatgaagagcatgacaag
 Q  E  L  S  L  R  L  K  S  C  F  T  K  D  Y  E  E  H  D  K gcctgcgtccgaactttctatgagacacctctccagttgctggagaaggtcaagaatgtc
 A  C  V  R  T  F  Y  E  T  P  L  Q  L  L  E  K  V  K  N  V tttaatgaaacaaagaatctccttgacaaggactggaatatttcagcaagaactgcaac
 F  N  E  T  K  N  L  L  D  K  D  W  N  I  F  S  K  N  C  N aacagctttgctgaatgctccagccaaggccatgagaggcagtccgagggatcctgataa
 N  S  F  A  E  C  S  S  Q  G  H  E  R  Q  S  E  G  S  -  -

(4) IL-2
DNA sequence is SEQ ID NO: 7.
Amino acid sequence is SEQ ID NO: 8.
gcacctacttcaagttctacaaagaaaacacagctacaactggagcatttactgctggat
 A  P  T  S  S  S  T  K  K  T  Q  L  Q  L  E  H  L  L  L  D ttacagatgattttgaatggaattaataattacaagaatcccaaactcaccaggatgctc
 L  Q  M  I  L  N  G  I  N  N  Y  K  N  P  K  L  T  R  M  L acatttaagttttacatgcccaagaaggccacagaactgaaacatctccagtgtctagaa
 T  F  K  F  Y  M  P  K  K  A  T  E  L  K  H  L  Q  C  L  E
```

```
gaagaactcaaacctctggaggaagtgctaaatttagctcaaagcaaaaactttcactta
 E  E  L  K  P  L  E  E  V  L  N  L  A  Q  S  K  N  F  H  L agacccagggacttaatcagcaatatcaacgtaatagttctggaactaaagggatctgaa
 R  P  R  D  L  I  S  N  I  N  V  I  V  L  E  L  K  G  S  E acaacattcatgtgtgaatatgctgatgagacagcaaccattgtagaatttctgaacaga
 T  T  F  M  C  E  Y  A  D  E  T  A  T  I  V  E  F  L  N  R tggattaccttttgtcaaagcatcatctcaacactgacttgataa
 W  I  T  F  C  Q  S  I  I  S  T  L  T  -  -

(5) Somatotropin
DNA sequence is SEQ ID NO: 9.
Amino acid sequence is SEQ ID NO: 10.
ttcccaaccattcccttatccaggcttttgacaacgctatgctccgcgcccatcgtctg
 F  P  T  I  P  L  S  R  L  F  D  N  A  M  L  R  A  H  R  L caccagctggcctttgacacctaccaggagtttgaagaagcctatatcccaaaggaacag
 H  Q  L  A  F  D  T  Y  Q  E  F  E  E  A  Y  I  P  K  E  Q aagtattcattcctgcagaaccccagacctccctctgtttctcagagtctattccgaca
 K  Y  S  F  L  Q  N  P  Q  T  S  L  C  F  S  E  S  I  P  T ccctccaacagggaggaaacacaacagaaatccaacctagagctgctccgcatctccctg
 P  S  N  R  E  E  T  Q  Q  K  S  N  L  E  L  L  R  I  S  L ctgctcatccagtcgtggctggagcccgtgcagttcctcaggagtgtcttcgccaacagc
 L  L  I  Q  S  W  L  E  P  V  Q  F  L  R  S  V  F  A  N  S ctggtgtacggcgcctctgacagcaacgtctatgacctcctaaaggacctagaggaaggc
 L  V  Y  G  A  S  D  S  N  V  Y  D  L  L  K  D  L  E  E  G atccaaacgctgatggggaggctggaagatggcagcccccggactgggcagatcttcaag
 I  Q  T  L  M  G  R  L  E  D  G  S  P  R  T  G  Q  I  F  K cagacctacagcaagttcgacacaaactcacacaacgatgacgcactactcaagaactac
 Q  T  Y  S  K  F  D  T  N  S  H  N  D  D  A  L  L  K  N  Y gggctgctctactgcttcaggaaggacatggacaaggtcgagacattcctgcgcatcgtg
 G  L  L  Y  C  F  R  K  D  M  D  K  V  E  T  F  L  R  I  V cagtgccgctctgtggagggcagctgtggcttctagtaa
 Q  C  R  S  V  E  G  S  C  G  F  -  -

(6) TGFb1
DNA sequence is SEQ ID NO: 11.
Amino acid sequence is SEQ ID NO: 12.
ctatccacctgcaagactatcgacatggagctggtgaagcggaagcgcatcgaggccatc
 L  S  T  C  K  T  I  D  M  E  L  V  K  R  K  R  I  E  A  I cgcggccagatcctgtccaagctgcggctcgccagccccccgagccaggggaggtgccg
 R  G  Q  I  L  S  K  L  R  L  A  S  P  P  S  Q  G  E  V  P cccggcccgctgcccgaggccgtgctcgccctgtacaacagcacccgcgaccgggtggcc
 P  G  P  L  P  E  A  V  L  A  L  Y  N  S  T  R  D  R  V  A ggggagagtgcagaaccggagcccgagcctgaggccgactactacgccaaggaggtcacc
 G  E  S  A  E  P  E  P  E  P  E  A  D  Y  Y  A  K  E  V  T cgcgtgctaatggtggaaacccacaacgaaatctatgacaagttcaagcagagtacacac
 R  V  L  M  V  E  T  H  N  E  I  Y  D  K  F  K  Q  S  T  H agcatatatatgttcttcaacacatcagagctccgagaagcggtacctgaaccgtgttg
 S  I  Y  M  F  F  N  T  S  E  L  R  E  A  V  P  E  P  V  L ctctcccgggcagagctgcgtctgctgaggctcaagttaaaagtggagcagcacgtggag
 L  S  R  A  E  L  R  L  L  R  L  K  L  K  V  E  Q  H  V  E ctgtaccagaaatacagcaacaattcctggcgatacctcagcaaccggctgctggcaccc
 L  Y  Q  K  Y  S  N  N  S  W  R  Y  L  S  N  R  L  L  A  P agcgactcgccagagtggttatcttttgatgtcaccggagttgtgcggcagtggttgagc
 S  D  S  P  E  W  L  S  F  D  V  T  G  V  V  R  Q  W  L  S cgtggagggaaattgagggctttcgccttagcgcccactgctcctgtgacagcagggat
 R  G  G  E  I  E  G  F  R  L  S  A  H  C  S  C  D  S  R  D aacacactgcaagtggacatcaacgggttcactaccggccgccgaggtgacctggccacc
 N  T  L  Q  V  D  I  N  G  F  T  T  G  R  R  G  D  L  A  T
```

-continued

```
attcatggcatgaaccggcctttcctgcttctcatggccaccccgctggagagggcccag
 I  H  G  M  N  R  P  F  L  L  L  M  A  T  P  L  E  R  A  Q catctgcaaagctcccggcaccgccgagccctggacaccaactattgcttcagctccacg
 H  L  Q  S  S  R  H  R  R  A  L  D  T  N  Y  C  F  S  S  T gagaagaactgctgcgtgcggcagctgtacattgacttccgcaaggacctcggctggaag
 E  K  N  C  C  V  R  Q  L  Y  I  D  F  R  K  D  L  G  W  K tggatccacgagcccaagggctaccatgccaacttctgcctcgggcctgcccctacatt
 W  I  H  E  P  K  G  Y  H  A  N  F  C  L  G  P  C  P  Y  I tggagcctggacacgcagtacagcaaggtcctggccctgtacaaccagcataacccgggc
 W  S  L  D  T  Q  Y  S  K  V  L  A  L  Y  N  Q  H  N  P  G gcctcggcggcgccgtgctgcgtgccgcaggcgctggagccgctgcccatcgtgtactac
 A  S  A  A  P  C  C  V  P  Q  A  L  E  P  L  P  I  V  Y  Y gtgggccgcaagcccaaggtggagcagctgtccaacatgatcgtgcgctcctgcaagtgc
 V  G  R  K  P  K  V  E  Q  L  S  N  M  I  V  R  S  C  K  C agctgataa
 S  -  -
```

(7) TNFα
DNA sequence is SEQ ID NO: 13.
Amino acid sequence is SEQ ID NO: 14.

```
gtcagatcatcttctcgaaccccgagtgacaagcctgtagcccatgttgtagcaaaccct
 V  R  S  S  S  R  T  P  S  D  K  P  V  A  H  V  V  A  N  P caagctgaggggcagctccagtggctgaaccgccgggccaatgcccctcctggccaatggc
 Q  A  E  G  Q  L  Q  W  L  N  R  R  A  N  A  L  L  A  N  G gtggagctgagagataaccagctggtggtgccatcagagggcctgtacctcatctactcc
 V  E  L  R  D  N  Q  L  V  V  P  S  E  G  L  Y  L  I  Y  S caggtcctcttcaagggccaaggctgcccctccacccatgtgctcctcacccacaccatc
 Q  V  L  F  K  G  Q  G  C  P  S  T  H  V  L  L  T  H  T  I agccgcatcgccgtctcctaccagaccaaggtcaacctcctctctgccatcaagagcccc
 S  R  I  A  V  S  Y  Q  T  K  V  N  L  L  S  A  I  K  S  P tgccagagggagacccagagggggctgaggccaagccctggtatgagcccatctatctg
 C  Q  R  E  T  P  E  G  A  E  A  K  P  W  Y  E  P  I  Y  L ggaggggtcttccagctggagaagggtgaccgactcagcgctgagatcaatcggcccgac
 G  G  V  F  Q  L  E  K  G  D  R  L  S  A  E  I  N  R  P  D tatctcgactttgccgagtctgggcaggtctactttgggatcattgccctgtgataa
 Y  L  D  F  A  E  S  G  Q  V  Y  F  G  I  I  A  L  -  -
```

(8) IL6
DNA sequence is SEQ ID NO: 15.
Amino acid sequence is SEQ ID NO: 16.

```
gccccagtaccccaggagaagattccaaagatgtagccgccccacacagacagccactc
 A  P  V  P  P  G  E  D  S  K  D  V  A  A  P  H  R  Q  P  L acctcttcagaacgaattgacaaacaaattcggtacatcctcgacggcatctcagccctg
 T  S  S  E  R  I  D  K  Q  I  R  Y  I  L  D  G  I  S  A  L agaaaggagacatgtaacaagagtaacatgtgtgaaagcagcaaagaggcactggcagaa
 R  K  E  T  C  N  K  S  N  M  C  E  S  S  K  E  A  L  A  E aacaacctgaaccttccaaagatggctgaaaaagatggatgcttccaatctggattcaat
 N  N  L  N  L  P  K  M  A  E  K  D  G  C  F  Q  S  G  F  N gaggagacttgcctggtgaaaatcatcactggtcttttggagtttgaggtatacctagag
 E  E  T  C  L  V  K  I  I  T  G  L  L  E  F  E  V  Y  L  E tacctccagaacagatttgagagtagtgaggaacaagccagagctgtgcagatgagtaca
 Y  L  Q  N  R  F  E  S  S  E  E  Q  A  R  A  V  Q  M  S  T aaagtcctgatccagttcctgcagaaaaaggcaaagaatctagatgcaataaccacccct
 K  V  L  I  Q  F  L  Q  K  K  A  K  N  L  D  A  I  T  T  P gacccaaccacaaatgccagcctgctgacgaagctgcaggcacagaaccagtggctgcag
 D  P  T  T  N  A  S  L  L  T  K  L  Q  A  Q  N  Q  W  L  Q gacatgacaactcatctcattctgcgcagctttaaggagttcctgcagtccagcctgagg
 D  M  T  T  H  L  I  L  R  S  F  K  E  F  L  Q  S  S  L  R
```

```
gctcttcggcaaatgtagtaa
 A  L  R  Q  M  -  -

(9) Erythropoietin (Epo)
DNA sequence is SEQ ID NO: 17.
Amino acid sequence is SEQ ID NO: 18.
gccccaccacgcctcatctgtgacagccgagtcctggagaggtacctcttggaggccaag
 A  P  P  R  L  I  C  D  S  R  V  L  E  R  Y  L  L  E  A  K gaggccgagaatatcacgacgggctgtgctgaacactgcagcttgaatgagaatatcact
 E  A  E  N  I  T  T  G  C  A  E  H  C  S  L  N  E  N  I  T gtcccagacaccaaagttaatttctatgcctggaagaggatggaggtcgggcagcaggcc
 V  P  D  T  K  V  N  F  Y  A  W  K  R  M  E  V  G  Q  Q  A gtagaagtctggcagggcctggccctgctgtcggaagctgtcctgcggggccaggccctg
 V  E  V  W  Q  G  L  A  L  L  S  E  A  V  L  R  G  Q  A  L ttggtcaactcttcccagccgtgggagcccctgcagctgcatgtggataaagccgtcagt
 L  V  N  S  S  Q  P  W  E  P  L  Q  L  H  V  D  K  A  V  S ggccttcgcagcctcaccactctgcttcgggctctgggagcccagaaggaagccatctcc
 G  L  R  S  L  T  T  L  L  R  A  L  G  A  Q  K  E  A  I  S cctccagatgcggcctcagctgctccactccgaacaatcactgctgacactttccgcaaa
 P  P  D  A  A  S  A  A  P  L  R  T  I  T  A  D  T  F  R  K ctcttccgagtctactccaatttcctccggggaaagctgaagctgtacacaggggaggcc
 L  F  R  V  Y  S  N  F  L  R  G  K  L  K  L  Y  T  G  E  A tgcaggacaggggacagatgataa
 C  R  T  G  D  R  -  -

(10) GM-CSF
DNA sequence is SEQ ID NO: 19.
Amino acid sequence is SEQ ID NO: 20.
gcacccgcccgctcgcccagccccagcacgcagccctgggagcatgtgaatgccatccag
 A  P  A  R  S  P  S  P  S  T  Q  P  W  E  H  V  N  A  I  Q gaggccggcgtctcctgaacctgagtagagacactgctgctgagatgaatgaaacagta
 E  A  R  R  L  L  N  L  S  R  D  T  A  A  E  M  N  E  T  V gaagtcatctcagaaatgtttgacctccaggagccgacctgcctacagacccgcctggag
 E  V  I  S  E  M  F  D  L  Q  E  P  T  C  L  Q  T  R  L  E ctgtacaagcagggcctgcggggcagcctcaccaagctcaagggccccttgaccatgatg
 L  Y  K  Q  G  L  R  G  S  L  T  K  L  K  G  P  L  T  M  M gccagccactacaagcagcactgccctccaaccccggaaacttcctgtgcaacccagatt
 A  S  H  Y  K  Q  H  C  P  P  T  P  E  T  S  C  A  T  Q  I atcacctttgaaagtttcaaagagaacctgaaggactttctgcttgtcatccccttgac
 I  T  F  E  S  F  K  E  N  L  K  D  F  L  L  V  I  P  F  D tgctgggagccagtccaggagtgataa
 C  W  E  P  V  Q  E  -  -

(11) IL4
DNA sequence is SEQ ID NO: 21.
Amino acid sequence is SEQ ID NO: 22.
cacaagtgcgatatcaccttacaggagatcatcaaaactttgaacagcctcacagagcag
 H  K  C  D  I  T  L  Q  E  I  I  K  T  L  N  S  L  T  E  Q aagactctgtgcaccgagttgaccgtaacagacatctttgctgcctccaagaacacaact
 K  T  L  C  T  E  L  T  V  T  D  I  F  A  A  S  K  N  T  T gagaaggaaaccttctgcagggctgcgactgtgctccggcagttctacagccaccatgag
 E  K  E  T  F  C  R  A  A  T  V  L  R  Q  F  Y  S  H  H  E aaggacactcgctgcctgggtgcgactgcacagcagttccacaggcacaagcagctgatc
 K  D  T  R  C  L  G  A  T  A  Q  Q  F  H  R  H  K  Q  L  I cgattcctgaaacggctcgacaggaacctctggggcctggcgggcttgaattcctgtcct
 R  F  L  K  R  L  D  R  N  L  W  G  L  A  G  L  N  S  C  P gtgaaggaagccaaccagagtacgttggaaaacttcttggaaaggctaaagacgatcatg
 V  K  E  A  N  Q  S  T  L  E  N  F  L  E  R  L  K  T  I  M agagagaaatattcaaagtgttcgagctgataa
 R  E  K  Y  S  K  C  S  S  -  -
```

(12) Noggin
DNA sequence is SEQ ID NO: 23.
Amino acid sequence is SEQ ID NO: 24.

```
cagcactatctccacatccgcccggcacccagcgacaacctgcccctggtggacctcatc
 Q  H  Y  L  H  I  R  P  A  P  S  D  N  L  P  L  V  D  L  I gaacacccagaccctatctttgaccccaaggaaaaggatctgaacgagacgctgctgcgc
 E  H  P  D  P  I  F  D  P  K  E  K  D  L  N  E  T  L  L  R tcgctgctcggggccactacgacccaggcttcatggccacctcgcccccgaggaccgg
 S  L  L  G  G  H  Y  D  P  G  F  M  A  T  S  P  P  E  D  R cccggcggggcggggtgcagctgggggcgcggaggacctggcggagctggaccagctg
 P  G  G  G  G  A  A  G  G  A  E  D  L  A  E  L  D  Q  L ctgcggcagcggccgtcggggccatgccgagcgagatcaaagggctagagttctccgag
 L  R  Q  R  P  S  G  A  M  P  S  E  I  K  G  L  E  F  S  E ggcttggcccagggcaagaagcagcgcctaagcaagaagctgcggaggaagttacagatg
 G  L  A  Q  G  K  K  Q  R  L  S  K  K  L  R  R  K  L  Q  M tggctgtggtcgcagacattctgccccgtgctgtacgcgtggaacgacctgggcagccgc
 W  L  W  S  Q  T  F  C  P  V  L  Y  A  W  N  D  L  G  S  R ttttggccgcgctacgtgaaggtgggcagctgcttcagtaagcgctcgtgctccgtgccc
 F  W  P  R  Y  V  K  V  G  S  C  F  S  K  R  S  C  S  V  P gagggcatggtgtgcaagccgtccaagtccgtgcacctcacggtgctgcggtggcgctgt
 E  G  M  V  C  K  P  S  K  S  V  H  L  T  V  L  R  W  R  C cagcggcgcgggggccagcgctgcggctggattcccatccagtaccccatcatttccgag
 Q  R  R  G  G  Q  R  C  G  W  I  P  I  Q  Y  P  I  I  S  E tgcaagtgctcgtgctagtaa
 C  K  C  S  C  -  -
```

(13) SCF
DNA sequence is SEQ ID NO: 25.
Amino acid sequence is SEQ ID NO: 26.

```
gaagggatctgcaggaatcgtgtgactaataatgtaaaagacgtcactaaattggtggca
 E  G  I  C  R  N  R  V  T  N  N  V  K  D  V  T  K  L  V  A aatcttccaaaagactacatgataaccctcaaatatgtcccgggatggatgttttgcca
 N  L  P  K  D  Y  M  I  T  L  K  Y  V  P  G  M  D  V  L  P agtcattgttggataagcgagatggtagtacaattgtcagacagcttgactgatcttctg
 S  H  C  W  I  S  E  M  V  V  Q  L  S  D  S  L  T  D  L  L gacaagttttcaaatatttctgaaggcttgagtaattattccatcatagacaaacttgtg
 D  K  F  S  N  I  S  E  G  L  S  N  Y  S  I  I  D  K  L  V aatatagtggatgaccttgtggagtgcgtgaaagaaaactcatctaaggatctaaaaaaa
 N  I  V  D  D  L  V  E  C  V  K  E  N  S  S  K  D  L  K  K tcattcaagagcccagaacccaggctctttactcctgaagaattctttagaatttttaat
 S  F  K  S  P  E  P  R  L  F  T  P  E  E  F  F  R  I  F  N agatccattgatgccttcaaggactttgtagtggcatctgaaactagtgattgtgtggtt
 R  S  I  D  A  F  K  D  F  V  V  A  S  E  T  S  D  C  V  V tcttcaacattaagtcctgagaaagattccagagtcagtgtcacaaaaccatttatgtta
 S  S  T  L  S  P  E  K  D  S  R  V  S  V  T  K  P  F  M  L ccccctgttgcagccagctcccttaggaatgacagcagtagcagtaataggaaggccaaa
 P  P  V  A  A  S  S  L  R  N  D  S  S  S  S  N  R  K  A  K aatccccctggagactccagcctacactgataa
 N  P  P  G  D  S  S  L  H  -  -
```

Human CMV immediate early (IE) enhancer from a CMV vector
SEQ ID NO: 27
GTTGACATTGATTATTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAACGACCCCCGCCCATTGAC
GTCAATAATGACGTATGTTCCCATAGTAACGCCAATAGGGACTTTCCATTGACGTCAATGGGTGGACTATT
TACGGTAAACGCCAATAGGGACTTTCCATTGACGTCAATGGGTGGACTATTTACGGTAAACTGCCCACTTGG
CAGTACATCAAGTGTATCATATGCCAAGTACGCCCCCTATTGACGTCAATGACGGTAAATGGCCCGCCTGG
CATTATGCCCAGTACATGACCTTATGGGACTTTCCTACTTGGCAGTACATCTACGTATTAGTCATCGCTAT
TACCATGG Human beta-actin promoter
SEQ ID NO: 28

```
CCGGGCCCAGCACCCCAAGGCGGCCAACGCCAAAACTCTCCCTCCTCCTCTTCCTCAATCTCGCTCTCGCT
CTTTTTTTTTTTCGCAAAAGGAGGGGAGAGGGGGTAAAAAAATGCTGCACTGTGCGGCGAAGCCGGTGAGT
GAGCGGCGCGGGGCCAATCAGCGTGCGCCGTTCCGAAAGTTGCCTTTTATGGCTCGAGCGGCCGCGGCGGC
GCCCTATAAAACCCAGCGGCGCGACGCGCCACCACCGCCGAGACCGCGTCCGCCCCGCGAGCACAGAGCCT
CGCCTTTGCCGATCCGCCGCCCGTCCACACCCGCCGCCAGGTAAGCCCGGCCAGCCGACCGGGGCAGGCGG
CTCACGGCCCGGCCGCAGGCGGCCGCGGCCCCTTCGCCCGTGCAGAGCCGCCGTCTGGGCCGCAGCGGGGG
GCGCATGGGGGGGAACCGGACCGCCGTGGGGGGCGCGGGAGAAGCCCCTGGGCCTCCGGAGATGGGGGAC
ACCCCACGCCAGTTCGGAGGCGCGAGGCCGCGCTCGGGAGGCGCGCTCCGGGGGTGCCGCTCTCGGGCGG
GGGCAACCGGCGGGGTCTTTGTCTGAGCCGGGCTCTTGCCAATGGGGATCGCAGGGTGGGCGCGGAGC
CCCCGCCAGGCCCGGTGGGGGCTGGGGCGCCATTGCGCGTGCGCGCTGGTCCTTTGGGCGCTAACTGCGTG
CGCGCTGGGAATTGGCGCTAATTGCGCGTGCGCGCTGGGACTCAAGGCGCTAACTGCGCGTGCGTTCTGGG
GCCCGGGGTGCCGCGGCCTGGGCTGGGGCGAAGGCGGGCTCGGCCGGAAGGGGTGGGGTCGCCGCGGCTCC
CGGGCGCTTGCGCGCACTTCCTGCCCGAGCCGCTGGCCGCCCGAGGGTGTGGCCGCTGCGTGCGCGCGCGC
CGACCCGGCGCTGTTTGAACCGGGCGGAGGCGGGGCTGGCGCCCGGTTGGGAGGGGGTTGGGGCCTGGCTT
CCTGCCGCGCGCCGCGGGGACGCCTCCGACCAGTGTTTGCCTTTTATGGTAATAACGCGGCCGGCCCGGCT
TCCTTTGTCCCCAATCTGGGCGCGCGCCGGCGCCCCCTGGCGGCCTAAGGACTCGGCGCGCCGGAAGTGGC
CAGGGCGGGGGCGACCTCGGCTCACAGCGCGCCCGGCTATTCTCGCAG

Human beta-globin intron
SEQ ID NO: 29
CTTTTGCTAATCATGTTCATACCTCTTATCTTCCTCCCACAGCTCCTGGGCAACGTGCTGGTCTGTGTGCT
GGCCCATCACTTTGGCAAAGAATTC Human fibrinogen alpha chain signal peptide (cleavage site is between
nucleotides t and g of tgac at the 3'-end)
SEQ ID NO: 30
atgttttccatgaggatcgtctgcctggtcctaagtgtggtgggcacagcatggactgac
 M  F  S  M  R  I  V  C  L  V  L  S  V  V  G  T  A  W  T  D Human immunoglobulin superfamily member 8 precursor signal peptide
(cleavage site is between nucleotides c and g of cgac at the 3'-end)
SEQ ID NO: 31
atgggcgccctcaggcccacgctgctgccgccttcgctgccgctgctgctgctgctaatg
 M  G  A  L  R  P  T  L  L  P  P  S  L  P  L  L  L  L  L  M ctaggaatgggatgctgggccgac
 L  G  M  G  C  W  A  D HumanZyme vector-1
SEQ ID NO: 32
GTTGACATTGATTATTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAACGACCCCCGCCCATTGAC
GTCAATAATGACGTATGTTCCCATAGTAACGCCAATAGGGACTTTCCATTGACGTCAATGGGTGGACTATT
TACGGTAACGCCAATAGGGACTTTCCATTGACGTCAATGGGTGGACTATTTACGGTAAACTGCCCACTTGG
CAGTACATCAAGTGTATCATATGCCAAGTACGCCCCCTATTGACGTCAATGACGGTAAATGGCCCGCCTGG
CATTATGCCCAGTACATGACCTTATGGGACTTTCCTACTTGGCAGTACATCTACGTATTAGTCATCGCTAT
TACCATGGCCGGGCCCAGCACCCCAAGGCGGCCAACGCCAAAACTCTCCCTCCTCCTCTTCCTCAATCTCG
CTCTCGCTCTTTTTTTTTTTCGCAAAAGGAGGGGAGAGGGGGTAAAAAAATGCTGCACTGTGCGGCGAAGC
CGGTGAGTGAGCGGCGCGGGGCCAATCAGCGTGCGCCGTTCCGAAAGTTGCCTTTTATGGCTCGAGCGGCC
GCGGCGGCGCCCTATAAAACCCAGCGGCGCGACGCGCCACCACCGCCGAGACCGCGTCCGCCCCGCGAGCA
CAGAGCCTCGCCTTTGCCGATCCGCCGCCCGTCCACACCCGCCGCCAGGTAAGCCCGGCCAGCCGACCGGG
GCAGGCGGCTCACGGCCCGGCCGCAGGCGGCCGCGGCCCCTTCGCCCGTGCAGAGCCGCCGTCTGGGCCGC
AGCGGGGGCGCATGGGGGGGAACCGGACCGCCGTGGGGGGCGCGGGAGAAGCCCCTGGGCCTCCGGAGA
TGGGGGACACCCCACGCCAGTTCGGAGGCGCGAGGCCGCGCTCGGGAGGCGCGCTCCGGGGGTGCCGCTCT
CGGGGCGGGGGCAACCGGCGGGGTCTTTGTCTGAGCCGGGCTCTTGCCAATGGGGATCGCAGGGTGGGCGC
GGCGAGCCCCCGCCAGGCCCGGTGGGGGCTGGGGCGCCATTGCGCGTGCGCGCTGGTCCTTTGGGCGCTA
ACTGCGTGCGCGCTGGGAATTGGCGCTAATTGCGCGTGCGCGCTGGGACTCAAGGCGCTAACTGCGCGTGC
GTTCTGGGGCCCGGGGTGCCGCGGCCTGGGCTGGGCGAAGGCGGGCTCGGCCGGAAGGGGTGGGGTCGCC
GCGGCTCCCGGGCGCTTGCGCGCACTTCCTGCCCGAGCCGCTGGCCGCCCGAGGGTGTGGCCGCTGCGTGC
GCGCGCGCCGACCCGGCGCTGTTTGAACCGGGCGGAGGCGGGGCTGGCGCCCGGTTGGGAGGGGGTTGGGG
CCTGGCTTCCTGCCGCGCGCCGCGGGGACGCCTCCGACCAGTGTTTGCCTTTTATGGTAATAACGCGGCCG
GCCCGGCTTCCTTTGTCCCCAATCTGGGCGCGCGCCGGCGCCCCCTGGCGGCCTAAGGACTCGGCGCGCCG
GAAGTGGCCAGGGCGGGGGCGACCTCGGCTCACAGCGCGCCCGGCTATTCTCGCAGCTTTTGCTAATCATG
TTCATACCTCTTATCTTCCTCCCACAGCTCCTGGGCAACGTGCTGGTCTGTGTGCTGGCCCATCACTTTGG
CAAAGAATTCatgttttccatgaggatcgtctgcctggtcctaagtgtggtgggcacagcatggactgacG
CGCCCGGGCCGGCCAGGCGCGCGCCGTACGTACGAAGCTTGGTACCGAGCTCGGATCCACTCCAGTGTG
GTGGAATTCTGCAGATATCCAGCACAGTGGCGGCCGCTCGAGGAGGGCCCGAACAAAAACTCATCTCAGAA
GAGGATCTGA HumanZyme vector-2 (underline = hCMV IE Enhancer; bold = human beta-
actin promoter; italics = human immunoglobulin superfamily member 8
precursor signal peptide)
SEQ ID NO: 33
GTTGACATTGATTATTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAACGACCCCCGCCCATTGAC
GTCAATAATGACGTATGTTCCCATAGTAACGCCAATAGGGACTTTCCATTGACGTCAATGGGTGGACTATT
TACGGTAACGCCAATAGGGACTTTCCATTGACGTCAATGGGTGGACTATTTACGGTAAACTGCCCACTTGG
CAGTACATCAAGTGTATCATATGCCAAGTACGCCCCCTATTGACGTCAATGACGGTAAATGGCCCGCCTGG
CATTATGCCCAGTACATGACCTTATGGGACTTTCCTACTTGGCAGTACATCTACGTATTAGTCATCGCTAT
TACCATGG**CCGGGCCCAGCACCCCAAGGCGGCCAACGCCAAAACTCTCCCTCCTCCTCTTCCTCAATCTCG
CTCTCGCTCTTTTTTTTTTTCGCAAAAGGAGGGGAGAGGGGGTAAAAAAATGCTGCACTGTGCGGCGAAGC**
```

-continued

```
CGGTGAGTGAGCGGCGCGGGGCCAATCAGCGTGCGCCGTTCCGAAAGTTGCCTTTTATGGCTCGAGCGGCC
GCGGCGGCGCCCTATAAAACCCAGCGGCGCGACGCGCCACCACCGCCGAGACCGCGTCCGCCCCGCGAGCA
CAGAGCCTCGCCTTTGCCGATCCGCCGCCCGTCCACACCCGCCGCCAGGTAAGCCCGGCCAGCCGACCGGG
GCAGGCGGCTCACGGCCCGGCCGCAGGCGGCCGCGGCCCCTTCGCCCGTGCAGAGCCGCCGTCTGGGCCGC
AGCGGGGGCGCATGGGGGGGAACCGGACCGCCGTGGGGGCGCGGGAGAAGCCCCTGGGCCTCCGGAGA
TGGGGGACACCCCACGCCAGTTCGGAGGCGCGAGGCCGCGCTCGGGAGGCGCGCTCCGGGGGTGCCGCTCT
CGGGGCGGGGCAACCGGCGGGGTCTTTGTCTGAGCCGGGCTCTTGCCAATGGGGATCGCAGGGTGGGCGC
GGCGGAGCCCCGCCAGGCCCGGTGGGGGCTGGGGCGCCATTGCGCGTGCGCGCTGGTCCTTTGGGCGCTA
ACTGCGTGCGCGCTGGGAATTGGCGCTAATTGCGCGTGCGCGCTGGGACTCAAGGCGCTAACTGCGCGTGC
GTTCTGGGGCCCGGGGTGCCGCGGCCTGGGCTGGGGCGAAGGCGGGCTCGGCCGGAAGGGGTGGGGTCGCC
GCGGCTCCCGGGCGCTTGCGCGCACTTCCTGCCCGAGCCGCTGGCCGCCCGAGGGTGTGGCCGCTGCGTGC
GCGCGCGCCGACCCGGCGCTGTTTGAACCGGGCGGAGGCGGGGCTGGCGCCCGGTTGGGAGGGGGTTGGGG
CCTGGCTTCCTGCCGCGCGCCGCGGGGACGCCTCCGACCAGTGTTTGCCTTTTATGGTAATAACGCGGCCG
GCCCGGCTTCCTTTGTCCCCAATCTGGGCGCGCGCCGGCGCCCCTGGCGGCCTAAGGACTCGGCGCGCCG
GAAGTGGCCAGGGCGGGGCGACCTCGGCTCACAGCGCGCCGGCTATTCTCGCAGCTTTTGCTAATCATG
TTCATACCTCTTATCTTCCTCCCACAGCTCCTGGGCAACGTGCTGGTCTGTGTGCTGGCCCATCACTTTGG
CAAAGAATTCatgggcgccctcaggcccacgctgctgccgccttcgctgccgctgctgctgctaatg
ctaggaatgggatgctgggccgacGCGCCCGGGCCGGCCAGGCGCGCGCGCCGTACGTACGAAGCTTGGTA
CCGAGCTCGGATCCACTCCAGTGTGGTGGAATTCTGCAGATATCCAGCACAGTGGCGGCCGCTCGAGGAGG
GCCCGAACAAAAACTCATCTCAGAAGAGGATCTGA
```

What is claimed is:

1. An expression vector, comprising a cassette which comprises the following operably linked expression elements:

(A) a human cytomegalovirus immediate early enhancer element;

(B) a functional human beta-actin promoter;

(C) a human globin gene intron; and (D) a human signal peptide consisting of a immunoglobulin superfamily 8 signal peptide, or an alpha-fibrinogen signal peptide.

2. The expression vector of claim 1, further comprising a polynucleotide positioned downstream of the signal peptide and operably linked to elements (A), (B), (C), and (D) of claim 1.

3. The expression vector of claim 2, wherein either (i) the polynucleotide is operably linked to a transcription termination signal that is located in the expression vector downstream of the human signal peptide, or (ii) the polynucleotide itself comprises a transcription termination signal.

4. The expression vector of claim 2, wherein the polynucleotide is operably linked to a CMV immediate early enhancer, a beta-actin promoter, a human globin gene intron, and an immunoglobulin superfamily 8 signal peptide.

5. The expression vector of claim 2, wherein the polynucleotide is operably linked to a CMV immediate early enhancer, a beta-actin promoter, a human globin gene intron, and an alpha-fibrinogen signal peptide.

6. The expression vector of claim 2, wherein the polynucleotide encodes a cytokine.

7. The expression vector of claim 6, wherein the encoded cytokine is selected from the group consisting of Activin A, Activin B, Activin A/2xINHbA, Activin B/2xINHbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2B, IFN-γ, β$_1$IFN-β$_1$, IGF I, IGF II, IGF IIv1, IGF IIv2, IL10, IL11, IL12, IL15, IL17/IL17A, IL17F, βIL1 β IL2, IL23, IL27, IL28A/IFN-lambda-2, IL28B/IFN-lambda-3, IL29/IFN-lambda-1, IL1β, IL2 IL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFα, PDGFβ, Persephin, SCF, SDF1α, SHH, Somatotropin, TGF β1, TGF β2, TGF 3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14.

8. The expression vector of claim 7, wherein the encoded cytokine is selected from the group consisting of EPO, G-CSF, GM-CSF, IL-2, IL-4, IL-6, M-CSF, Noggin, SCF, Somatotropin, TGFβ1, TNFα, and VEGF-165.

9. A recombinant method for producing an authentic human protein, comprising introducing the expression vector of claim 1 into a human cell, wherein the polynucleotide encodes a human protein and wherein expression of the polynucleotide in the human cell produces an authentic human protein.

10. The recombinant method of claim 9, wherein the authentic human protein has a similar size, structure, molecular weight, glycosylation pattern, and post-transcriptional modifications to that of a native version of the same human protein.

11. The recombinant method of claim 9, wherein the polynucleotide encodes a protein selected from the group consisting of a cytokine, albumin, IgG, IgA, IgM, IgD, IgE, alpha-1-proteinase inhibitors, blood pro-coagulation proteins, blood anti-coagulation proteins, thrombolytic agents, anti-angiogenic proteins, alpha.-2-antiplasmins, C-1 esterase inhibitors, apolipoproteins, HDL, LDL, Fibronectin, beta-2-glycoprotein I, plasminogens, plasmin, plasminogen activators, plasminogen inhibitors, plasma protease inhibitors, antithrombin III, streptokinases, inter-alpha-trypsin inhibitors, alpha.-2-macroglobulin, amyloid protein, ferritins, pre-albumin, GC-globulin, haemopexin, C3-complement, transferrin, urokinase, and alpha.-1-acid-glycoprotein.

12. The recombinant method of claim 9, wherein the desired polynucleotide encodes a cytokine.

13. The recombinant method of claim 12, wherein the encoded cytokine is selected from the group consisting of Activin A, Activin B, Activin AI2xINHbA, Activin B/2xINHbB, AMH/MIS, Artemin, BDNF, BMP2, BMP15/GDF9B, BMP2/BMP2A, BMP3/Osteogenin, BMP4, BMP4/BMP2B, BMP5, BMP7/OP-1, BMP1, BMP10, BMP15/GDF9B, β-NGF, Cystatin C, Delta 1, EGF, Erythropoietin (EPO), FGF acidic, FGF basic, FGF10, FGF5, FGF7, FGF8b, FLT3 ligand, G-CSF, GDF15, GDF2/BMP9, GDF3, GDF5/BMP14, GDF8/myostatin, GDF9, GDNF, GM-CSF, HGF, HGH, IFN-α2A, IFN-α2β, IFN-γ, β$_1$, IFN β$_1$, IGF I, IGF II, IGF IIv1, IGF IIv2, IL10, IL11, IL12, IL15, IL17/IL17A, IL17F, βIL1 β IL2, IL23, IL27, IL28A/IFN-lambda-2, IL28B/IFN-lambda-3, IL29/IFN-lambda-1, IL1β, IL2 IL3, IL32, IL35, IL4, IL5, IL6, IL7, IL8, IL9, Inhibin A/INHa&INHbA, Inhibin B/INHa&INHbB, Inhibin C/INHa&INHbC, Inhibin E/INHa&INHbE, LEFTYB, LEFTY1/LeftyB, M-CSF, mouse CSF, mouse SCF, NODAL, Noggin, NT3 (neurotrophin3), Oncostatin M, PDGFα, PDGFβ, Persephin, SCF, SDF1α, SHH, Somatotropin, TGF β1, TGF β2, TGF β3, TGFβ4/LEFTY2/LeftyA, TNF α, TPOα, VEGF121aa, VEGF165aa, WIF1, WNT1, Wnt10A, Wnt10B/12, Wnt11, Wnt16, Wnt2, Wnt2B/13, Wnt3, Wnt3A, Wnt4, Wnt5A, Wnt5B, Wnt6, Wnt7A, Wnt7B, Wnt8B, and Wnt9A/14.

14. The recombinant method of claim 13, wherein the encoded cytokine is selected from the group consisting of EPO, G-CSF, GM-CSF, IL-2, IL-4, IL-6, M-CSF, Noggin, SCF, Somatotropin, TGFβ1, TNFα, and VEGF-165.

15. The recombinant method of claim 9, wherein the human cell is HZ-293TS deposited under and bearing the ATCC biological deposit accession number of PTA-10165.

16. A stable human cell line called HZ-293TS deposited under and bearing the ATCC biological deposit accession number of PTA-10165.

17. A human cell that expresses the expression vector of claim 1.

18. The stable human cell of claim 16, further comprising the vector of claim 1.

* * * * *

UNITED STATES PATENT AND TRADEMARK OFFICE
CERTIFICATE OF CORRECTION

| | | |
|---|---|---|
| PATENT NO. | : 8,236,527 B2 | Page 1 of 1 |
| APPLICATION NO. | : 12/922293 | |
| DATED | : August 7, 2012 | |
| INVENTOR(S) | : Ridong Chen, Soon Seog Jeong and Hui Feng | |

It is certified that error appears in the above-identified patent and that said Letters Patent is hereby corrected as shown below:

IN THE CLAIMS

Col. 111, Line 17, Claim 7:

Change "$\beta_1$,IFN-$\beta_1$," to --IFN-$\beta_1$,--.

Col. 111, Line 19, Claim 7:

Change "$\beta$IL1 $\beta$ IL2" to --IL1 $\beta$, IL2--.

Col. 111, Line 27, Claim 7:

Change "TGF 3" to --TGF $\beta$3--.

Col. 112, Line 10, Claim 12:

Delete the word "desired" between the words "the" and "polynucleotide".

Col. 112, Line 13, Claim 13:

Change "AI2xINHbA" to --A/2xINHbA--.

Col. 112, Line 21, Claim 13:

Delete "$\beta_1$,".

Col. 112, Line 23, Claim 13:

Change "$\beta$IL1 $\beta$ IL2" to --IL1 $\beta$, IL2,--.

Signed and Sealed this
Twenty-second Day of January, 2013

David J. Kappos
*Director of the United States Patent and Trademark Office*

SEQUENCE LISTING

<160> NUMBER OF SEQ ID NOS: 40

<210> SEQ ID NO 1
<211> LENGTH: 501
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: CDS
<222> LOCATION: (1)..(495)

<400> SEQUENCE: 1

```
gca ccc atg gca gaa gga gga ggg cag aat cat cac gaa gtg gtg aag      48
Ala Pro Met Ala Glu Gly Gly Gly Gln Asn His His Glu Val Val Lys
1               5                   10                  15 ttc atg gat gtc tat cag cgc agc tac tgc cat cca atc gag acc ctg      96
Phe Met Asp Val Tyr Gln Arg Ser Tyr Cys His Pro Ile Glu Thr Leu
            20                  25                  30 gtg gac atc ttc cag gag tac cct gat gag atc gag tac atc ttc aag     144
Val Asp Ile Phe Gln Glu Tyr Pro Asp Glu Ile Glu Tyr Ile Phe Lys
        35                  40                  45 cca tcc tgt gtg ccc ctg atg cga tgc ggg ggc tgc tgc aat gac gag     192
Pro Ser Cys Val Pro Leu Met Arg Cys Gly Gly Cys Cys Asn Asp Glu
    50                  55                  60 ggc ctg gag tgt gtg ccc act gag gag tcc aac atc acc atg cag att     240
Gly Leu Glu Cys Val Pro Thr Glu Glu Ser Asn Ile Thr Met Gln Ile
65                  70                  75                  80 atg cgg atc aaa cct cac caa ggc cag cac ata gga gag atg agc ttc     288
Met Arg Ile Lys Pro His Gln Gly Gln His Ile Gly Glu Met Ser Phe
                85                  90                  95 cta cag cac aac aaa tgt gaa tgc aga cca aag aaa gat aga gca aga     336
Leu Gln His Asn Lys Cys Glu Cys Arg Pro Lys Lys Asp Arg Ala Arg
            100                 105                 110 caa gaa aat ccc tgt ggg cct tgc tca gag cgg aga aag cat ttg ttt     384
Gln Glu Asn Pro Cys Gly Pro Cys Ser Glu Arg Arg Lys His Leu Phe
        115                 120                 125 gta caa gat ccg cag acg tgt aaa tgt tcc tgc aaa aac aca gac tcg     432
Val Gln Asp Pro Gln Thr Cys Lys Cys Ser Cys Lys Asn Thr Asp Ser
    130                 135                 140 cgt tgc aag gcg agg cag ctt gag tta aac gaa cgt act tgc aga tgt     480
```

```
Arg Cys Lys Ala Arg Gln Leu Glu Leu Asn Glu Arg Thr Cys Arg Cys
145                 150                 155                 160 gac aag ccg agg cgg tgataa                                           501
Asp Lys Pro Arg Arg
                165

<210> SEQ ID NO 2
<211> LENGTH: 165
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
                100                 105                 110

Gln Glu Asn Pro Cys Gly Pro Cys Ser Glu Arg Arg Lys His Leu Phe
            115                 120                 125

Val Gln Asp Pro Gln Thr Cys Lys Cys Ser Cys Lys Asn Thr Asp Ser
        130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 3
<211> LENGTH: 528
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(522)

<400> SEQUENCE: 3 acc ccc ctg ggc cct gcc agc tcc ctg ccc cag agc ttc ctg ctc aag    48
Thr Pro Leu Gly Pro Ala Ser Ser Leu Pro Gln Ser Phe Leu Leu Lys
1               5                   10                  15 tgc tta gag caa gtg agg aag atc cag ggc gat ggc gca gcg ctc cag    96
Cys Leu Glu Gln Val Arg Lys Ile Gln Gly Asp Gly Ala Ala Leu Gln
                20                  25                  30 gag aag ctg tgt gcc acc tac aag ctg tgc cac ccc gag gag ctg gtg   144
Glu Lys Leu Cys Ala Thr Tyr Lys Leu Cys His Pro Glu Glu Leu Val
            35                  40                  45 ctg ctc gga cac tct ctg ggc atc ccc tgg gct ccc ctg agc agc tgc   192
```

```
Leu Leu Gly His Ser Leu Gly Ile Pro Trp Ala Pro Leu Ser Ser Cys
     50                  55                  60 ccc agc cag gcc ctg cag ctg gca ggc tgc ttg agc caa ctc cat agc        240
Pro Ser Gln Ala Leu Gln Leu Ala Gly Cys Leu Ser Gln Leu His Ser
 65                  70                  75                  80 ggc ctt ttc ctc tac cag ggg ctc ctg cag gcc ctg gaa ggg atc tcc        288
Gly Leu Phe Leu Tyr Gln Gly Leu Leu Gln Ala Leu Glu Gly Ile Ser
                 85                  90                  95 ccc gag ttg ggt ccc acc ttg gac aca ctg cag ctg gac gtc gcc gac        336
Pro Glu Leu Gly Pro Thr Leu Asp Thr Leu Gln Leu Asp Val Ala Asp
            100                 105                 110 ttt gcc acc acc atc tgg cag cag atg gaa gaa ctg gga atg gcc cct        384
Phe Ala Thr Thr Ile Trp Gln Gln Met Glu Glu Leu Gly Met Ala Pro
        115                 120                 125 gcc ctg cag ccc acc cag ggt gcc atg ccg gcc ttc gcc tct gct ttc        432
Ala Leu Gln Pro Thr Gln Gly Ala Met Pro Ala Phe Ala Ser Ala Phe
    130                 135                 140 cag cgc cgg gca gga ggg gtc ctg gtt gcc tcc cat ctg cag agc ttc        480
Gln Arg Arg Ala Gly Gly Val Leu Val Ala Ser His Leu Gln Ser Phe
145                 150                 155                 160 ctg gag gtg tcg tac cgc gtt cta cgc cac ctt gcc cag ccc tgataa        528
Leu Glu Val Ser Tyr Arg Val Leu Arg His Leu Ala Gln Pro
                165                 170

<210> SEQ ID NO 4
<211> LENGTH: 174
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Thr Pro Leu Gly Pro Ala Ser Ser Leu Pro Gln Ser Phe Leu Leu Lys
 1               5                  10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
     50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 5
<211> LENGTH: 480
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: CDS
<222> LOCATION: (1)..(474)

<400> SEQUENCE: 5

```
gag gag gtg tcg gag tac tgt agc cac atg att ggg agt gga cac ctg      48
Glu Glu Val Ser Glu Tyr Cys Ser His Met Ile Gly Ser Gly His Leu
1               5                   10                  15 cag tct ctg cag cgg ctg att gac agt cag atg gag acc tcg tgc caa      96
Gln Ser Leu Gln Arg Leu Ile Asp Ser Gln Met Glu Thr Ser Cys Gln
            20                  25                  30 att aca ttt gag ttt gta gac cag gaa cag ttg aaa gat cca gtg tgc     144
Ile Thr Phe Glu Phe Val Asp Gln Glu Gln Leu Lys Asp Pro Val Cys
        35                  40                  45 tac ctt aag aag gca ttt ctc ctg gta caa gac ata atg gag gac acc     192
Tyr Leu Lys Lys Ala Phe Leu Leu Val Gln Asp Ile Met Glu Asp Thr
    50                  55                  60 atg cgc ttc aga gat aac acc ccc aat gcc atc gcc att gtg cag ctg     240
Met Arg Phe Arg Asp Asn Thr Pro Asn Ala Ile Ala Ile Val Gln Leu
65                  70                  75                  80 cag gaa ctc tct ttg agg ctg aag agc tgc ttc acc aag gat tat gaa     288
Gln Glu Leu Ser Leu Arg Leu Lys Ser Cys Phe Thr Lys Asp Tyr Glu
                85                  90                  95 gag cat gac aag gcc tgc gtc cga act ttc tat gag aca cct ctc cag     336
Glu His Asp Lys Ala Cys Val Arg Thr Phe Tyr Glu Thr Pro Leu Gln
            100                 105                 110 ttg ctg gag aag gtc aag aat gtc ttt aat gaa aca aag aat ctc ctt     384
Leu Leu Glu Lys Val Lys Asn Val Phe Asn Glu Thr Lys Asn Leu Leu
        115                 120                 125 gac aag gac tgg aat att ttc agc aag aac tgc aac aac agc ttt gct     432
Asp Lys Asp Trp Asn Ile Phe Ser Lys Asn Cys Asn Asn Ser Phe Ala
    130                 135                 140 gaa tgc tcc agc caa ggc cat gag agg cag tcc gag gga tcc tgataa     480
Glu Cys Ser Ser Gln Gly His Glu Arg Gln Ser Glu Gly Ser
145                 150                 155
```

<210> SEQ ID NO 6
<211> LENGTH: 158
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95
```

```
Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Gly His Glu Arg Gln Ser Glu Gly Ser
145                 150                 155

<210> SEQ ID NO 7
<211> LENGTH: 405
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(399)

<400> SEQUENCE: 7 gca cct act tca agt tct aca aag aaa aca cag cta caa ctg gag cat    48
Ala Pro Thr Ser Ser Ser Thr Lys Lys Thr Gln Leu Gln Leu Glu His
1               5                   10                  15 tta ctg ctg gat tta cag atg att ttg aat gga att aat aat tac aag    96
Leu Leu Leu Asp Leu Gln Met Ile Leu Asn Gly Ile Asn Asn Tyr Lys
            20                  25                  30 aat ccc aaa ctc acc agg atg ctc aca ttt aag ttt tac atg ccc aag   144
Asn Pro Lys Leu Thr Arg Met Leu Thr Phe Lys Phe Tyr Met Pro Lys
        35                  40                  45 aag gcc aca gaa ctg aaa cat ctt cag tgt cta gaa gaa gaa ctc aaa   192
Lys Ala Thr Glu Leu Lys His Leu Gln Cys Leu Glu Glu Glu Leu Lys
    50                  55                  60 cct ctg gag gaa gtg cta aat tta gct caa agc aaa aac ttt cac tta   240
Pro Leu Glu Glu Val Leu Asn Leu Ala Gln Ser Lys Asn Phe His Leu
65                  70                  75                  80 aga ccc agg gac tta atc agc aat atc aac gta ata gtt ctg gaa cta   288
Arg Pro Arg Asp Leu Ile Ser Asn Ile Asn Val Ile Val Leu Glu Leu
                85                  90                  95 aag gga tct gaa aca aca ttc atg tgt gaa tat gct gat gag aca gca   336
Lys Gly Ser Glu Thr Thr Phe Met Cys Glu Tyr Ala Asp Glu Thr Ala
            100                 105                 110 acc att gta gaa ttt ctg aac aga tgg att acc ttt tgt caa agc atc   384
Thr Ile Val Glu Phe Leu Asn Arg Trp Ile Thr Phe Cys Gln Ser Ile
        115                 120                 125 atc tca aca ctg act tgataa                                        405
Ile Ser Thr Leu Thr
    130

<210> SEQ ID NO 8
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
```

-continued

```
                  20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 9
<211> LENGTH: 579
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: CDS
<222> LOCATION: (1)..(573)

<400> SEQUENCE: 9

```
ttc cca acc att ccc tta tcc agg ctt ttt gac aac gct atg ctc cgc      48
Phe Pro Thr Ile Pro Leu Ser Arg Leu Phe Asp Asn Ala Met Leu Arg
1               5                   10                  15 gcc cat cgt ctg cac cag ctg gcc ttt gac acc tac cag gag ttt gaa      96
Ala His Arg Leu His Gln Leu Ala Phe Asp Thr Tyr Gln Glu Phe Glu
            20                  25                  30 gaa gcc tat atc cca aag gaa cag aag tat tca ttc ctg cag aac ccc     144
Glu Ala Tyr Ile Pro Lys Glu Gln Lys Tyr Ser Phe Leu Gln Asn Pro
        35                  40                  45 cag acc tcc ctc tgt ttc tca gag tct att ccg aca ccc tcc aac agg     192
Gln Thr Ser Leu Cys Phe Ser Glu Ser Ile Pro Thr Pro Ser Asn Arg
    50                  55                  60 gag gaa aca caa cag aaa tcc aac cta gag ctg ctc cgc atc tcc ctg     240
Glu Glu Thr Gln Gln Lys Ser Asn Leu Glu Leu Leu Arg Ile Ser Leu
65                  70                  75                  80 ctg ctc atc cag tcg tgg ctg gag ccc gtg cag ttc ctc agg agt gtc     288
Leu Leu Ile Gln Ser Trp Leu Glu Pro Val Gln Phe Leu Arg Ser Val
                85                  90                  95 ttc gcc aac agc ctg gtg tac ggc gcc tct gac agc aac gtc tat gac     336
Phe Ala Asn Ser Leu Val Tyr Gly Ala Ser Asp Ser Asn Val Tyr Asp
            100                 105                 110 ctc cta aag gac cta gag gaa ggc atc caa acg ctg atg ggg agg ctg     384
Leu Leu Lys Asp Leu Glu Glu Gly Ile Gln Thr Leu Met Gly Arg Leu
        115                 120                 125 gaa gat ggc agc ccc cgg act ggg cag atc ttc aag cag acc tac agc     432
Glu Asp Gly Ser Pro Arg Thr Gly Gln Ile Phe Lys Gln Thr Tyr Ser
    130                 135                 140 aag ttc gac aca aac tca cac aac gat gac gca cta ctc aag aac tac     480
Lys Phe Asp Thr Asn Ser His Asn Asp Asp Ala Leu Leu Lys Asn Tyr
145                 150                 155                 160 ggg ctg ctc tac tgc ttc agg aag gac atg gac aag gtc gag aca ttc     528
Gly Leu Leu Tyr Cys Phe Arg Lys Asp Met Asp Lys Val Glu Thr Phe
```

```
                    165                 170                 175
ctg cgc atc gtg cag tgc cgc tct gtg gag ggc agc tgt ggc ttc          573
Leu Arg Ile Val Gln Cys Arg Ser Val Glu Gly Ser Cys Gly Phe
        180                 185                 190 tagtaa                                                                579
```

<210> SEQ ID NO 10
<211> LENGTH: 191
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 11
<211> LENGTH: 1089
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(1083)

<400> SEQUENCE: 11

```
cta tcc acc tgc aag act atc gac atg gag ctg gtg aag cgg aag cgc          48
Leu Ser Thr Cys Lys Thr Ile Asp Met Glu Leu Val Lys Arg Lys Arg
1               5                   10                  15 atc gag gcc atc cgc ggc cag atc ctg tcc aag ctg cgg ctc gcc agc          96
Ile Glu Ala Ile Arg Gly Gln Ile Leu Ser Lys Leu Arg Leu Ala Ser
            20                  25                  30 ccc ccg agc cag ggg gag gtg ccg ccc ggc ccg ctg ccc gag gcc gtg         144
```

```
                Pro Pro Ser Gln Gly Glu Val Pro Gly Pro Leu Pro Glu Ala Val
                        35                  40                  45 ctc gcc ctg tac aac agc acc cgc gac cgg gtg gcc ggg gag agt gca          192
Leu Ala Leu Tyr Asn Ser Thr Arg Asp Arg Val Ala Gly Glu Ser Ala
50                  55                  60 gaa ccg gag ccc gag cct gag gcc gac tac tac gcc aag gag gtc acc          240
Glu Pro Glu Pro Glu Pro Glu Ala Asp Tyr Tyr Ala Lys Glu Val Thr
65                  70                  75                  80 cgc gtg cta atg gtg gaa acc cac aac gaa atc tat gac aag ttc aag          288
Arg Val Leu Met Val Glu Thr His Asn Glu Ile Tyr Asp Lys Phe Lys
                85                  90                  95 cag agt aca cac agc ata tat atg ttc ttc aac aca tca gag ctc cga          336
Gln Ser Thr His Ser Ile Tyr Met Phe Phe Asn Thr Ser Glu Leu Arg
                100                 105                 110 gaa gcg gta cct gaa ccc gtg ttg ctc tcc cgg gca gag ctg cgt ctg          384
Glu Ala Val Pro Glu Pro Val Leu Leu Ser Arg Ala Glu Leu Arg Leu
                115                 120                 125 ctg agg ctc aag tta aaa gtg gag cag cac gtg gag ctg tac cag aaa          432
Leu Arg Leu Lys Leu Lys Val Glu Gln His Val Glu Leu Tyr Gln Lys
130                 135                 140 tac agc aac aat tcc tgg cga tac ctc agc aac cgg ctg ctg gca ccc          480
Tyr Ser Asn Asn Ser Trp Arg Tyr Leu Ser Asn Arg Leu Leu Ala Pro
145                 150                 155                 160 agc gac tcg cca gag tgg tta tct ttt gat gtc acc gga gtt gtg cgg          528
Ser Asp Ser Pro Glu Trp Leu Ser Phe Asp Val Thr Gly Val Val Arg
                165                 170                 175 cag tgg ttg agc cgt gga ggg gaa att gag ggc ttt cgc ctt agc gcc          576
Gln Trp Leu Ser Arg Gly Gly Glu Ile Glu Gly Phe Arg Leu Ser Ala
                180                 185                 190 cac tgc tcc tgt gac agc agg gat aac aca ctg caa gtg gac atc aac          624
His Cys Ser Cys Asp Ser Arg Asp Asn Thr Leu Gln Val Asp Ile Asn
                195                 200                 205 ggg ttc act acc ggc cgc cga ggt gac ctg gcc acc att cat ggc atg          672
Gly Phe Thr Thr Gly Arg Arg Gly Asp Leu Ala Thr Ile His Gly Met
210                 215                 220 aac cgg cct ttc ctg ctt ctc atg gcc acc ccg ctg gag agg gcc cag          720
Asn Arg Pro Phe Leu Leu Leu Met Ala Thr Pro Leu Glu Arg Ala Gln
225                 230                 235                 240 cat ctg caa agc tcc cgg cac cgc cga gcc ctg gac acc aac tat tgc          768
His Leu Gln Ser Ser Arg His Arg Arg Ala Leu Asp Thr Asn Tyr Cys
                245                 250                 255 ttc agc tcc acg gag aag aac tgc tgc gtg cgg cag ctg tac att gac          816
Phe Ser Ser Thr Glu Lys Asn Cys Cys Val Arg Gln Leu Tyr Ile Asp
                260                 265                 270 ttc cgc aag gac ctc ggc tgg aag tgg atc cac gag ccc aag ggc tac          864
Phe Arg Lys Asp Leu Gly Trp Lys Trp Ile His Glu Pro Lys Gly Tyr
                275                 280                 285 cat gcc aac ttc tgc ctc ggg ccc tgc ccc tac att tgg agc ctg gac          912
His Ala Asn Phe Cys Leu Gly Pro Cys Pro Tyr Ile Trp Ser Leu Asp
290                 295                 300 acg cag tac agc aag gtc ctg gcc ctg tac aac cag cat aac ccg ggc          960
Thr Gln Tyr Ser Lys Val Leu Ala Leu Tyr Asn Gln His Asn Pro Gly
305                 310                 315                 320 gcc tcg gcg gcg ccg tgc tgc gtg ccg cag gcg ctg gag ccg ctg ccc         1008
Ala Ser Ala Ala Pro Cys Cys Val Pro Gln Ala Leu Glu Pro Leu Pro
                325                 330                 335 atc gtg tac tac gtg ggc cgc aag ccc aag gtg gag cag ctg tcc aac         1056
Ile Val Tyr Tyr Val Gly Arg Lys Pro Lys Val Glu Gln Leu Ser Asn
                340                 345                 350 atg atc gtg cgc tcc tgc aag tgc agc tgataa                              1089
```

```
Met Ile Val Arg Ser Cys Lys Cys Ser
            355                 360
```

<210> SEQ ID NO 12
<211> LENGTH: 361
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350
```

```
Met Ile Val Arg Ser Cys Lys Cys Ser
        355                 360

<210> SEQ ID NO 13
<211> LENGTH: 477
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(471)

<400> SEQUENCE: 13 gtc aga tca tct tct cga acc ccg agt gac aag cct gta gcc cat gtt      48
Val Arg Ser Ser Ser Arg Thr Pro Ser Asp Lys Pro Val Ala His Val
1               5                   10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
                20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
            35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
        50                  55                  60 aag ggc caa ggc tgc ccc tcc acc cat gtg ctc ctc acc cac acc atc     240
Lys Gly Gln Gly Cys Pro Ser Thr His Val Leu Leu Thr His Thr Ile
65                  70                  75                  80 agc cgc atc gcc gtc tcc tac cag acc aag gtc aac ctc ctc tct gcc     288
Ser Arg Ile Ala Val Ser Tyr Gln Thr Lys Val Asn Leu Leu Ser Ala
                85                  90                  95 atc aag agc ccc tgc cag agg gag acc cca gag ggg gct gag gcc aag     336
Ile Lys Ser Pro Cys Gln Arg Glu Thr Pro Glu Gly Ala Glu Ala Lys
            100                 105                 110 ccc tgg tat gag ccc atc tat ctg gga ggg gtc ttc cag ctg gag aag     384
Pro Trp Tyr Glu Pro Ile Tyr Leu Gly Gly Val Phe Gln Leu Glu Lys
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg tgataa          477
Ala Glu Ser Gly Gln Val Tyr Phe Gly Ile Ile Ala Leu
145                 150                 155

<210> SEQ ID NO 14
<211> LENGTH: 157
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45
```

```
Val Val Pro Ser Glu Gly Leu Tyr Leu Ile Tyr Ser Gln Val Leu Phe
 50                  55                  60

Lys Gly Gln Gly Cys Pro Ser Thr His Val Leu Thr His Thr Ile
 65                  70                  75                  80

Ser Arg Ile Ala Val Ser Tyr Gln Thr Lys Val Asn Leu Leu Ser Ala
                 85                  90                  95

Ile Lys Ser Pro Cys Gln Arg Glu Thr Pro Glu Gly Ala Glu Ala Lys
                100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155

<210> SEQ ID NO 15
<211> LENGTH: 561
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(555)

<400> SEQUENCE: 15 gcc cca gta ccc cca gga gaa gat tcc aaa gat gta gcc gcc cca cac      48
Ala Pro Val Pro Pro Gly Glu Asp Ser Lys Asp Val Ala Ala Pro His
  1               5                  10                  15 aga cag cca ctc acc tct tca gaa cga att gac aaa caa att cgg tac      96
Arg Gln Pro Leu Thr Ser Ser Glu Arg Ile Asp Lys Gln Ile Arg Tyr
             20                  25                  30 atc ctc gac ggc atc tca gcc ctg aga aag gag aca tgt aac aag agt     144
Ile Leu Asp Gly Ile Ser Ala Leu Arg Lys Glu Thr Cys Asn Lys Ser
         35                  40                  45 aac atg tgt gaa agc agc aaa gag gca ctg gca gaa aac aac ctg aac     192
Asn Met Cys Glu Ser Ser Lys Glu Ala Leu Ala Glu Asn Asn Leu Asn
 50                  55                  60 ctt cca aag atg gct gaa aaa gat gga tgc ttc caa tct gga ttc aat     240
Leu Pro Lys Met Ala Glu Lys Asp Gly Cys Phe Gln Ser Gly Phe Asn
 65                  70                  75                  80 gag gag act tgc ctg gtg aaa atc atc act ggt ctt ttg gag ttt gag     288
Glu Glu Thr Cys Leu Val Lys Ile Ile Thr Gly Leu Leu Glu Phe Glu
                 85                  90                  95 gta tac cta gag tac ctc cag aac aga ttt gag agt agt gag gaa caa     336
Val Tyr Leu Glu Tyr Leu Gln Asn Arg Phe Glu Ser Ser Glu Glu Gln
            100                 105                 110 gcc aga gct gtg cag atg agt aca aaa gtc ctg atc cag ttc ctg cag     384
Ala Arg Ala Val Gln Met Ser Thr Lys Val Leu Ile Gln Phe Leu Gln
        115                 120                 125 aaa aag gca aag aat cta gat gca ata acc acc cct gac cca acc aca     432
Lys Lys Ala Lys Asn Leu Asp Ala Ile Thr Thr Pro Asp Pro Thr Thr
    130                 135                 140 aat gcc agc ctg ctg acg aag ctg cag gca cag aac cag tgg ctg cag     480
Asn Ala Ser Leu Leu Thr Lys Leu Gln Ala Gln Asn Gln Trp Leu Gln
145                 150                 155                 160 gac atg aca act cat ctc att ctg cgc agc ttt aag gag ttc ctg cag     528
Asp Met Thr Thr His Leu Ile Leu Arg Ser Phe Lys Glu Phe Leu Gln
                165                 170                 175
```

```
tcc agc ctg agg gct ctt cgg caa atg tagtaa                                    561
Ser Ser Leu Arg Ala Leu Arg Gln Met
        180                 185

<210> SEQ ID NO 16
<211> LENGTH: 185
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ala Pro Val Pro Pro Gly Glu Asp Ser Lys Asp Val Ala Ala Pro His
1               5                   10                  15

Arg Gln Pro Leu Thr Ser Ser Glu Arg Ile Asp Lys Gln Ile Arg Tyr
            20                  25                  30

Ile Leu Asp Gly Ile Ser Ala Leu Arg Lys Glu Thr Cys Asn Lys Ser
        35                  40                  45

Asn Met Cys Glu Ser Ser Lys Glu Ala Leu Ala Glu Asn Asn Leu Asn
    50                  55                  60

Leu Pro Lys Met Ala Glu Lys Asp Gly Cys Phe Gln Ser Gly Phe Asn
65                  70                  75                  80

Glu Glu Thr Cys Leu Val Lys Ile Ile Thr Gly Leu Leu Glu Phe Glu
                85                  90                  95

Val Tyr Leu Glu Tyr Leu Gln Asn Arg Phe Glu Ser Ser Glu Glu Gln
            100                 105                 110

Ala Arg Ala Val Gln Met Ser Thr Lys Val Leu Ile Gln Phe Leu Gln
        115                 120                 125

Lys Lys Ala Lys Asn Leu Asp Ala Ile Thr Thr Pro Asp Pro Thr Thr
    130                 135                 140

Asn Ala Ser Leu Leu Thr Lys Leu Gln Ala Gln Asn Gln Trp Leu Gln
145                 150                 155                 160

Asp Met Thr Thr His Leu Ile Leu Arg Ser Phe Lys Glu Phe Leu Gln
                165                 170                 175

Ser Ser Leu Arg Ala Leu Arg Gln Met
            180                 185

<210> SEQ ID NO 17
<211> LENGTH: 504
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(498)

<400> SEQUENCE: 17 gcc cca cca cgc ctc atc tgt gac agc cga gtc ctg gag agg tac ctc        48
Ala Pro Pro Arg Leu Ile Cys Asp Ser Arg Val Leu Glu Arg Tyr Leu
1               5                   10                  15 ttg gag gcc aag gag gcc gag aat atc acg acg ggc tgt gct gaa cac        96
Leu Glu Ala Lys Glu Ala Glu Asn Ile Thr Thr Gly Cys Ala Glu His
            20                  25                  30 tgc agc ttg aat gag aat atc act gtc cca gac acc aaa gtt aat ttc       144
Cys Ser Leu Asn Glu Asn Ile Thr Val Pro Asp Thr Lys Val Asn Phe
        35                  40                  45 tat gcc tgg aag agg atg gag gtc ggg cag cag gcc gta gaa gtc tgg       192
```

```
                                                         240
cag ggc ctg gcc ctg ctg tcg gaa gct gtc ctg cgg ggc cag gcc ctg
Gln Gly Leu Ala Leu Leu Ser Glu Ala Val Leu Arg Gly Gln Ala Leu
 65          70                  75                  80

288
ttg gtc aac tct tcc cag ccg tgg gag ccc ctg cag ctg cat gtg gat
Leu Val Asn Ser Ser Gln Pro Trp Glu Pro Leu Gln Leu His Val Asp
             85                  90                  95

336
aaa gcc gtc agt ggc ctt cgc agc ctc acc act ctg ctt cgg gct ctg
Lys Ala Val Ser Gly Leu Arg Ser Leu Thr Thr Leu Leu Arg Ala Leu
100                 105                 110

384
gga gcc cag aag gaa gcc atc tcc cct cca gat gcg gcc tca gct gct
Gly Ala Gln Lys Glu Ala Ile Ser Pro Pro Asp Ala Ala Ser Ala Ala
        115                 120                 125

432
cca ctc cga aca atc act gct gac act ttc cgc aaa ctc ttc cga gtc
Pro Leu Arg Thr Ile Thr Ala Asp Thr Phe Arg Lys Leu Phe Arg Val
130                 135                 140

480
tac tcc aat ttc ctc cgg gga aag ctg aag ctg tac aca ggg gag gcc
Tyr Ser Asn Phe Leu Arg Gly Lys Leu Lys Leu Tyr Thr Gly Glu Ala
145                 150                 155                 160

504
tgc agg aca ggg gac aga tgataa
Cys Arg Thr Gly Asp Arg
                165
```

<210> SEQ ID NO 18
<211> LENGTH: 166
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

```
Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 19
<211> LENGTH: 387
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(381)

<400> SEQUENCE: 19 gca ccc gcc cgc tcg ccc agc ccc agc acg cag ccc tgg gag cat gtg      48
Ala Pro Ala Arg Ser Pro Ser Pro Ser Thr Gln Pro Trp Glu His Val
1               5                   10                  15 aat gcc atc cag gag gcc cgg cgt ctc ctg aac ctg agt aga gac act      96
Asn Ala Ile Gln Glu Ala Arg Arg Leu Leu Asn Leu Ser Arg Asp Thr
            20                  25                  30 gct gct gag atg aat gaa aca gta gaa gtc atc tca gaa atg ttt gac     144
Ala Ala Glu Met Asn Glu Thr Val Glu Val Ile Ser Glu Met Phe Asp
        35                  40                  45 ctc cag gag ccg acc tgc cta cag acc cgc ctg gag ctg tac aag cag     192
Leu Gln Glu Pro Thr Cys Leu Gln Thr Arg Leu Glu Leu Tyr Lys Gln
    50                  55                  60 ggc ctg cgg ggc agc ctc acc aag ctc aag ggc ccc ttg acc atg atg     240
Gly Leu Arg Gly Ser Leu Thr Lys Leu Lys Gly Pro Leu Thr Met Met
65                  70                  75                  80 gcc agc cac tac aag cag cac tgc cct cca acc ccg gaa act tcc tgt     288
Ala Ser His Tyr Lys Gln His Cys Pro Pro Thr Pro Glu Thr Ser Cys
                85                  90                  95 gca acc cag att atc acc ttt gaa agt ttc aaa gag aac ctg aag gac     336
Ala Thr Gln Ile Ile Thr Phe Glu Ser Phe Lys Glu Asn Leu Lys Asp
            100                 105                 110 ttt ctg ctt gtc atc ccc ttt gac tgc tgg gag cca gtc cag gag         381
Phe Leu Leu Val Ile Pro Phe Asp Cys Trp Glu Pro Val Gln Glu
        115                 120                 125 tgataa                                                              387

<210> SEQ ID NO 20
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125
```

<210> SEQ ID NO 21
<211> LENGTH: 393
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: CDS
<222> LOCATION: (1)..(387)

<400> SEQUENCE: 21

```
cac aag tgc gat atc acc tta cag gag atc atc aaa act ttg aac agc      48
His Lys Cys Asp Ile Thr Leu Gln Glu Ile Ile Lys Thr Leu Asn Ser
1               5                  10                  15 ctc aca gag cag aag act ctg tgc acc gag ttg acc gta aca gac atc      96
Leu Thr Glu Gln Lys Thr Leu Cys Thr Glu Leu Thr Val Thr Asp Ile
            20                  25                  30 ttt gct gcc tcc aag aac aca act gag aag gaa acc ttc tgc agg gct     144
Phe Ala Ala Ser Lys Asn Thr Thr Glu Lys Glu Thr Phe Cys Arg Ala
        35                  40                  45 gcg act gtg ctc cgg cag ttc tac agc cac cat gag aag gac act cgc     192
Ala Thr Val Leu Arg Gln Phe Tyr Ser His His Glu Lys Asp Thr Arg
    50                  55                  60 tgc ctg ggt gcg act gca cag cag ttc cac agg cac aag cag ctg atc     240
Cys Leu Gly Ala Thr Ala Gln Gln Phe His Arg His Lys Gln Leu Ile
65                  70                  75                  80 cga ttc ctg aaa cgg ctc gac agg aac ctc tgg ggc ctg gcg ggc ttg     288
Arg Phe Leu Lys Arg Leu Asp Arg Asn Leu Trp Gly Leu Ala Gly Leu
                85                  90                  95 aat tcc tgt cct gtg aag gaa gcc aac cag agt acg ttg gaa aac ttc     336
Asn Ser Cys Pro Val Lys Glu Ala Asn Gln Ser Thr Leu Glu Asn Phe
            100                 105                 110 ttg gaa agg cta aag acg atc atg aga gag aaa tat tca aag tgt tcg     384
Leu Glu Arg Leu Lys Thr Ile Met Arg Glu Lys Tyr Ser Lys Cys Ser
        115                 120                 125 agc tgataa                                                          393
Ser
```

<210> SEQ ID NO 22
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
His Lys Cys Asp Ile Thr Leu Gln Glu Ile Ile Lys Thr Leu Asn Ser
1               5                  10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95
```

```
Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 23
<211> LENGTH: 621
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(615)

<400> SEQUENCE: 23 cag cac tat ctc cac atc cgc ccg gca ccc agc gac aac ctg ccc ctg      48
Gln His Tyr Leu His Ile Arg Pro Ala Pro Ser Asp Asn Leu Pro Leu
1               5                   10                  15 gtg gac ctc atc gaa cac cca gac cct atc ttt gac ccc aag gaa aag      96
Val Asp Leu Ile Glu His Pro Asp Pro Ile Phe Asp Pro Lys Glu Lys
            20                  25                  30 gat ctg aac gag acg ctg ctg cgc tcg ctc ctc ggg ggc cac tac gac     144
Asp Leu Asn Glu Thr Leu Leu Arg Ser Leu Leu Gly Gly His Tyr Asp
        35                  40                  45 cca ggc ttc atg gcc acc tcg ccc ccc gag gac cgg ccc ggg ggc          192
Pro Gly Phe Met Ala Thr Ser Pro Pro Glu Asp Arg Pro Gly Gly Gly
    50                  55                  60 ggg ggt gca gct ggg ggc gcg gag gac ctg gcg gag ctg gac cag ctg     240
Gly Gly Ala Ala Gly Gly Ala Glu Asp Leu Ala Glu Leu Asp Gln Leu
65                  70                  75                  80 ctg cgg cag cgg ccg tcg ggg gcc atg ccg agc gag atc aaa ggg cta     288
Leu Arg Gln Arg Pro Ser Gly Ala Met Pro Ser Glu Ile Lys Gly Leu
                85                  90                  95 gag ttc tcc gag ggc ttg gcc cag ggc aag aag cag cgc cta agc aag     336
Glu Phe Ser Glu Gly Leu Ala Gln Gly Lys Lys Gln Arg Leu Ser Lys
            100                 105                 110 aag ctg cgg agg aag tta cag atg tgg ctg tgg tcg cag aca ttc tgc     384
Lys Leu Arg Arg Lys Leu Gln Met Trp Leu Trp Ser Gln Thr Phe Cys
        115                 120                 125 ccc gtg ctg tac gcg tgg aac gac ctg ggc agc cgc ttt tgg ccg cgc     432
Pro Val Leu Tyr Ala Trp Asn Asp Leu Gly Ser Arg Phe Trp Pro Arg
    130                 135                 140 tac gtg aag gtg ggc agc tgc ttc agt aag cgc tcg tgc tcc gtg ccc     480
Tyr Val Lys Val Gly Ser Cys Phe Ser Lys Arg Ser Cys Ser Val Pro
145                 150                 155                 160 gag ggc atg gtg tgc aag ccg tcc aag tcc gtg cac ctc acg gtg ctg     528
Glu Gly Met Val Cys Lys Pro Ser Lys Ser Val His Leu Thr Val Leu
                165                 170                 175 cgg tgg cgc tgt cag cgg cgc ggg ggc cag cgc tgc ggc tgg att ccc     576
Arg Trp Arg Cys Gln Arg Arg Gly Gly Gln Arg Cys Gly Trp Ile Pro
            180                 185                 190 atc cag tac ccc atc att tcc gag tgc aag tgc tcg tgc tagtaa          621
Ile Gln Tyr Pro Ile Ile Ser Glu Cys Lys Cys Ser Cys
        195                 200                 205

<210> SEQ ID NO 24
<211> LENGTH: 205
<212> TYPE: PRT
```

<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 24

```
Gln His Tyr Leu His Ile Arg Pro Ala Pro Ser Asp Asn Leu Pro Leu
1               5                   10                  15

Val Asp Leu Ile Glu His Pro Asp Pro Ile Phe Asp Pro Lys Glu Lys
            20                  25                  30

Asp Leu Asn Glu Thr Leu Leu Arg Ser Leu Leu Gly Gly His Tyr Asp
        35                  40                  45

Pro Gly Phe Met Ala Thr Ser Pro Pro Glu Asp Arg Pro Gly Gly Gly
    50                  55                  60

Gly Gly Ala Ala Gly Gly Ala Glu Asp Leu Ala Glu Leu Asp Gln Leu
65                  70                  75                  80

Leu Arg Gln Arg Pro Ser Gly Ala Met Pro Ser Glu Ile Lys Gly Leu
                85                  90                  95

Glu Phe Ser Glu Gly Leu Ala Gln Gly Lys Lys Gln Arg Leu Ser Lys
            100                 105                 110

Lys Leu Arg Arg Lys Leu Gln Met Trp Leu Trp Ser Gln Thr Phe Cys
        115                 120                 125

Pro Val Leu Tyr Ala Trp Asn Asp Leu Gly Ser Arg Phe Trp Pro Arg
    130                 135                 140

Tyr Val Lys Val Gly Ser Cys Phe Ser Lys Arg Ser Cys Ser Val Pro
145                 150                 155                 160

Glu Gly Met Val Cys Lys Pro Ser Lys Ser Val His Leu Thr Val Leu
                165                 170                 175

Arg Trp Arg Cys Gln Arg Arg Gly Gly Gln Arg Cys Gly Trp Ile Pro
            180                 185                 190

Ile Gln Tyr Pro Ile Ile Ser Glu Cys Lys Cys Ser Cys
        195                 200                 205
```

<210> SEQ ID NO 25
<211> LENGTH: 573
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: CDS
<222> LOCATION: (1)..(567)

<400> SEQUENCE: 25

```
gaa ggg atc tgc agg aat cgt gtg act aat aat gta aaa gac gtc act     48
Glu Gly Ile Cys Arg Asn Arg Val Thr Asn Asn Val Lys Asp Val Thr
1               5                   10                  15 aaa ttg gtg gca aat ctt cca aaa gac tac atg ata acc ctc aaa tat     96
Lys Leu Val Ala Asn Leu Pro Lys Asp Tyr Met Ile Thr Leu Lys Tyr
            20                  25                  30 gtc ccc ggg atg gat gtt ttg cca agt cat tgt tgg ata agc gag atg    144
Val Pro Gly Met Asp Val Leu Pro Ser His Cys Trp Ile Ser Glu Met
        35                  40                  45 gta gta caa ttg tca gac agc ttg act gat ctt ctg gac aag ttt tca    192
Val Val Gln Leu Ser Asp Ser Leu Thr Asp Leu Leu Asp Lys Phe Ser
    50                  55                  60 aat att tct gaa ggc ttg agt aat tat tcc atc ata gac aaa ctt gtg    240
Asn Ile Ser Glu Gly Leu Ser Asn Tyr Ser Ile Ile Asp Lys Leu Val
```

```
                    65                  70                  75                  80
aat ata gtg gat gac ctt gtg gag tgc gtg aaa gaa aac tca tct aag      288
Asn Ile Val Asp Asp Leu Val Glu Cys Val Lys Glu Asn Ser Ser Lys
                85                  90                  95 gat cta aaa aaa tca ttc aag agc cca gaa ccc agg ctc ttt act cct      336
Asp Leu Lys Lys Ser Phe Lys Ser Pro Glu Pro Arg Leu Phe Thr Pro
            100                 105                 110 gaa gaa ttc ttt aga att ttt aat aga tcc att gat gcc ttc aag gac      384
Glu Glu Phe Phe Arg Ile Phe Asn Arg Ser Ile Asp Ala Phe Lys Asp
            115                 120                 125 ttt gta gtg gca tct gaa act agt gat tgt gtg gtt tct tca aca tta      432
Phe Val Val Ala Ser Glu Thr Ser Asp Cys Val Val Ser Ser Thr Leu
        130                 135                 140 agt cct gag aaa gat tcc aga gtc agt gtc aca aaa cca ttt atg tta      480
Ser Pro Glu Lys Asp Ser Arg Val Ser Val Thr Lys Pro Phe Met Leu
145                 150                 155                 160 ccc cct gtt gca gcc agc tcc ctt agg aat gac agc agt agc agt aat      528
Pro Pro Val Ala Ala Ser Ser Leu Arg Asn Asp Ser Ser Ser Ser Asn
                165                 170                 175 agg aag gcc aaa aat ccc cct gga gac tcc agc cta cac tgataa          573
Arg Lys Ala Lys Asn Pro Pro Gly Asp Ser Ser Leu His
                180                 185
```

<210> SEQ ID NO 26
<211> LENGTH: 189
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

```
Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His
                180                 185
```

<210> SEQ ID NO 27

<211> LENGTH: 434
<212> TYPE: DNA
<213> ORGANISM: Homo sapiens

<400> SEQUENCE: 27

```
gttgacattg attattgact agttattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggact atttacggta acgccaatag gactttcca   240
ttgacgtcaa tgggtggact atttacggta aactgcccac ttggcagtac atcaagtgta   300
tcatatgcca agtacgcccc ctattgacgt caatgacggt aaatggcccg cctggcatta   360
tgcccagtac atgaccttat gggactttcc tacttggcag tacatctacg tattagtcat   420
cgctattacc atgg                                                      434
```

<210> SEQ ID NO 28
<211> LENGTH: 1184
<212> TYPE: DNA
<213> ORGANISM: Homo sapiens

<400> SEQUENCE: 28

```
ccgggcccag caccccaagg cggccaacgc caaaactctc cctcctcctc ttcctcaatc    60
tcgctctcgc tcttttttttt tttcgcaaaa ggaggggaga gggggtaaaa aaatgctgca   120
ctgtgcggcg aagccggtga gtgagcggcg cggggccaat cagcgtgcgc cgttccgaaa   180
gttgcctttt atggctcgag cggccgcggc ggcgccctat aaaacccagc ggcgcgacgc   240
gccaccaccg ccgagaccgc gtccgccccg cgagcacaga gcctcgcctt tgccgatccg   300
ccgcccgtcc acacccgccg ccaggtaagc ccggccagcc gaccggggca ggcggctcac   360
ggcccggccg caggcggccg cggccccttc gcccgtgcag agccgccgtc tgggccgcag   420
cggggggcgc atggggggg aaccggaccg ccgtggggg cgcgggagaa gcccctgggc   480
ctccggagat gggggacacc ccacgccagt tcggaggcgc gaggccgcgc tcggaggcg   540
cgctccgggg gtgccgctct cggggcgggg caaccggcg gggtctttgt ctgagccggg   600
ctcttgccaa tggggatcgc agggtgggcg cggcggagcc cccgccaggc ccggtggggg   660
ctggggcgcc attgcgcgtg cgcgctggtc ctttgggcgc taactgcgtg cgcgctggga   720
attggcgcta attgcgcgtg cgcgctggga ctcaaggcgc taactgcgcg tgcgttctgg   780
ggcccggggt gccgcggcct gggctgggc gaaggcgggc tcggccggaa ggggtggggt   840
cgccgcggct cccgggcgct tgcgcgcact tcctgcccga ccgctggcc gcccgagggt   900
gtggccgctg cgtgcgcgcg cgccgacccg gcgctgtttg aaccgggcgg aggcggggct   960
ggcgcccggt tgggaggggg ttggggcctg gcttcctgcc gcgcgccgcg gggacgcctc  1020
cgaccagtgt ttgccttttta tggtaataac gcggccggcc cggcttcctt tgtccccaat  1080
ctgggcgcgc gccggcgccc cctggcggcc taaggactcg gcgcgccgga agtggccagg  1140
gcggggcga cctcggctca cagcgcgccc ggctattctc gcag                    1184
```

<210> SEQ ID NO 29
<211> LENGTH: 96
<212> TYPE: DNA
<213> ORGANISM: Homo sapiens

<400> SEQUENCE: 29

```
cttttgctaa tcatgttcat acctcttatc ttcctcccac agctcctggg caacgtgctg    60
```

```
gtctgtgtgc tggcccatca ctttggcaaa gaattc                              96
```

<210> SEQ ID NO 30
<211> LENGTH: 20
<212> TYPE: PRT
<213> ORGANISM: Homo sapiens

<400> SEQUENCE: 30

Met Phe Ser Met Arg Ile Val Cys Leu Val Leu Ser Val Val Gly Thr
1               5                   10                  15

Ala Trp Thr Asp
            20

<210> SEQ ID NO 31
<211> LENGTH: 28
<212> TYPE: PRT
<213> ORGANISM: Homo sapiens

<400> SEQUENCE: 31

Met Gly Ala Leu Arg Pro Thr Leu Leu Pro Ser Leu Pro Leu Leu
1               5                   10                  15

Leu Leu Leu Met Leu Gly Met Gly Cys Trp Ala Asp
            20                  25

<210> SEQ ID NO 32
<211> LENGTH: 1927
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

```
gttgacattg attattgact agttattaat agtaatcaat tacgggtca ttagttcata      60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta acgccaatag ggactttcca    240
ttgacgtcaa tgggtggact atttacggta aactgcccac ttggcagtac atcaagtgta    300
tcatatgcca agtacgcccc ctattgacgt caatgacggt aaatggcccg cctggcatta    360
tgcccagtac atgaccttat gggactttcc tacttggcag tacatctacg tattagtcat    420
cgctattacc atggccgggc ccagcacccc aaggcggcca acgccaaaac tctccctcct    480
cctcttcctc aatctcgctc tcgctctttt tttttttcgc aaaaggaggg gagaggggt     540
aaaaaaatgc tgcactgtgc ggcgaagccg gtgagtgagc ggcgcgggc caatcagcgt    600
gcgccgttcc gaaagttgcc ttttatggct cgagcggccg cggcggcgcc ctataaaacc    660
cagcggcgcg acgcgccacc accgccgaga ccgcgtccgc ccgcgagca cagagcctcg    720
cctttgccga tccgccgccc gtccacaccc gccgccaggt aagcccggcc agccgaccgg    780
ggcaggcggc tcacggcccg gccgcaggcg ccgcggccc cttcgcccgt gcagagccgc    840
cgtctgggcc gcagcggggg gcgcatgggg ggggaaccgg accgccgtgg ggggcgcggg    900
agaagcccct gggcctccgg agatggggga cacccacgc cagttcggag gcgcgaggcc    960
gcgctcggga ggcgcgctcc gggggtgccg ctctcggggc gggggcaacc ggcggggtct   1020
ttgtctgagc cgggctcttg ccaatgggga tcgcagggtg ggcgcggcgg agccccgcc   1080
aggcccggtg ggggctgggg cgccattgcg cgtgcgcgct ggtcctttgg gcgctaactg   1140
```

```
cgtgcgcgct gggaattggc gctaattgcg cgtgcgcgct gggactcaag gcgctaactg   1200
cgcgtgcgtt ctggggcccg gggtgccgcg gcctgggctg gggcgaaggc gggctcggcc   1260
ggaaggggtg gggtcgccgc ggctcccggg cgcttgcgcg cacttcctgc ccgagccgct   1320
ggccgcccga gggtgtggcc gctgcgtgcg cgcgcgccga cccggcgctg tttgaaccgg   1380
gcggaggcgg ggctggcgcc cggttgggag ggggttgggg cctggcttcc tgccgcgcgc   1440
cgcggggacg cctccgacca gtgtttgcct tttatggtaa taacgcggcc ggcccggctt   1500
cctttgtccc caatctgggc gcgcgccggc gccccctggc ggcctaagga ctcggcgcgc   1560
cggaagtggc cagggcgggg gcgacctcgg ctcacagcgc gcccggctat tctcgcagct   1620
tttgctaatc atgttcatac ctcttatctt cctcccacag ctcctgggca acgtgctggt   1680
ctgtgtgctg gcccatcact ttggcaaaga attcatgttt ccatgagga tcgtctgcct   1740 ggtcctaagt gtggtgggca cagcatggac tgacgcgccc gggccggcca ggcgcgcgcg   1800
ccgtacgtac gaagcttggt accgagctcg gatccactcc agtgtggtgg aattctgcag   1860
atatccagca cagtggcggc cgctcgagga gggcccgaac aaaaactcat ctcagaagag   1920
gatctga                                                            1927

<210> SEQ ID NO 33
<211> LENGTH: 1951
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta acgccaatag ggactttcca    240
ttgacgtcaa tgggtggact atttacggta aactgcccac ttggcagtac atcaagtgta    300
tcatatgcca gtacgccccc tattgacgtc aatgacggt aaatggcccg cctggcatta    360
tgcccagtac atgaccttat gggactttcc tacttggcag tacatctacg tattagtcat    420
cgctattacc atggccgggc ccagcacccc aaggcggcca acgccaaaac tctccctcct    480
cctcttcctc aatctcgctc tcgctctttt ttttttcgc aaaaggaggg gagaggggt    540 aaaaaatgc tgcactgtgc ggcgaagccg gtgagtgagc ggcgcgggc caatcagcgt    600 gcgccgttcc gaaagttgcc ttttatggct cgagcgccg cggcggcgcc ctataaaacc    660
cagcggcgcg acgcgccacc accgccgaga ccgcgtccgc cccgcgagca cagagcctcg    720
cctttgccga tccgccgccc gtccacaccc gccgccaggt aagcccggcc agccgaccgg    780
ggcaggcggc tcacggcccg gccgcaggcg gccgcggccc cttcgcccgt gcagagccgc    840
cgtctgggcc gcagcggggg gcgcatgggg ggggaaccgg accgccgtgg ggggcgcggg    900
agaagcccct gggcctccgg agatggggga cacccccacgc cagttcggag gcgcgaggcc    960
gcgctcggga ggcgcgctcc gggggtgccg ctctcggggc gggggcaacc ggcggggtct   1020
ttgtctgagc cgggctcttg ccaatgggga tcgcagggtg ggcgcggcgg agccccgcc   1080 aggcccggtg ggggtgggg cgccattgcg cgtgcgcgct ggtcctttgg gcgctaactg   1140
cgtgcgcgct gggaattggc gctaattgcg cgtgcgcgct gggactcaag gcgctaactg   1200
```

-continued

```
cgcgtgcgtt ctggggcccg gggtgccgcg gcctgggctg gggcgaaggc gggctcggcc    1260
ggaaggggtg gggtcgccgc ggctcccggg cgcttgcgcg cacttcctgc ccgagccgct    1320
ggccgcccga gggtgtggcc gctgcgtgcg cgcgcgccga cccggcgctg tttgaaccgg    1380
gcggaggcgg ggctggcgcc cggttgggag ggggttgggg cctggcttcc tgccgcgcgc    1440
cgcggggacg cctccgacca gtgtttgcct tttatggtaa taacgcggcc ggcccggctt    1500
cctttgtccc caatctgggc gcgcgccggc gcccctggc ggcctaagga ctcggcgcgc     1560
cggaagtggc cagggcgggg cgacctcgg ctcacagcgc gcccggctat tctcgcagct     1620
tttgctaatc atgttcatac ctcttatctt cctcccacag ctcctgggca acgtgctggt    1680
ctgtgtgctg gcccatcact ttggcaaaga attcatgggc gccctcaggc ccacgctgct    1740
gccgccttcg ctgccgctgc tgctgctgct aatgctagga atgggatgct gggccgacgc    1800 gccccgggccg ccaggcgcg cgcgccgtac gtacgaagct tggtaccgag ctcggatcca    1860
ctccagtgtg gtggaattct gcagatatcc agcacagtgg cggccgctcg aggagggccc    1920
gaacaaaaac tcatctcaga agaggatctg a                                   1951
```

<210> SEQ ID NO 34
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
tccactggtg acgcgcccgg gccggccagg cgcgcc                              36

<210> SEQ ID NO 35
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
ggggcgcctg gccggcccgg gcgcgtcacc agtgga                              36

<210> SEQ ID NO 36
<211> LENGTH: 60
<212> TYPE: DNA
<213> ORGANISM: Homo sapiens
<220> FEATURE:
<221> NAME/KEY: CDS
<222> LOCATION: (1)..(60)

<400> SEQUENCE: 36 atg ttt tcc atg agg atc gtc tgc ctg gtc cta agt gtg gtg ggc aca    48
Met Phe Ser Met Arg Ile Val Cys Leu Val Leu Ser Val Val Gly Thr
1               5                   10                  15 gca tgg act gac                                                     60
Ala Trp Thr Asp
            20

<210> SEQ ID NO 37
<211> LENGTH: 84
<212> TYPE: DNA
<213> ORGANISM: Homo sapiens
<220> FEATURE:
<221> NAME/KEY: CDS

<222> LOCATION: (1)..(84)

<400> SEQUENCE: 37

```
atg ggc gcc ctc agg ccc acg ctg ctg ccg cct tcg ctg ccg ctg ctg      48
Met Gly Ala Leu Arg Pro Thr Leu Leu Pro Pro Ser Leu Pro Leu Leu
1               5                   10                  15 ctg ctg cta atg cta gga atg gga tgc tgg gcc gac                       84
Leu Leu Leu Met Leu Gly Met Gly Cys Trp Ala Asp
            20                  25
```

<210> SEQ ID NO 38
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(72)

<400> SEQUENCE: 38

```
atg gag aca gac aca ctc ctg cta tgg gta ctg ctc tgg gtt cca          48
Met Glu Thr Asp Thr Leu Leu Leu Trp Val Leu Leu Trp Val Pro
1               5                   10                  15 ggt tcc act ggt gac gcg ccc ggg ccg                                  75
Gly Ser Thr Gly Asp Ala Pro Gly Pro
            20
```

<210> SEQ ID NO 39
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

```
Met Glu Thr Asp Thr Leu Leu Leu Trp Val Leu Leu Leu Trp Val Pro
1               5                   10                  15

Gly Ser Thr Gly Asp Ala Pro Gly
            20
```

<210> SEQ ID NO 40
<211> LENGTH: 5
<212> TYPE: PRT
<213> ORGANISM: Homo sapiens

<400> SEQUENCE: 40

```
Leu Leu Leu Leu Leu
1               5
```